(12) United States Patent
Hedley et al.

(10) Patent No.: US 12,383,542 B2
(45) Date of Patent: *Aug. 12, 2025

(54) METHODS OF TREATING OVARIAN CANCER

(71) Applicant: TESARO, INC., Waltham, MA (US)

(72) Inventors: Mary Lynne Hedley, Waltham, MA (US); Robert Martell, Waltham, MA (US)

(73) Assignee: Tesaro, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/986,536

(22) Filed: May 22, 2018

(65) Prior Publication Data

US 2018/0311224 A1 Nov. 1, 2018

Related U.S. Application Data

(63) Continuation of application No. PCT/US2017/040039, filed on Jun. 29, 2017.

(60) Provisional application No. 62/470,141, filed on Mar. 10, 2017, provisional application No. 62/402,427, filed on Sep. 30, 2016, provisional application No. 62/356,461, filed on Jun. 29, 2016.

(51) Int. Cl.
*A61K 31/454* (2006.01)
*A61K 31/4745* (2006.01)
*A61P 35/00* (2006.01)
*A61K 9/48* (2006.01)
*C12Q 1/6886* (2018.01)

(52) U.S. Cl.
CPC ........ *A61K 31/454* (2013.01); *A61K 31/4745* (2013.01); *A61P 35/00* (2018.01); *A61K 9/48* (2013.01); *C12Q 1/6886* (2013.01); *C12Q 2600/106* (2013.01); *C12Q 2600/156* (2013.01)

(58) Field of Classification Search
CPC .... A61K 31/454; A61K 31/4745; A61P 35/00
See application file for complete search history.

(56) References Cited

U.S. PATENT DOCUMENTS

| | | | |
|---|---|---|---|
| 8,071,623 B2 | 12/2011 | Jones et al. | |
| 8,436,185 B2 | 5/2013 | Foley et al. | |
| 9,580,407 B2 | 2/2017 | Chung et al. | |
| 9,738,915 B2 | 8/2017 | Bulger et al. | |
| 2009/0123419 A1 | 5/2009 | Sherman et al. | |
| 2009/0275619 A1 | 11/2009 | Boueres et al. | |
| 2010/0009930 A1 | 1/2010 | Sherman et al. | |
| 2010/0286157 A1 | 11/2010 | Quigley et al. | |
| 2010/0286203 A1 | 11/2010 | Foley et al. | |
| 2011/0118217 A1 | 5/2011 | Gudmundsson et al. | |
| 2011/0201657 A1 | 8/2011 | Boueres et al. | |
| 2012/0207856 A1 | 8/2012 | Ajay et al. | |
| 2012/0214998 A1 | 8/2012 | Bierlmaier et al. | |
| 2013/0310424 A1 | 11/2013 | Surber | |
| 2014/0363521 A1* | 12/2014 | Abkevich | C12Q 1/6858 424/649 |
| 2015/0110869 A1 | 4/2015 | Philip et al. | |
| 2015/0344968 A1 | 12/2015 | Johnson | |
| 2016/0160294 A1 | 6/2016 | Wilcoxen et al. | |
| 2017/0000885 A1 | 1/2017 | Rhee et al. | |
| 2017/0029428 A1 | 2/2017 | Blatter et al. | |
| 2017/0137403 A1 | 5/2017 | Chung et al. | |
| 2017/0335359 A1 | 11/2017 | Bulger et al. | |
| 2019/0060285 A1* | 2/2019 | Proia | A61P 15/00 |
| 2021/0106574 A1 | 4/2021 | Feng et al. | |
| 2022/0175751 A1 | 6/2022 | Hedley et al. | |
| 2022/0175752 A1 | 6/2022 | Hedley et al. | |

FOREIGN PATENT DOCUMENTS

| | | |
|---|---|---|
| CA | 2893280 | 6/2014 |
| CN | 105384695 | 3/2016 |
| CN | 105960415 | 9/2016 |
| CN | 106132439 | 11/2016 |
| CN | 106432055 | 2/2017 |
| CN | 106496187 | 3/2017 |
| JP | 2011-506252 | 3/2011 |
| JP | 2011-509252 | 3/2011 |
| JP | 2011-509253 | 3/2011 |
| JP | 2017-504623 | 2/2017 |
| JP | 2017-509631 | 4/2017 |
| JP | 2017-527799 | 9/2017 |
| WO | WO-2007/113596 | 11/2007 |
| WO | WO-2008/084261 | 7/2008 |
| WO | WO-2009/087381 | 6/2009 |
| WO | WO 2011/058367 | 5/2011 |
| WO | WO 2011/153383 | 12/2011 |
| WO | WO 2011/160063 | 12/2011 |
| WO | WO 2012/027224 | 3/2012 |
| WO | WO 2013/182645 | 12/2013 |
| WO | WO 2014052550 A1 | 4/2014 |
| WO | WO-2014/088983 | 6/2014 |

(Continued)

OTHER PUBLICATIONS

Over Sandhu et a., "The poly(ADP-ribose) polymerase inhibitor niraparib (MK4827) in BRCA mutation carriers and patients with sporadic cancer: a phase 1 dose-escalation trial," Lancet Oncol 2013; 14:882-92.*
Jones et al., "Niraparib: A Poly(ADP-ribose) Polymerase (PARP) Inhibitor for the Treatment of Tumors with Defective Homologous Recombination," Journal of Medicinal Chemistry, Mar. 11, 2015.*
Konstantinopolous et al., "Homologous recombination deficiency: Exploiting the fundamental vulnerability of ovarian cancer," Cancer Discov. Nov. 2015; 5(11):1137-1154.*
Michie et al., "Final Result of the phase I trial of niraparib (MK4827), a poly(ADP)ribose polymerase (PARP) inhibitor incorporating proof of concept biomarker studies and expansion cohorts involving BRCA1/2 mutation carriers, sporadic ovarian, and castration resistant prostate cancer (CRPC)," JCO May 20, 2013.*

(Continued)

*Primary Examiner* — Jared Barsky
(74) *Attorney, Agent, or Firm* — Fish & Richardson P.C.

(57) ABSTRACT

The present invention provides methods of administering a PARP inhibitor to a cancer patient.

22 Claims, 20 Drawing Sheets

(56) References Cited

FOREIGN PATENT DOCUMENTS

| WO | WO-2014/088984 | 6/2014 |
|---|---|---|
| WO | WO 2014/138101 | 9/2014 |
| WO | WO 2014/179664 | 11/2014 |
| WO | WO 2015108986 A1 | 7/2015 |
| WO | WO 2015/119930 | 8/2015 |
| WO | WO 2015/153514 | 10/2015 |
| WO | WO 2015/184145 | 12/2015 |
| WO | WO-2016/094391 | 6/2016 |
| WO | WO 2019/123207 | 6/2016 |
| WO | WO 2016/200835 | 12/2016 |
| WO | WO 2017/075091 | 5/2017 |
| WO | WO 2017/139694 | 8/2017 |
| WO | WO 2018/005818 | 1/2018 |
| WO | WO 2018/023017 | 2/2018 |
| WO | WO 2018/183349 | 10/2018 |
| WO | WO 2018/183354 | 10/2018 |
| WO | WO 2018/200517 | 11/2018 |
| WO | WO 2018/201096 | 11/2018 |
| WO | WO 2019/005762 | 1/2019 |
| WO | WO 2019/067634 | 4/2019 |
| WO | WO 2019/133697 | 7/2019 |
| WO | WO 2021/011609 | 1/2021 |

OTHER PUBLICATIONS

Telli et al., Homologous Recombination Deficiency (HRD) Score Predicts Response to Platinum-Containing Neoadjuvant Chemotherapy in Patients with Triple-Negative Breast Cancer, Clin Cancer Res (published online Mar. 8, 2016).*
AlHilli MM et al., "In vivo anti-tumor activity of the PARP inhibitor niraparib in homologous recombination deficient and proficient ovarian carcinoma: Single agent and combination response", Mol Cancer Ther. *Gynecol Oncol* 2016;143(2):379-388.
Audeh MW, "Novel treatment strategies in triple-negative breast cancer: specific role of poly(adenosine diphosphate-ribose) polymerase inhibition", Pharmgenomics Pers Med, Oct. 2014, 7: 307-316.
Bridges KA et al., "Niraparib (MK-4827), a novel poly(ADP-Ribose) polymerase inhibitor, radiosensitizes human lung and breast cancer cells", *Oncotarget* Jul. 15, 2014;5(13):5076-86.
Carey JPW et al., "Synthetic Lethality of PARP Inhibitors in Combination with MYC Blockade Is Independent of BRCA Status in Triple-Negative Breast Cancer", *Cancer Res.* Feb. 1, 2018;78(3):742-57.
Chang H et al., "Enhanced Anti-Tumor Effects of Selinexor and Niraparib in Preclinical Models of Ovarian Cancer", (Abstract 5826). Presented at AACR 2018 (Poster).
Deas O et al., "Preclinical evaluation of the PARP inhibitor niraparib and cytotoxic chemotherapy alone or in combination in a panel of 25 triple-negative breast cancer PDX models: relevance of BRCA mutations, HRD status and other biomarkers", AACR 2016. (Oral Presentation).
Del Campo JM et al., "The Successful Phase 3 Niraparib ENGOT-OV16/NOVA Trial Included a Substantial Number of Patients with Platinum Resistant Ovarian Cancer", ASCO 2017 (Poster).
Engert F et al., "PARP Inhibitors Sensitize Ewing Sarcoma Cells to Temozolomide-Induced Apoptosis via the Mitochondrial Pathway", *Mol Cancer Ther Dec.* 2015;14(12):2818-30.
Fabbro M et al., "Safety and efficacy of niraparib in elderly patients (Pts) with recurrent ovarian cancer (OC)", Presented at ESMO; Sep. 8-12, 2017; Madrid, Spain. 934PD.
Fisher M et al., "Cost-effectiveness of niraparib versus routine surveillance, olaparib and rucaparib for the maintenance treatment of adult patients with ovarian cancer in the United States", Accepted at ASCO 2018 (Poster).
Genther-Williams SM et al., "Treatment with the PARP inhibitor, niraparib, sensitizes colorectal cancer cell lines to irinotecan regardless of MSI/MSS status", *Cancer Cell Int* Feb. 4, 2015;15(1):14.

González MA et al., "A randomized, double-blind phase 3 trial of niraparib maintenance treatment in patients with HRD+ advanced ovarian cancer after response to front-line platinum-based chemotherapy", ASCO 2016. (Poster).
González MA et al., "A randomized, double-blind, placebo-controlled multicenter phase 3 trial of niraparib maintenance treatment in patients with advanced ovarian cancer following frontline chemotherapy", Presented at ESMO; Sep. 8-12, 2017; Madrid, Spain. 986TiP.
González MA et al., "A randomized, double-blind phase 3 trial of niraparib maintenance treatment in patients with HRD+ advanced ovarian cancer after response to front-line platinum-based chemotherapy", SGO 2017 (Poster).
González MA et al., "The ENGOT-OV26/PRIMA phase 3 trial: Niraparib maintenance treatment in patients with advanced ovarian cancer who responded to front-line platinum-based therapy", ESGO 2017 (e-poster).
Guy J et al., "Cost-effectiveness of niraparib versus routine surveillance and olaparib for the maintenance treatment of adult patients with ovarian cancer in the United States", Accepted at ISPOR 2018 (Poster).
Haluska P et al., "Homologous recombination deficiency (HRD) score and niraparib efficacy in high grade ovarian cancer", Emergency Nurses Association 2014. (Oral Presentation).
Harrow B et al., "Disease Burden During the 'Watchful Waiting' Period in Women with Recurrent Ovarian Cancer in Germany", EU ISPOR 2017 (Poster).
Harrow B et al., "Disease burden during the "watchful waiting" period in patients with recurrent ovarian cancer", Presented at ESMO; Sep. 8-12, 2017; Madrid, Spain. 962P.
Hopkins TA et al., "Mechanistic dissection of PARP1 trapping and the impact on in vivo tolerability and efficacy of PARP inhibitors", *Mol Cancer Res* Jul. 27, 2015.
Jones P et al., "Discovery of 2-{4-[(3S)-piperidin-3-yl]phenyl}-2H-indazole-7-carboxamide (MK-4827): a novel oral poly(ADP-ribose)polymerase (PARP) inhibitor efficacious in BRCA-1 and -2 mutant tumors", *J Med Chem* Nov. 26, 2009;52(22):7170-85.
Jones P et al., "Niraparib: A poly(ADP-ribose) polymerase (PARP) inhibitor for the treatment of tumors with defective homologous recombination", *J Med Chem* Apr. 23, 2015;58(8):3302-14.
Konstantinopoulos PA et al., "Dose-finding combination study of niraparib and pembrolizumab in patients (pts) with metastatic triple-negative breast cancer (TNBC) or recurrent platinum-resistant epithelial ovarian cancer (OC) (TOPACIO/Keynote-162)", Presented at ESMO; Sep. 8-12, 2017; Madrid, Spain. 1143PD.
Konstantinopoulos P et al., "Phase 1/2 study of niraparib plus pembrolizumab in patients with triple-negative breast cancer or recurrent ovarian cancer (Keynote-162)", ASCO 2016. (Poster).
Konstantinopoulos PA et al., "TOPACIO: Preliminary activity and safety in patients with platinum-resistant ovarian cancer in a phase 1/2 study of niraparib in combination with pembrolizumab", SGO 2018 (Oral).
Kurzrock R et al., "A phase I study of niraparib in combination with temozolomide (TMZ) in patients with advanced cancer", ASCO 2014. (Poster).
Ledermann J et al., Niraparib maintenance therapy in patients with platinum-sensitive recurrent ovarian cancer (ENGOT-OV16/NOVA trial). BGCS 2017 (Poster, encore publication).
Lodhia KA et al., "Characterization of 148 Ovarian Cancer tumografts (Avatars) using BROCA-HR deep sequencing", TAT 2015. (Poster).
Lord R et al., "Safety and dose modification for patients with low body weight receiving niraparib in the ENGOT-OV16/NOVA phase 3 trial", SGO 2018 (Oral).
Mahner S et al., "ENGOT-OV16/NOVA: Results of secondary efficacy endpoints of niraparib maintenance therapy in ovarian cancer", SGO 2017 (Oral presentation).
Matulonis UA et al., "A phase 3 randomized double-blind trial of maintenance with niraparib versus placebo in patients with platinum-sensitive ovarian cancer (ENGOT-OV16/NOVA trial)", ASCO 2014. (Poster).
Matulonis U et al., "Engot-ov16/nova: A maintenance study with niraparib versus placebo in patients with platinum-sensitive ovarian

(56) References Cited

OTHER PUBLICATIONS cancer", [abstract No. IGCS-0912]. Int J Gynecol Cancer. 2016; 26 (Suppl 3): 19-20. IGCS 2016 poster.

Matulonis UA et al., "Long Term Benefit of Niraparib Treatment of Recurrent Ovarian Cancer (OC)", ASCO 2017 (Poster).

Michie CO et al., "Final results of the phase I trial of niraparib (MK4827), a poly(ADP)ribose polymerase (PARP) inhibitor incorporating proof of concept biomarker studies and expansion cohorts involving BRCA1/2 mutation carriers, sporadic ovarian, and castration resistant prostate cancer (CRPC)", ASCO 2013. (Poster).

Mikule K et al., "A mouse avatar tumor maintenance study identified a subset of SCLC patient-derived tumor xenograft models sensitive to the PARP inhibitor niraparib", EORTC-NCI-AACR 2015.

Mikule K et al., "A preclinical evaluation of niraparib efficacy as monotherapy, maintenance and after olaparib treatment (PARP inhibitor after PARP inhibitor) in patient-derived ovarian xenograft tumor models", ECCO 2017. (Poster).

Mikule K et al., "The PARP inhibitor, niraparib, crosses the blood brain barrier in rodents and is efficacious in a BRCA2-mutant intracranial tumor model", EORTC-NCI-AACR 2015. (Poster).

Mirza MR et al., "A phase 1 study to evaluate the safety and tolerability of bevacizumab-niraparib combination therapy and determine the recommended phase 2 dose (RP2D) in women with platinum-sensitive epithelial ovarian cancer (ENGOT-OV24/AVANOVA1)", Presented at ESMO; Sep. 8-12, 2017; Madrid, Spain. 953P.

Mirza MR et al., "Efficacy of Niraparib on Progression-free Survival (PFS) in Patients (Pts) with Recurrent Ovarian Cancer (OC) with Partial Response to the Last Platinum-based Chemotherapy" ASCO 2017. (Poster).

Mirza MR et al., "ENGOT-OV16/NSGO/NOVA: A phase 3 randomized double-blind trial of maintenance with parp-inhibitor niraparib vs. placebo in patients with platinum-sensitive ovarian cancer", ESMO 2014. (Poster).

Mirza M et al., "Engot-OV16/NOVA: A phase 3 randomized double-blind trial of maintenance with PARP-inhibitor niraparib versus placebo in patients with platinum-sensitive ovarian cancer. IGCS 2014", (Oral Presentation).

Mirza MR et al., "Niraparib Maintenance Therapy in Platinum-Sensitive, Recurrent Ovarian Cancer," *N Engl J Med* Dec. 1, 2016;375(22):2154-2164. Epub Oct. 7, 2016.

Mirza MR et al., "Niraparib alone versus niraparib-bevacizumab combination versus bevacizumab followed by niraparib in women with platinum-sensitive ovarian cancer", ASCO 2015. (Poster).

Mirza MR et al., "Niraparib maintenance therapy in patients with platinum-sensitive recurrent ovarian cancer (ENGOT-OV16/NOVA trial)", ESMO 2016 (Oral Presentation).

Moore K et al., "Food effect sub study of a phase 3 randomized double-blind trial of maintenance with niraparib, a poly(adp)ribose polymerase (PARP) inhibitor in platinum-sensitive ovarian cancer patients", ESGO 2015. (Poster).

Moore KN et al., "Food effect substudy of a phase 3 randomized double-blind trial of maintenance with niraparib (MK4827), a poly(ADP)ribose polymerase (PARP) inhibitor versus placebo in patients with platinum sensitive ovarian cancer", ASCO 2014. (Online only).

Moore KN et al., "Phase 2, open-label study of niraparib in women with advanced, relapsed, high-grade serous epithelial ovarian, fallopian tube or primary peritoneal cancer after ≥3 previous chemotherapy regimens", ASCO 2015. (Poster).

Moore K et al., "Safety and efficacy of niraparib in patients with advanced, relapsed, high-grade serous epithelial ovarian, fallopian tube, or primary peritoneal cancer (QUADRA)", [abstract No. IGCS-0883]. Int J Gynecol Cancer. 2016; 26 (Suppl 3): 784 .IGCS 2016 poster.

Moore K et al., "The effect of food on the pharmacokinetics of niraparib, a poly(ADP-ribose) polymerase (PARP) inhibitor, in patients with recurrent ovarian cancer", *Cancer Chemother Pharmacol.* Mar. 1, 2018;81(3):497-503.

Mueller S et al., "Poly (ADP-Ribose) polymerase inhibitor MK-4827 together with radiation as a novel therapy for metastatic neuroblastoma", *Anticancer Res* Mar. 2013;33(3):755-62.

Murai J et al., "Trapping of PARP1 and PARP2 by Clinical PARP Inhibitors" *Cancer Res* Nov. 1, 2012;72(21):5588-99.

Neeser K et al., "Budget impact of niraparib as maintenance treatment for Medicare patients with recurrent ovarian, fallopian tube, or primary peritoneal cancer who are in complete or partial response to platinum-based chemotherapy", Accepted at ISPOR 2018 (Poster).

Neeser K et al., "The cost consequences of maintenance therapies for patients with recurrent ovarian, fallopian tube, or primary peritoneal cancer who are in complete or partial response to platinum-based chemotherapy", NCCN 2018. JNCCN17-269 (Poster).

Oza A et al., "Quality of live in recurrent ovarian cancer patients treated with niraparib: Results from the ENGOT-OV16/NOVA Trial", Presented at ESMO; Sep. 8-12, 2017; Madrid, Spain. 930O.

Parpos P et al., "Comparison of dose intensity in clinical trial and real world settings for niraparib", Accepted at ISPOR 2018 (Poster).

Postel-Vinay S et al., "A high-throughput screen identifies PARP1/2 inhibitors as a potential therapy for ERCC1-deficient non-small cell lung cancer", *Oncogene* Nov. 21, 2013;32(47):5377-87.

Sambade MJ et al., "Efficacy and pharmacokinetics of niraparib in BRCA-mutant and wild-type intracranial triple negative breast cancer murine models", (Abstract: 2813). Presented at AACR 2018 (Poster).

Sandhu SK et al., "The poly(ADP-ribose) polymerase inhibitor niraparib (MK4827) in BRCA mutation carriers and patients with sporadic cancer: a phase 1 dose-escalation trial", *Lancet Oncol* Aug. 2013; 14(9):882-92.

Schelman WR et al., "First in Human Trial of a Poly(ADP-ribose) Polymerase (PARP) Inhibitor MK-4827 in Advanced Cancer Patients with Antitumor Activity in BRCA-Deficient Tumors and Sporadic Ovarian Cancers", ASCO 2011. (Poster).

Shen Y et al., "Trapping Poly(ADP-Ribose) Polymerase", *J Pharmacol Exp Ther* Jun. 2015;353(3):446-57.

Sun K et al., "A comparative pharmacokinetic-pharmacodynamic-treatment study of PARP inhibitors demonstrates favorable properties for niraparib activity in pre-clinical tumor models", AACR/NCI/EORTC Oct. 2017(Poster).

Timms K et al., "DNA repair deficiencies in ovarian cancer: Genomic analysis of high grade serous ovarian tumors from the NOVA study", ECC/ESMO 2015. (Poster).

Tryfonidis K et al., "A phase III randomized trial of niraparib versus physician's choice in previously-treated, HER2 negative, germline-BRCA mutated breast cancer patients: An EORTC-BIG intergroup study", ASCO 2014. (Poster).

Tryfonidis K et al., "A phase III randomized trial of niraparib versus physician's choice in previously treated, HER2 negative, germline-BRCA mutated breast cancer patients: An EORTC-BIG intergroup study", SABCS 2015. (Poster).

Van Andel L et al., "Determination of the absolute oral bioavailability of niraparib by simultaneous administration of a 14C-microtracer and therapeutic dose in cancer patients", Cancer Chemother Pharmacol. 2017.

Van Andel L et al., "Human mass balance study and metabolite profiling of 14C-niraparib, a novel poly(ADP-Ribose) polymerase (PARP)-1 and PARP-2 inhibitor, in patients with advanced cancer", Invest New Drugs. 2017.

Van Andel L et al., "Liquid chromatography-tandem mass spectrometry assay for the quantification of niraparib and its metabolite M1 in human plasma and urine", *J Chromatogr B Analyt Technol Biomed Life Sci* 2017;1040:14-21.

Vinayak S et al., "TOPACIO/Keynote-162: Niraparib + pembrolizumab in patients (pts) with metastatic triple-negative breast cancer (TNBC), a phase 2 trial", Accepted at ASCO 2018 (Oral).

Wang S et al., "Elevation of immune cell infiltration and interferon-stimulated gene expression is associated with niraparib treatment in murine syngeneic tumor models", AACR/NCI/EORTC Oct. 2017 (Poster).

Wang S et al., "Evaluation of niraparib in combination with anti-PD-1/anti-PD-L1 in preclinical models", 3rd DNA replication/Repair Structures and Cancer Conference.

(56) References Cited

OTHER PUBLICATIONS

Wang S et al., "Evaluation of niraparib in combination with anti-pd-1/anti-pd-l1 in preclinical models", (Abstract 1724). Presented at AACR 2018.
Wang L et al., "MK-4827, a PARP-1/-2 inhibitor, strongly enhances response of human lung and breast cancer xenografts to radiation", *Invest New Drugs* Dec. 2012;30(6):2113-20.
Wang Y et al., "Niraparib, a selective PARP 1/2 inhibitor, is efficacious in pre-clinical models of small-cell lung cancer", EORTC-NCI-AACR 2014. (Poster).
Wang J et al., "Preclinical Anti-tumor Activity of Niraparib and Its Combination with Anti-PD-1 Therapy", PARP2017 (oral presentation).
Wang S et al., "Preclinical evaluation of niraparib in combination with anti-PD1/anti-PDL1 in mouse-derived syngeneic transplant models", AACR I&I Oct. 2017, Abstract B16 (Poster).
Wang J et al., "The exposure-response relationship of niraparib in patients (pts) with gBRCAmut and non-gBRCAmut: results from the Phase 3 ENGOT-OV16/NOVA Trial", Presented at ESMO; Sep. 8-12, 2017; Madrid, Spain. 933PD.
Wang Y et al., "The PARP inhibitor niraparib demonstrates robust activity in a subset of patient-derived triple-negative breast cancer xenograft models", AACR 2014. (Poster).
Wang Y et al., "The PARP inhibitor niraparib demonstrates activity in patient-derived triple-negative breast cancer xenograft models with high homologous recombination deficiency (HRD) score", SABCS 2014. (Poster).
Wilcoxen KM et al, "Homologous recombination deficiency (HRD) score enriches for niraparib sensitive high grade ovarian tumors" ASCO 2015. (Poster).
Zhang Z-Y et al., "Biotransformation and disposition of niraparib, a selective human PARP-1 and PARP-2 antagonist, in vitro", ISSX 2015. (Poster).
Zhang Z-Y et al., "Characterization of absorption, metabolism, and elimination of niraparib, an investigational poly (ADP-ribose) polymerase inhibitor, in cancer patients", EACPT 2017 (oral presentation).
Zhang Z-Y et al., "Disposition and Biotransformation of Niraparib, a Selective Human PARP-1 and PARP-2 Antagonist, in Vivo", ISSX 2015. (Poster).
Zhang ZY et al., "Modeling and impact of organ function on the population pharmacokinetics (PK) of niraparib, a selective poly (ADP-ribose) polymerase (PARP)-1 and -2 inhibitor", Presented at ESMO; Sep. 8-12, 2017; Madrid, Spain. 964P.
Zhang ZY et al., "Pharmacokinetics of the poly (ADP-ribose) polymerase inhibitor (PARPi) niraparib", World Congress on Pharmacology 2017 (oral presentation).
Essel et al., "Niraparib for the treatment of ovarian cancer", Expert Review of Anticancer Therapy, 18(8): 727-733 (2018).
Kang et al., "Regulation of DNA repair in the absence of classical non-homologous end joining", DNA Repair, 68: 34-40 (2018).
Vasconcelos et al., "Meta-analysis on the PARP-inhibitor olaparib reveals therapeutic efficacy in ovarian cancer independent of BRCA1/2 mutation status", Advances in Modern Oncology Research, 2(1): 91-96 (2016).
Moore, "The poly (ADP ribose) polymerase inhibitor niraparib: Management of toxicities", Gynecologic Oncology, 149(1): 214-220 (2018).
Caruso, "Niraparib in ovarian cancer: results to date and clinical potential", Therapeutic Advances in Medical Oncology, 9(9): 579-588 (2017).
Kanjanapan et al., "Niraparib for the treatment of ovarian cancer", Expert Opinion on Pharmacotherapy, 18(6): 631-640 (2017).
Farmer et al., "Targeting the DNA repair defect in BRCA mutant cells as a therapeutic strategy", Nature, 434: 917-921 (2005).
Hamilton et al., "Emotional Distress Following Genetic Testing for Hereditary Breast and Ovarian Cancer: A Meta-Analytic Review", Health Psychol., 28(4): 510-518 (2009).

Listøl et al., "Anxiety and depression symptoms among women attending group-based patient education courses for hereditary breast and ovarian cancer", Hereditary Cancer in Clinical Practice, 15:2, 1-9 (2017).
Ramus, "The Contribution of BRCA1 and BRCA2 to Ovarian Cancer", Mol Oncol., 3(2): 138-150 (2009).
Gelmon et al., "Olaparib in patients with recurrent high-grade serous or poorly differentiated ovarian carcinoma or triple-negative breast cancer: a phase 2, multicentre, open-label, non-randomised study", Lancet Oncol., 12: 852-861 (2011).
Ledermann et al., "Olaparib Maintenance Therapy in Platinum-Sensitive Relapsed Ovarian Cancer", N. Eng. J. Med., 366(15): 1382-1392 (2012).
Moore et al., "Maintenance Olaparib in Patients with Newly Diagnosed Advanced Ovarian Cancer", N. Eng. J. Med. 1-11 (2018).
Moore et al., "Maintenance Olaparib in Patients with Newly Diagnosed Advanced Ovarian Cancer", N. Eng. J. Med. Supplementary Appendix (2018).
"Niraparib Slows Ovarian Cancer Progression", Cancer Discovery., 6(12): OF2, (2016).
Kaufman et al., "Olaparib Monotherapy in Patients With Advanced Cancer and a Germline BRCA1/2 Mutation", Journal of Clinical Oncology, 33(3): 244-250 (2015).
George et al., "Delivering widespread BRCA testing and PARP inhibition to patients with ovarian cancer", Nature Reviews Clinical Oncology, 14(5): 284-296 (2017).
Bryant et al., "Synthetic Lethality with Homologous Recombination Repair Defects", PARP Inhibitors for Cancer Therapy (Cancer Drug Discovery and Development), Chapter 13, 315-344 (2015).
Moore et al., "SOLO1: Phase III trial of maintenance olaparib following platinum-based chemotherapy in newly diagnosed patients with advanced ovarian cancer and a BRCA1/2 mutation", slides presented at European Society for Medical Oncology Congress (2018).
Davies et al., "Top 40 Drugs in the Pipeline", A Supplement to C&EN, 1-33, (2016).
https://www.fool.com/investing/2016/06/29/shares-of-tesaro-inc-have-more-than-doubled-today.aspx.
https://www.streetinsider.com/Analyst+Comments/TESARO+%28TSRO%29+Phase +3+Niraparib+Results+a+Grand+Slam+-+Mizuho/11784621.htm.
https://www.statnews.com/2016/06/30/ovarian-cancer-new-drugs/.
https://www.medscape.com/viewarticle/870021.
https://www.onclive.com/web-exclusives/fda-approves-niraparib-for-ovarian-cancer.
https://www.esmo.org/Conferences/Past-Conferences/ESMO-2016-Congress/Press-Media/Niraparib-Significantly-Improves-Outcome-of-Ovarian-Cancer-Patients-in-Landmark-Trial.
http://www.ascopost.com/issues/november-25-2016/breakthrough-in-recurrent-ovarian-cancer-niraparib-extends-progression-free-survival-in-platinum-sensitive-disease/.
https://www.mdedge.com/oncologypractice/article/115513/gynecologic-cancer/parp-inhibitor-prolongs-pfs-ovarian-cancer.
http://www.pmlive.com/pharma_news/tesaros_niraparib_threatens_lynparza_after_acing_ovarian_cancer_trial_1160149.
Lynparza® Label Dec. 2014.
Rubraca® Label Dec. 2016.
Zejula® Label Mar. 2017.
Lynparza® Label Aug. 2017.
Rubraca® Label Apr. 2018.
Ledermann et al., "Newly diagnosed and relapsed epithelial ovarian carcinoma: ESMO Clinical Practice Guidelines for diagnosis, treatment and follow-up", Annals of Oncology, 24 (Supplement 6), vi24-vi32 (2013).
FDA Briefing Document: Oncologic Drugs Advisory Committee Meeting, Jun. 25, 2014.
Ledermann et al., "eUpdate Ovarian Cancer Treatment Recommendations", European Society for Oncology (2016).
http://ir.tesarobio.com/news-releases/news-release-details/tesaros-niraparib-significantly-improved-progression-free.
Zejula® Marketing materials (2018).
Mikule, K. "Targeting Cancers with DNA Repair: Beyond BRCA," presented at Boston Oncology Drug Discovery Symposium (2018).

(56) References Cited

OTHER PUBLICATIONS

Zejula® marketing materials, "The NOVA Trial Independently Tested the Benefit of ZEJULA in gBRCAmut and Non-gBRCAmut Populations", (2017).
https://www.astrazeneca.com/media-centre/press-releases/2011/AstraZeneca-updates-on-olaparib-and-TC-5214-development-programmes-20122010.html#.
https://www.astrazeneca.com/media-centre/press-releases/2013/astrazeneca-olaparib-clinical-programme-brca-mutated-ovarian-cancer-treatment-04092013.html#.
Lederman et al., "Olaparib maintenance therapy in patients with platinumsensitive relapsed serous ovarian cancer: a preplanned retrospective analysis of outcomes by BRCA status in a randomised phase 2 trial", Lancet Oncology, 15: 852-861 (2014).
Umscheid et al., "Key Concepts of Clinical Trials: A Narrative Review", Postgraduate Medicine, 123(5): 194-204 (2011).
Mahipal et al., "Risks and Benefits of Phase 1 Clinical Trial Participation", Cancer Control, 21(3): 193-199 (2014).
Mandrekar et al., "Design of clinical trials for biomarker research in oncology", Clin. Invest., 1(12): 1627-1636 (2011).
Yap et al., "Poly(ADP-Ribose) Polymerase (PARP) Inhibitors: Exploiting a Synthetic Lethal Strategy in the Clinic", CA Cancer J Clin, 61(1):31-49 (2011).
Lin et al., "Reinventing clinical trials: a review of innovative biomarker trial designs in cancer therapies", British Medical Bulletin, 114(1):17-27 (2015).
Cook et al., "Early phase clinical trials to identify optimal dosing and safety", Molecular Oncology, 9(5): 997-1007 (2015).
http://www.pharmafile.com/news/188925/fda-rejects-olaparib.
https://blogs.shu.edu/cancer/2014/06/26/parp-inhibitor-rejected-by-fda-advisory-committee/.
http://www.egdutton2.com/research/progress/snapshots/ovarian.html.
http://www.egdutton2.com/types/ovarian/hp/ovarian-epithelial-treatment-pdq.html.
https://ocrahope.org/patients/about-ovarian-cancer/recurrence/.
https://www.astrazeneca-us.com/media/press-releases/2014/lynparza-approved-by-the-us-fda-20141219.html#!
https://ir.clovisoncology.com/investors-and-news/news-releases/press-release-details/2016/Clovis-Oncology-Announces-FDA-Accelerated-Approval-of-RUBRACA-rucaparib-for-the-Monotherapy-Treatment-of-Advanced-Ovarian-Cancer-in-Women-with-Deleterious-Germline-or-Somatic-BRCA-Mutations-Treated-with-Two-or-More-Chemotherapies/default.aspx.
http://ir.tesarobio.com/news-releases/news-release-details/tesaro-announces-us-fda-approval-zejulatm-niraparib-women.
http://www.ascopost.com/issues/january-25-2017/parp-inhibitor-niraparib-yields-unprecedented-results-in-ovarian-cancer-in-phase-iii-trial/?utm_source=TrendMD&utm_medium=cpc&utm_campaign=The_ASCO_Post_TrendMD_0.
https://seekingalpha.com/article/4011207-tesaro-enjoys-ta-dah-moment.
http://ir.tesarobio.com/news-releases/news-release-details/tesaro-and-myriad-announce-companion-diagnostics-collaboration.
Berek et al., "Safety and dose modification for patients receiving niraparib," Ann. Oncol., 29(8):1784-1792, (2018).
Chase et al.; "Profile of Olaparib in the treatment of advanced ovarian cancer," Int J Women's Health., 6(8): 125-129, (2016).
https://www.astrazeneca.com/media-centre/press-releases/2018/solo-1-phase-III-trial-demonstrates-lynparza-maintenance-therapy-cut-risk-of-disease-progression-or-death-by-70-percent-in-patients-with-newly-diagnosed-advanced-brca-mutated-ovarian-cancer.html.
https://www.astrazeneca.com/media-centre/press-releases/2016/lynparza-phase-iii-solo-2-trial-shows-significant-progression-free-survival-benefit-261020161.html#.
https://myriad.com/patients-families/genetic-testing-101/genetic-testing-faqs/.
http://www.ascopost.com/issues/november-25-2016/expert-point-of-view-sandro-pignata-md/.
https://clinicaltrials.gov/ct2/show/NCT02655016?term=niraparib&recrs=d&rank=7.
National Academies of Sciences, Engineering, and Medicine. "Ovarian cancers: Evolving paradigms in research and care" Washington, DC: The National Academies Press (2016).
Morin et al., Ovarian Cancer. In: Schwab M. (eds) Encyclopedia of Cancer. Springer, Berlin, Heidelberg. pp. 2671-2674 (2011).
Ex Parte Liu, Appeal 2018-000869, 2018 WL 3492109 (Jul. 3, 2018).
Ex Parte Pu, Appeal 2017-003775, 2018 WL 3425476 at (Jun. 25, 2018).
https://xconomy.com/boston/2017/03/27/tesaros-ovarian-cancer-drug-gets-fda-nod-no-diagnostic-needed/.
Fong et al., "Inhibition of poly(ADP-ribose) polymerase in tumors from BRCA mutation carriers", N Engl J Med. 2009; 361(2): 123-134.
Audeh et al., "Oral poly(ADP-ribose) polymerase inhibitor olaparib in patients with BRCA1 or BRCA2 mutations and recurrent ovarian cancer: a proof-of-concept trial", Lancet. 2010; 376(9737): 245-251.
Kummar et al., "A phase I study of veliparib in combination with metronomic cyclophosphamide in adults with refractory solid tumors and lymphomas", Clin Cancer Res. 2012; 18(6): 1726-1734.
Turner et al., "Biomarkers of PARP Inhibitor Sensitivity", Breast Cancer Res Treat. 2011; 127(1): 283-286.
Wooster et al., Identification of the breast cancer susceptibility gene BRCA2, Nature. 1995; 378(6559): 789-792.
Chen et al., "BRCA1, BRCA2, and Rad51 operate in a common DNA damage response pathway", Cancer Res. 1999; 59(7 Suppl): 1752s-1756s.
Turner et al., "Hallmarks of 'BRCAness' in sporadic cancers", Nat Rev Cancer. 2004;4(10): 814-819.
Kang et al., "A DNA repair pathway-focused score for prediction of outcomes in ovarian cancer treated with platinum-based chemotherapy", J Natl Cancer Inst. 2012; 104(9): 670-681.
Konstantinopoulos et al., "Gene expression profile of BRCAness that correlates with responsiveness to chemotherapy and with outcome in patients with epithelial ovarian cancer", J Clin Oncol. 2010; 28(22): 3555-3561.
Stefansson et al., "Genomic profiling of breast tumours in relation to BRCA abnormalities and phenotypes", Breast Cancer Res. 2009; 11(4): R47.
Siegel et al., "Cancer statistics, 2014", CA Cancer J Clin. 2014; 64(1): 9-29.
United States Court of Appeals for the Federal Circuit, Novartis Pharmaceuticals Corporation, Novartis AG, Plaintiffs-*Appellees* v. *West-Ward Pharmaceuticals International Limited*, Defendant-Appellant, 2018-1434, Decided: May 13, 2019, 20 pages.
Smietana, K et al., "From the Analyst's Couch—Trends in Clinical Success Rates", Nature Review | Drug Discovery, pp. 1-2, May 20, 2016.
American Cancer Society, "Ovarian Cancer, 2016", http://www.cancer.org/cancer/ovariancancer/index, Accessed May 13, 2019.
Vine et al., "Characterization of prediagnostic symptoms among primary epithelial ovarian cancer cases and controls", Gynecol Oncol. 2003; 90(1): 75-82.
Goff et al., "Frequency of symptoms of ovarian cancer in women presenting to primary care clinics", JAMA. 2004; 291(22): 2705-2712.
Havrilesky et al., "Quality of life in ICON7: need for patients' perspectives", Lancet Oncol. 2013; 14(3): 183-185.
Company B-MS, Taxol® (paclitaxel) Injection Package Insert. 2011; http://www.accessdata.fda.gov/drugsatfda_docs/label/2011/020262s0491bl.pdf, Accessed May 17, 2016.
Birrer, "Ovarian cancer: targeting the untargetable", Am Soc Clin Oncol Educ Book. 2014: 13-15.
Ferrel et al., "Psychological well being and quality of life in ovarian cancer survivors", Cancer. 2003; 98(5): 1061-1071.
Reb, "Transforming the death sentence: elements of hope in women with advanced ovarian cancer", Oncol Nurs Forum. 2007; 34(6): E70-81.

(56) References Cited

OTHER PUBLICATIONS

Havrilesky et al., "Determination of quality of life-related utilities for health states relevant to ovarian cancer diagnosis and treatment", Gynecol Oncol. 2009; 113(2): 216-220.
Fotopoulou, "Limitations to the use of carboplatin-based therapy in advanced ovarian cancer", EJC Suppl. 2014; 12(2): 13-16.
Antoniou et al., "Common breast cancer susceptibility alleles and the risk of breast cancer for BRCA1 and BRCA2 mutation carriers: implications for risk prediction", Cancer Res. 2010; 70(23): 9742-9754.
Watkins et al., "Genomic scars as biomarkers of homologous recombination deficiency and drug response in breast and ovarian cancers", Breast Cancer Res. 2014; 16(3): 211.
Kaelin, "The concept of synthetic lethality in the context of anti-cancer therapy", Nat Rev Cancer, 2005; 5(9): 689-698.
Abkevich et al., "Patterns of genomic loss of heterozygosity predict homologous recombination repair defects in epithelial ovarian cancer", Br J Cancer. 2012; 107(10): 1776-1782.
Birkbak et al., "Telomeric allelic imbalance indicates defective DNA repair and sensitivity to DNA-damaging agents", Cancer Discov. 2012; 2(4): 366-375.
Popova et al., "Ploidy and large-scale genomic instability consistently identify basal-like breast carcinomas with BRCA1/2 inactivation", *Cancer Res.* 2012; 72(21):5454-5462.
Mills et al., "Homologous Recombination deficiency score shows superior association with outcome compared with its individual score components in platinum-treated serous ovarian cancer", Presented for the 47th Annual Meeting of the Society of Gynecologic Oncology, Mar. 19-22, 2016, San Diego.
Freidlin et al., "Adaptive signature design: an adaptive clinical trial design for generating and prospectively testing a gene expression signature for sensitive patients", *Clin Cancer Res.* 2005; 11(21):7872-7878.
Cancer Genome Atlas Research Network, "Integrated genomic analyses of ovarian carcinoma", *Nature*, 2011; 474(7353):609-615.
Mukhopadhyay et al., "Development of a functional assay for homologous recombination status in primary cultures of epithelial ovarian tumor and correlation with sensitivity to poly(ADP-ribose) polymerase inhibitors", *Clin Cancer Res.* 2010;16(8):2344-2351.
Aghajanian et al., "OCEANS: a randomized, double-blind, placebo-controlled phase III trial of chemotherapy with or without bevacizumab in patients with platinum-sensitive recurrent epithelial ovarian, primary peritoneal, or fallopian tube cancer", *J Clin Oncol.* 2012;30(17):2039-2045.
Oza et al., "Progression-free survival in advanced ovarian cancer: a Canadian review and expert panel perspective", *Curr Oncol.* 2011; 18 Suppl 2:S20-27.
Markman et al., "Duration of response to second-line, platinum-based chemotherapy for ovarian cancer: implications for patient management and clinical trial design", *J Clin Oncol.* 2004;22(15):3120-3125.
Tan et al., "Long-term survival and late toxicity after chemoradiotherapy for cervical cancer—the Addenbrooke's experience", *Clin Oncol (R Coll Radiol).* 2008;20(5):358-364.
Bast et al., "Prevention and early detection of ovarian cancer: mission impossible?", *Recent Results Cancer Res.* 2007; 174:91-100.
Herzog et al., "SGO guidance document for clinical trial designs in ovarian cancer: a changing paradigm", *Gynecol Oncol.* 2014;135(1):3-7.
Herzog et al., "Ovarian cancer clinical trial endpoints: Society of Gynecologic Oncology white paper", *Gynecol Oncol.* 2014;132(1):8-17.
Havrilesky et al., "Patient preferences in advanced or recurrent ovarian cancer", *Cancer.* 2014;120(23):3651-3659.
Schiffer et al., "Platelet transfusion for patients with cancer: clinical practice guidelines of the American Society of Clinical Oncology", 2001; 19(5): 1519-1538.
Slichter, "Evidence-based platelet transfusion guidelines", 2007: 172-178.
Beaumont et al., "Validation of the Functional Assessment of Cancer Therapy—Ovarian (FACT-O) Symptom Index (FOSI) in a Phase II Clinical Trial of Pertuzumab in Patients with Advanced Ovarian Cancer", *Journal of Clinical Oncology, 2007 ASCO Annual Meeting Proceedings (Post-Meeting Edition).* 2007;25(18S):16021.
Conner-Spady et al., "Responsiveness of the EuroQol in breast cancer patients undergoing high dose chemotherapy", *Qual Life Res.* 2001; 10(6):479-486.
Vardiman et al., "The 2008 revision of the World Health Organization (WHO) classification of myeloid neoplasms and acute leukemia: rationale and important changes", *Blood.* 2009; 114(5):937-951.
Elston, "On Fisher's Method of Combining p-Values", *Biometrical Journal.* 1991;33(3):339-345.
Chuang-Stein, "Some issues concerning the normalization of laboratory data based on reference ranges", *Drug Information Journal.* 2001;35:153-156.
Jaillette et al., "French Intensive Care Society, International congress—Reanimation 2016", *Ann Intensive Care.* 2016;6(Suppl 1):50.
Matulonis et al., "Phase II study of carboplatin and pemetrexed for the treatment of platinum-sensitive recurrent ovarian cancer", *J Clin Oncol.* 2008;26(35):5761-5766.
Hanker et al., "The impact of second to sixth line therapy on survival of relapsed ovarian cancer after primary taxane/platinum-based therapy", *Ann Oncol.* 2012;23(10):2605-2612.
Franzese et al., "PARP inhibitors in ovarian cancer", Cancer Treatment Reviews, vol. 73: Feb. 1-9, 2019.
Schiewer et al., "PARP-1 regulates DNA repair factor availability", EMBO Molecular Medicine, vol. 10 (12):—Dec. 2018.
Hopkins et al., "PARP1 Trapping by PARP Inhibitors Drives Cytotoxicity in Both Cancer Cells and Healthy Bone Marrow", Molecular Cancer Research, vol. 17 (2): 409-419 Feb. 2019.
Baciarello et al., "Advancing therapies in metastatic castration-resistant prostate cancer", Expert Opinion on Pharmacotherapy, vol. 19 (16): 1797-1804 Nov. 2, 2018.
Caffo et al., "Aberrations of DNA Repair Pathways in Prostate Cancer: Future Implications for Clinical Practice?", Frontiers in Cell and Developmental Biology, vol. 6:—Sep. 5, 2018.
Hill et al., "Prediction of DNA Repair Inhibitor Response in Short-Term Patient-Derived Ovarian Cancer Organoids", Cancer Discovery, vol. 8 (11): 1404-1421 Nov. 2018.
Van Der Biessen et al., "A phase 1 study of PARP-inhibitor ABT-767 in advanced solid tumors with BRCA1/2 mutations and high-grade serous ovarian, fallopian tube, or primary peritoneal cancer", Investigational New Drugs, vol. 36 (5): 828-835, Oct. 2018.
Ethier et al., "The role of niraparib for the treatment of ovarian cancer", Future Oncology, vol. 14 (25): 2565-2577, Oct. 2018.
Wang et al., "Emerging therapeutic modalities of PARP inhibitors in breast cancer", Cancer Treatment Reviews, vol. 68: 62-68, Jul. 2018.
Hoskins, "Inadequate Rates of BRCA Testing with its Negative Consequences for Women with Epithelial Ovarian Cancer and their Families: an Overview of the Literature", Clinical Oncology, vol. 30 (8): 472-483 Sp. Iss. SI, Aug. 2018.
Sharma, "Update on the Treatment of Early-Stage Triple-Negative Breast Cancer", Current Treatment Options in Oncology, vol. 19 (5):—May 2018.
Longoria et al., "Pharmacokinetic drug evaluation of niraparib for the treatment of ovarian cancer", Expert Opinion on Drug Metabolism & Toxicology, vol. 14 (5): 543-550, 2018.
Christenson et al., "PARP inhibitors for homologous recombination-deficient prostate cancer", Expert Opinion on Emerging Drugs, vol. 23 (2): 123-133, 2018.
Moore et al., "The poly (ADP ribose) polymerase inhibitor niraparib: Management of toxicities", Gynecologic Oncology, vol. 149 (1): 214-220, Apr. 2018.
Chen et al., "The promising PARP inhibitors in ovarian cancer therapy: From Olaparib to others", Biomedicine & Pharmacotherapy, vol. 99: 552-560, Mar. 2018.
Geenen et al., "PARP Inhibitors in the Treatment of Triple-Negative Breast Cancer", Clinical Pharmacokinetics, vol. 57 (4): 427-437, Apr. 2018.

(56) References Cited

OTHER PUBLICATIONS

Morgan et al., "PARP inhibitors in platinum-sensitive high-grade serous ovarian cancer", Cancer Chemotherapy and Pharmacology, vol. 81 (4): 647-658, Apr. 2018.
Schiewer et al., "DNA Damage Response in Prostate Cancer", Cold Spring Harbor Perspectives in Medicine, vol. 9 (1):—Jan. 2019.
Moore et al., "The effect of food on the pharmacokinetics of niraparib, a poly(ADP-ribose) polymerase (PARP) inhibitor, in patients with recurrent ovarian cancer", Cancer Chemotherapy and Pharmacology, vol. 81 (3): 497-503, Mar. 2018.
Yang et al., "Break Breast Cancer Addiction by CRISPR/Cas9 Genome Editing", Journal of Cancer, vol. 9 (2): 219-231, 2018.
Ferrara et al., "The development of PARP as a successful target for cancer therapy", Expert Review of Anticancer Therapy, vol. 18 (2): 161-175, 2018.
Liu et al., "Poly(ADP-ribose) polymerase (PARP) inhibitors and ovarian cancer", Taiwanese Journal of Obstetrics & Gynecology, vol. 56 (5): 713-714, Oct. 2017.
Caruso et al., "Niraparib in ovarian cancer: results to date and clinical potential", Therapeutic Advances in Medical Oncology, vol. 9 (9): 579-588, Sep. 2017.
Parkes et al., "Systemic Treatment Strategies for Patients with Hereditary Breast Cancer Syndromes", Oncologist, vol. 22 (6): 655-666, Jun. 2017.
Van Andel et al., "Human mass balance study and metabolite profiling of $^{14}$C-niraparib, a novel poly(ADP-Ribose) polymerase (PARP)-1 and PARP-2 inhibitor, in patients with advanced cancer", Investigational New Drugs, vol. 35 (6): 751-765, Dec. 2017.
Gadi et al., "Practical Approach to Triple-Negative Breast Cancer", Journal of Oncology Practice, vol. 13 (5): 293-+ May 2017.
Del Rivero et al., "PARP Inhibitors: The Cornerstone of DNA Repair-Targeted Therapies", Oncology-New York, vol. 31 (4): 265-273, Apr. 2017.
Kanjanapan et al., "Niraparib for the treatment of ovarian cancer", Expert Opinion on Pharmacotherapy, vol. 18 (6): 631-640, Apr. 2017.
Wilson et al., "A phase I study of intravenous and oral rucaparib in combination with chemotherapy in patients with advanced solid tumours", British Journal of Cancer, vol. 116 (7): 884-892, Mar. 28, 2017.
Xiong et al., "Pharmacogenomics of platinum-based chemotherapy in non-small cell lung cancer: focusing on DNA repair systems", Medical Oncology, vol. 34 (4):—Apr. 2017.
Jdey et al., "Drug-Driven Synthetic Lethality: Bypassing Tumor Cell Genetics with a Combination of AsiDNA and PARP Inhibitors", Clinical Cancer Research, vol. 23 (4): 1001-1011, Feb. 2017.
Brasseur et al., "Chemoresistance and targeted therapies in ovarian and endometrial cancers", Oncotarget, vol. 8 (3): 4008-4042, Jan. 17, 2017.
Yuan et al., "PARP inhibitors as antitumor agents: a patent update (2013-2015)", Expert Opinion on Therapeutic Patents, vol. 27 (3): 363-382, Mar. 2017.
Anderson et al., "Iodinated benzimidazole PARP radiotracer for evaluating PARP1/2 expression in vitro and in vivo", Nuclear Medicine and Biology, vol. 43 (12): 752-758, Dec. 2016.
Konecny et al., "PARP inhibitors for BRCA1/2-mutated and sporadic ovarian cancer: current practice and future directions", British Journal of Cancer, vol. 115 (10): 1157-1173, Nov. 8, 2016.
McLachlan et al., "The current status of PARP inhibitors in ovarian cancer", Tumori, vol. 102 (5): 433-440, Sep.-Oct. 2016.
Zhang et al., "Targeting DNA Replication Stress for Cancer Therapy", Genes, vol. 7 (8):—Aug. 2016.
Iyevleva et al., "Cytotoxic and targeted therapy for hereditary cancers", Hereditary Cancer in Clinical Practice, vol. 14:—Aug. 23, 2016.
Wallace, "New challenges for BRCA testing: a view from the diagnostic laboratory", European Journal of Human Genetics, vol. 24: S10-S18 Suppl. Sep. 1, 2016.

Sahin et al., "Genomic instability in pancreatic adenocarcinoma: a new step towards precision medicine and novel therapeutic approaches", Expert Review of Gastroenterology & Hepatology, vol. 10 (8): 893-905, Aug. 2016.
Mazzotta et al., "Nuclear PARP1 expression and its prognostic significance in breast cancer patients", Tumor Biology, vol. 37 (5): 6143-6153, May 2016.
Rodriguez-Freixinos et al., "Current and emerging treatment options in the management of advanced ovarian cancer", Expert Opinion on Pharmacotherapy, vol. 17 (8): 1063-1076, 2016.
Jenner et al., "Evaluation of rucaparib and companion diagnostics in the PARP inhibitor landscape for recurrent ovarian cancer therapy", Future Oncology, vol. 12 (12): 1439-1456, Jun. 2016.
Ledermann, "Parp inhibitors in ovarian cancer", Annals of Oncology, vol. 27: 40-44 Suppl. Apr. 1, 2016.
Wang et al., "The BRCA1-Delta 11q Alternative Splice Isoform Bypasses Germline Mutations and Promotes Therapeutic Resistance to PARP Inhibition and Cisplatin", Cancer Research, vol. 76 (9): 2778-2790, May 1, 2016.
Drew et al., "Phase 2 multicentre trial investigating intermittent and continuous dosing schedules of the poly(ADP-ribose) polymerase inhibitor rucaparib in germline BRCA mutation carriers with advanced ovarian and breast cancer", British Journal of Cancer, vol. 114 (7): 723-730, Mar. 29, 2016.
Gavande et al., "DNA repair targeted therapy: The past or future of cancer treatment?", Pharmacology & Therapeutics, vol. 160: 65-83, Apr. 2016.
McLachlan et al., "Targeted agents and combinations in ovarian cancer: where are we now?", Expert Review of Anticancer Therapy, vol. 16 (4): 441-454, Apr. 2, 2016.
Bai et al., "Genetic and epigenetic heterogeneity of epithelial ovarian cancer and the clinical implications for molecular targeted therapy", Journal of Cellular and Molecular Medicine, vol. 20 (4): 581-593, Apr. 2016.
Liu et al., "New Targeted Agents in Gynecologic Cancers: Synthetic Lethality, Homologous Recombination Deficiency, and PARP Inhibitors", Current Treatment Options in Oncology, vol. 17 (3):—Mar. 2016.
Frey et al., "Targeting DNA repair: poly (ADP-ribose) polymerase inhibitors", Translational Cancer Research, vol. 4 (1): 84-96, Feb. 2015.
Sharma et al., "BRCA-associated pancreatico-biliary neoplasms: Four cases illustrating the emerging clinical impact of genotyping", Acta Oncologica, vol. 55 (3): 377-381, Mar. 3, 2016.
Wang et al., "An overview of tyrosine kinase inhibitors for the treatment of epithelial ovarian cancer", Expert Opinion on Investigational Drugs, vol. 25 (1): 15-30, Jan. 2, 2016.
McGonigle et al., "E7449: A dual inhibitor of PARP1/2 and tankyrase1/2 inhibits growth of DNA repair deficient tumors and antagonizes Wnt signaling", Oncotarget, vol. 6 (38): 41307-41323, Dec. 1, 2015.
Walsh et al., "Leveraging DNA repair deficiency in gynecologic oncology", Current Opinion in Obstetrics & Gynecology, vol. 28 (1): 24-31, Feb. 2016.
Watson et al., "Emerging mechanisms of resistance to androgen receptor inhibitors in prostate cancer", Nature Reviews Cancer, vol. 15 (12): 701-711, Dec. 2015.
Liu et al., "Targeting tumor suppressor genes for cancer therapy", Bioessays, vol. 37 (12): 1277-1286, Dec. 2015.
Threadgill, "5-Aminoisoquinolin-1-one (5-AIQ), a Water-Soluble Inhibitor of the Poly(ADP-Ribose)Polymerases (PARPs)", Current Medicinal Chemistry, vol. 22 (33): 3807-3829, 2015.
Musella et al., "PARP inhibition: A promising therapeutic target in ovarian cancer", Cellular and Molecular Biology, vol. 61 (6): 44-61, 2015.
Livraghi et al., "PARP inhibitors in the management of breast cancer: current data and future prospects", BMC Medicine, vol. 13:—Aug. 13, 2015.
Fox et al., "The sooner the better: Genetic testing following ovarian cancer diagnosis", Gynecologic Oncology, vol. 137 (3): 423-429, Jun. 2015.
Coleman et al., "A phase II evaluation of the potent, highly selective PARP inhibitor veliparib in the treatment of persistent or recurrent epithelial ovarian, fallopian tube, or primary peritoneal cancer in

(56) References Cited

OTHER PUBLICATIONS patients who carry a germline BRCA1 or BRCA2 mutation—An NRG Oncology/Gynecologic Oncology Group study", Gynecologic Oncology, vol. 137 (3): 386-391, Jun. 2015.
Caron, "Current place of oncogenetics in the management of ovarian cancer", Gynecologie Obstetrique & Fertilite, vol. 43 (5): 335-337, May 2015 (machine translation provided).
Jones et al., "Niraparib: A Poly(ADP-ribose) Polymerase (PARP) Inhibitor for the Treatment of Tumors with Defective Homologous Recombination", Journal of Medicinal Chemistry, vol. 58 (8): 3302-3314, Apr. 23, 2015.
Naipal et al., "PARP inhibitors: the journey from research hypothesis to clinical approval", Personalized Medicine, vol. 12 (2): 139-154, 2015.
Ezzalfani et al., "The role of the expansion cohort in phase I trials in oncology: Guidelines of the phase I Hub", Bulletin Du Cancer, vol. 102 (1): 73-82, Jan. 2015 (English language abstract).
Smith et al., "Synergistic Activity of PARP Inhibition by Talazoparib (BMN 673) with Temozolomide in Pediatric Cancer Models in the Pediatric Preclinical Testing Program", Clinical Cancer Research, vol. 21 (4): 819-832, Feb. 15, 2015.
Ferraldeschi et al., "Targeting the androgen receptor pathway in castration-resistant prostate cancer: progresses and prospects", Oncogene, vol. 34 (14): 1745-1757, Apr. 2, 2015.
Garcia et al., "A Comprehensive Approach to the Identification and Management of the BRCA Patient", Obstetrical & Gynecological Survey, vol. 70 (2): 131-143, Feb. 2015.
Lord et al., "Synthetic Lethality and Cancer Therapy: Lessons Learned from the Development of PARP Inhibitors", Annual Review of Medicine, vol. 66: 455-470, 2015.
Sonnenblick et al., "An update on PARP inhibitors-moving to the adjuvant setting", Nature Reviews Clinical Oncology, vol. 12 (1): 27-41, Jan. 2015.
Chao et al., "Synergistic Loss of Prostate Cancer Cell Viability by Coinhibition of HDAC and PARP", Molecular Cancer Research, vol. 12 (12): 1755-1766, Dec. 2014.
Fang, "Development of Synthetic Lethality Anticancer Therapeutics", Journal of Medicinal Chemistry, vol. 57 (19): 7859-7873, Oct. 9, 2014.
Feng et al., "Molecular Pathways: Targeting ETS Gene Fusions in Cancer", Clinical Cancer Research, vol. 20 (17): 4442-4448, Sep. 1, 2014.
Jian et al., "Activity of CEP-9722, a poly (ADP-ribose) polymerase inhibitor, in urothelial carcinoma correlates inversely with homologous recombination repair response to DNA damage", Anti-Cancer Drugs, vol. 25 (8): 878-886, Sep. 2014.
Bridges et al., "Niraparib (MK-4827), a novel poly(ADP-Ribose) polymerase inhibitor, radiosensitizes human lung and breast cancer cells", Oncotarget, vol. 5 (13): 5076-5086, Jul. 15, 2014.
Ferrario et al., "Advances in the approach to novel drug clinical development for breast cancer", Expert Opinion on Drug Discovery, vol. 9 (6): 647-668, Jun. 2014.
Syrios et al., "Advanced Epithelial Ovarian Cancer: From Standard Chemotherapy to Promising Molecular Pathway Targets—Where Are we Now?", Anticancer Research, vol. 34 (5): 2069-2077, May 2014.
Gras, "Niraparib hydrochloride. Poly [ADP-ribose] polymerase (PARP) inhibitor, Oncolytic", Drugs of the Future, vol. 38 (10): 679-685, Oct. 2013.
Ross, M. K. et al., "Human carboxylesterases and their role in xenobiotic and endobiotic metabolism", J Biochem Mol Toxicol, vol. 21(4):187-96, (2007).
Taketani, M. et al., Carboxylesterase in the liver and small intestine of experimental animals and human. Life Sci., vol. 81(11):924-32, (2007).
Imai T. et al., "Substrate specificity of carboxylesterase isozymes and their contribution to hydrolase activity in human liver and small intestine", Drug Metab Dispos, vol. 34(10):1734-41, (2006).
Murai, J et al., Trapping of PARP1 and PARP2 by clinical PARP inhibitors, Cancer Res, vol. 72(21): 5588-5599, (2012).

Kim, G., "FDA Approval Summary: Olaparib Monotherapy in Patients with Deleterious Germline BRCA-Mutated Advanced Ovarian Cancer Treated with Three or More Lines of Chemotherapy", Clin Cancer Res., vol. 21(19), 4257-4261 (2015).
Pal, T. P.-W., BRCA1 and BRCA2 mutations account for a large proportion of ovarian carcinoma cases. Cancer, vol. 104(12), 2807-2816, (2015).
Siegel, R., "Cancer Statistics, 2014", CA Cancer J. Clin, vol. 64, pp. 9-29, (2014).
Travis, L. B., "Risk of leukemia after platinum-based chemotherapy for ovarian cancer", N. Engl J Med, vol. 340(5), pp. 351-357, (1999).
Zhang, S. R., "Frequencies of BRCA1 and BRCA2 mutations among 1,342 unselected patients with invasive ovarian cancer", Gynecologic Oncology, vol. 121(2), pp. 353-357, (2011).
National Cancer Institute, "Ovarian Epithelial, Fallopian Tube, and Primary Peritoneal Cancer Treatment (PDQ®)—Health Professional Version", [online] (retrieved on May 19, 2019]. Retrieved from the Internet: https://www.cancer.gov/types/ovarian/hp/ovarian-epithelial-treatment-pdq#section/.
National Cancer Institute, A Snapshot of Ovarian Cancer, [online] (retrieved on May. 19, 2019]. Retrieved from the Internet: https://www.cancer.gov/types/ovarian?redirect=true and https://www.cancer.gov/types/ovarian/hp/ovarian-epithelial-treatment-pdq#section/.
National Cancer Institute, Surveillance, Epidemiology, and End Results Program: Cancer Stat Facts: Ovarian Cancer, [online] (retrieved on May, 19, 2019]. Retrieved from the Internet: https://seer.cancer.gov/statfacts/html/ovary.html.
American Cancer Society, Inc. Cancer Facts & Figures, p. 18, (2016), [online] (retrieved on May 19, 2019]. Retrieved from the Internet: https://www.cancer.org/content/dam/cancer-org/research/cancer-facts-and-statistics/annual-cancer-facts-and-figures/2016/cancer-facts-and-figures-2016.pdf.
U.S. Food & Drug Administration, Drug Approval Package: Zejula (niraparib), Company: TESARO, Inc., Application No. 208447Orig1s000, Approval Date: Mar. 27, 2017, *Approval Letters*, Center for Drug Evaluation and Research [online] (retrieved on May, 19, 2019]. Retrieved from the Internet: https://www.accessdata.fda.gov/drugsatfda_docs/nda/2017/208447Orig1s000Approv.pdf.
U.S. Food & Drug Administration, Drug Approval Package: Zejula (niraparib), Company: TESARO, Inc., Application No. 208447Orig1s000, Approval Date: Mar. 27, 2017, *Printed Labeling*, Center for Drug Evaluation and Research [online] (retrieved on May, 19, 2019]. Retrieved from the Internet: https://www.accessdata.fda.gov/drugsatfda_docs/nda/2017/208447Orig1s000Lbl.pdf.
U.S. Food & Drug Administration, Drug Approval Package: Zejula (niraparib), Company: TESARO, Inc., Application No. 208447Orig1s000, Approval Date: Mar. 27, 2017, *Multi-Discipline Review/Summary, Clinical, Non-Clinical*, Center for Drug Evaluation and Research [online] (retrieved on May, 19, 2019]. Retrieved from the Internet: https://www.accessdata.fda.gov/drugsatfda_docs/nda/2017/208447Orig1s000MultidisciplineR.pdf.
U.S. Food & Drug Administration, Drug Approval Package: Zejula (niraparib), Company: TESARO, Inc., Application No. 208447Orig1s000, Approval Date: Mar. 27, 2017, *Officer/Employee List*, Center for Drug Evaluation and Research [online] (retrieved on May 19, 2019]. Retrieved from the Internet: https://www.accessdata.fda.gov/drugsatfda_docs/nda/2017/208447Orig1s000OEList.pdf.
U.S. Food & Drug Administration, Drug Approval Package: Zejula (niraparib), Company: TESARO, Inc., Application No. 208447Orig1s000, Approval Date: Mar. 27, 2017, *Chemistry Review(s)*, Center for Drug Evaluation and Research [online] (retrieved on May 19, 2019]. Retrieved from the Internet: https://www.accessdata.fda.gov/drugsatfda_docs/nda/2017/208447Orig1s000ChemR.pdf.
U.S. Food & Drug Administration, Drug Approval Package: Zejula (niraparib), Company: TESARO, Inc., Application No. 208447Orig1s000, Approval Date: Mar. 27, 2017, *Risk Assessment and Risk Mitigation Review(s)*, Center for Drug Evaluation and Research [online] (retrieved on May 19, 2019]. Retrieved from the Internet: https://www.accessdata.fda.gov/drugsatfda_docs/nda/2017/208447Orig1s000RiskR.pdf.
U.S. Food & Drug Administration, Drug Approval Package: Zejula (niraparib), Company: TESARO, Inc., Application No.

(56) References Cited

OTHER PUBLICATIONS

208447Orig1s000, Approval Date: Mar. 27, 2017, *Proprietary Name Review(s)*, Center for Drug Evaluation and Research [online] (retrieved on May 19, 2019]. Retrieved from the Internet: https://www.accessdata.fda.gov/drugsatfda_docs/nda/2017/208447Orig1s000NameR.pdf.
U.S. Food & Drug Administration, Drug Approval Package: Zejula (niraparib), Company: TESARO, Inc., Application No. 208447Orig1s000, Approval Date: Mar. 27, 2017, *Other Review(s)*, Center for Drug Evaluation and Research [online] (retrieved on May 19, 2019]. Retrieved from the Internet: https://www.accessdata.fda.gov/drugsatfda_docs/nda/2017/208447Orig1s000OtherR.pdf.
U.S. Food & Drug Administration, Drug Approval Package: Zejula (niraparib), Company: TESARO, Inc., Application No. 208447Orig1s000, Approval Date: Mar. 27, 2017, *Administration Document(s)* & Correspondence, Center for Drug Evaluation and Research [online] (retrieved on May 19, 2019]. Retrieved from the Internet: https://www.accessdata.fda.gov/drugsatfda_docs/nda/2017/208447Orig1s000Admincorres.pdf.
U.S. Food & Drug Administration, Highlights of Prescribing Information, ZEJULAT™ (niraparib) capsules, for oral use, Initial U.S. Approval: 2017, [online] (retrieved on May 19, 2019]. Retrieved from the Internet: https://www.accessdata.fda.gov/drugsatfda_docs/label/2017/2084471bl.pdf.
Pazdur, Richard, Letter from U.S. Department of Health and Human Services, U.S. Food and Drug Administration, NDA 208447, to Charles A. Miller, Vice President, Regulatory Affairs, 1000 Winter Street, Suite 3300, Waltham, MA 02541, NDA Approval, Mar. 27, 2017 [online] (retrieved on May 19, 2019]. Retrieved from the Internet: https://www.accessdata.fda.gov/drugsatfda_docs/appletter/2017/208447Orig1s000Ltr.pdf.
Bakir et al., "The molecular genetics of hereditary and sporadic ovarian cancer: implications for the future," British Medical Bulletin, 2014, 13 pages 112:57-69; doi: 10.1093/bmb/ldu034.
Kim et al., "Molecular Cell Activation of PARP-1 by snoRNAs Controls Ribosome Biogenesis and Cell Growth via the RNA Helicase DDX21" 31 pages, Sep. 19, 2019 © 2019 Elsevier Inc. https://doi.org/10.1016/j.molcel.2019.06.020.
Scott et al., "Poly (ADP-Ribose) Polymerase Inhibitors: Recent Advances and Future Development," 11 pages, American Society of Clinical Oncology, Journal of Clinical Oncology, Biology of Neoplasia, vol. 33, No. 12, Apr. 20, 2015.
Mukhopadhyay et al., "Clinicopathological Features of Homologous Recombination—Deficient Epithelial Ovarian Cancers: Sensitivity to PARP Inhibitors, Platinum, and Survival", *Cancer Res*, 72: 5675-82, 2012 (Published OnlineFirst on Oct. 11, 2012); doi:10.1158/0008-5472.CAN-12-0324.
European Search Report dated Feb. 14, 2020 for EP Application No. 17821262.7.
Zhang et al., "A genomic instability score in discriminating nonequivalent outcomes of BRCA1/2 mutations and in predicting outcomes of ovarian cancer treated with platinum-based chemotherapy." *PLoS One* 9.12 (2014).
Berge et al., "Pharmaceutical salts," J. Pharmaceutical Sciences, 1977, 66:1-19.
Bookman et al., "Evaluation of new platinum-based treatment regimens in advanced-stage ovarian cancer: a Phase III Trial of the Gynecologic Cancer Intergroup," J Clin Oncol., 2009, 27(9):1419-1425.
Du Bois et al., "2004 consensus statements on the management of ovarian cancer: final document of the 3rd International Gynecologic Cancer Intergroup Ovarian Cancer Consensus Conference (GCIG OCCC 2004)," Ann Oncol., 2005, 16 Suppl 8:viii7-viii12.
Eisenhauer, et al., "New response evaluation criteria in solid tumors: Revised RECIST guideline (version 1.1.)," Eur. J. of Cancer, 45: 228-247 (2009).
Mutch et al., "2014 FIGO staging for ovarian, fallopian tube and peritoneal cancer," Gynecol Oncol., 2014, 133(3):401-404.
Ozols et al., "Phase III trial of carboplatin and paclitaxel compared with cisplatin and paclitaxel in patients with optimally resected stage III ovarian cancer: a Gynecologic Oncology Group study," J Clin Oncol., 2003, 21(17):3194-3200.
Pfisterer et al., "Gemcitabine plus carboplatin compared with carboplatin in patients with platinum-sensitive recurrent ovarian cancer: an intergroup trial of the AGO-OVAR, the NCIC CTG, and the EORTC GCG," J Clin Oncol., 2006, 24(29):4699-4707.
Rustin et al., "Definitions for response and progression in ovarian cancer clinical trials incorporating RECIST 1.1 and CA 125 agreed by the Gynecological Cancer Intergroup (GCIG)," Int J Gynecol Cancer, 2011, 21:419-423.
Seidman et al., "'Primary peritoneal' high-grade serous carcinoma is very likely metastatic from serous tubal intraepithelial carcinoma: assessing the new paradigm of ovarian and pelvic serous carcinogenesis and its implications for screening for ovarian cancer," Gynecol Oncol., 2011, 120(3):470-473.
Siegel et al., "Cancer statistics, 2018," CA Cancer J Clin., 2018, 68(1):7-30.
Tingulstad et al., "Survival and prognostic factors in patients with ovarian cancer," Obstet Gynecol., 2003, 101(5 Pt 1):885-891.
Vergote et al., "Neoadjuvant chemotherapy or primary surgery in stage IIIC or IV ovarian cancer," N Engl J Med., 2010, 363(10):943-953.
Bryant et al., "Specific killing of BRCA2-deficient tumours with inhibitors of poly(ADP-ribose) polymerase", Letters to Nature, Apr. 2005, 434: 913-917.
Goodman, "'Breakthrough' in Recurrent Ovarian Cancer: Niraparib Extends Progression-Free Survival in Platinum-Sensitive Disease", HSP News Service, LLC., Nov. 2016, 6 pages.
Heo et al., "Niraparib: A Review in Ovarian Cancer", Targeted Oncology, Aug. 2018, 13(4):533-539.
Mateo et al., "A decade of clinical development of PARP inhibitors in perspective", Annals of Oncology, Jun. 2019, 30:1437-1447.
Mirza et al., "Niraparib Maintenance Therapy in Platinum-Sensitive, Recurrent Ovarian Cancer,", Supplementary Appendix, N Engl. J Med, Dec. 2016, 375(22):2154-2164.
Nikolaides, "PARP inhibitor approved as maintenance for recurrent ovarian cancer", Mdedge Hematology and Oncology, Mar. 27, 2017, retrieved on May 18, 2021, retrieved from URL <"https://www.mdedge.com/hematology-oncology/article/134429/gynecologic-cancer/parp-inhibitor-approved-maintenance-recurrent">, 4 pages.
PCT International Preliminary Report on Patentability in International Application No. PCT/US2017/040039, dated Jan. 1, 2019, 6 pages.
PCT International Search Report and Written Opinion in International Application No. PCT/US2020/042065, dated Oct. 14, 2020, 10 pages.
PCT International Search Report and Written Opinion in International Application No. PCT/US2017/040039, dated Sep. 22, 2017, 8 pages.
Tchounwou et al., "Advances in Our Understanding of the Molecular Mechanisms of Action of Cisplatin in Cancer Therapy", Journal of Experimental Pharmacology, 2021, 13:303-328.
U.S. Food and Drug Administration, "Lynparza® Prescribing Information", AstraZeneca Pharmaceuticals, Mar. 2021, 18 pages.
U.S. Appl. No. 16/612,363, Bobilev et al., filed Nov. 8, 2019.
AlHilli et al., "In vivo anti-tumor activity of the PARP inhibitor niraparib in homologous recombination deficient and proficient ovarian carcinoma," Gynecologic Oncology, 2016, 143: 379-388.
Ali et al., "A Combination of Targeted Therapy with Chemotherapy Backbone Induces Response in a Treatment-Resistant Triple-Negative MCL1-Amplified Metastatic Breast Cancer Patient," Case Reports in Oncology, Jan.-Apr. 2016, 9(1):112-118.
Boyer, "Medical Oncology: in Cancer A Comprehensive Clinical Guide," Harwood Academic Publishers, 2005; Chapter 6, 14 pages.
CAS No. 1613220-15-7, "Niraparib Tosylate Monohydrate," SimSon Pharma Limited, retrieved on Aug. 3, 2022, retrieved from URL<https://www.simsonpharma.com/product/niraparib-tosylate-monohydrate>, 2 pages.
ClinicalTrials.gov [online], "A Phase I/II Study of MEDI4736 in Combination With Olaparib in Patients With Advanced Solid Tumors. (MEDIOLA)," last updated Jul. 27, 2022 , retrieved from the internet Sep. 13, 2022, retrieved from URL<https://clinicaltrials.gov/ct2/history/NCT02734004?V10=View#StudyPageTop>, 5 pages.

(56) References Cited

OTHER PUBLICATIONS

Clinicaltrials.gov [online], "Phase I/II Study of the Anti-Programmed Death Ligand-1 Durvalumab Antibody (MEDI4736) in Combination with Olaparib and/or Cediranib for Advanced Solid Tumors and Advanced or Recurrent Ovarian, Triple Negative Breast, Lung, Prostate and Colorectal Cancer," NCT02484404, last updated on Jan. 26, 2023, retrieved on Sep. 11, 2023, retrieved from URL<https://classic.clinicaltrials.gov/ct2/show/NCT02484404>, 14 pages.
Doubeni et al., "Diagnosis and Management of Ovarian Cancer," American Family Physician, Jun. 1, 2016, 93(11):938-944.
Extended European Search Report and Written Opinion mailed on Feb. 11, 2021, for EP Patent Application No. 18797986.9, 16 pages.
Foley et al., "Recurrent epithelial ovarian cancer: an update on treatment," Oncology (Williston Park), Apr. 2013, 27(4):288-294.
Gonzalez-Martin et al., "Niraparib in Patients with Newly Diagnosed Advanced Ovarian Cancer," The New England Journal of Medicine, 2019, 381(25): 2391-2402.
Isnansetyo et al., "Cytotoxicity of Fucoidan from Three Tropical Brown Algae Against Breast and Colon Cancer Cell Lines, " Pharmacogn J., 2017, 9(1):14-20.
Jones et al., "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors," Journal of Medicinal Chemistry, Oct. 2009, 52(22): 7170-7185.
Kelley et al., "Targeting DNA repair pathways for cancer treatment: what's new?," Future Oncol., 2014, 10(7):1215-37.
Konstantinophulos et al., "Single-Arm Phases 1 and 2 Trial of Niraparib in Combination with Pembrolizumab in Patients With Recurrent Platinum-Resistant Ovarian Carcinoma," JAMA Oncol., 2019, 5(8):1141-49.
Konstantinopoulos et al., "Dose-finding combination study of niraparib and pembrolizumab in patients (pts) with metastatic triple-negative breast cancer (TNBC) or recurrent platinum-resistant epithelial ovarian cancer (OC) (TOPACIO/Keynote-162)", Annals of Oncology, Sep. 2017, 28(5):V406-V407.
Kummar et al., "Randomized Trial of Oral Cyclophosphamide and Veliparib in High-Grade Serous Ovarian, Primary Peritoneal, or Fallopian Tube Cancers, or BRCA-Mutant Ovarian Cancer," AACR Journals, Mar. 31, 2015, 21(7): 1574-1582.
Kuo et al., "Casuarinin from the Bark of Terminalia arjuna Induces Apoptosis and Cell Cycle Arrest in Human Breast Adenocarcinoma MCF-7 Cells," Planta Med., 2005, 71(3):237-243.
Kurman and Shih, "The Origin and Pathogenesis of Epithelial Ovarian Cancer—a Proposed Unifying Theory," Am. J. Surg. Pathol., Mar. 2010; 34(3): 433-443.
Landen et al., "Early Events in the Pathogenesis of Epithelial Ovarian Cancer," J. Clin. Oncol. 2008; 26:995-1005.
Ledermann et al., "Homologous recombination deficiency and ovarian cancer," European Journal of Cancer, Apr. 9, 2016, 60:49-58.
Ledermann et al., "Olaparib maintenance therapy in patients with platinum-sensitive relapsed serous ovarian cancer: a preplanned retrospective analysis of outcomes by BRCA status in a radomised phase 2 trial," The Lancet, 2014, 15(8):852-61.
Lee et al., "Safety and Clinical Activity of the Programmed Death-Ligand 1 Inhibitor Durvalumab in Combination with Poly (ADP-Ribose) Polymerase Inhibitor Olaparib or Vascular Endothelial Growth Factor Receptor 1-3 Inhibitor Cediranib in Women's Cancers: A Dose-Escalation, Phase I Study", Journal of Clinical Oncology, Jul. 2017, 35(19):2193-2202.
Liu et al., "Targeting tumor suppressor genes for cancer therapy," Bioessays, Dec. 2015, 37(12):1277-1286.
Liu et al., "What is the Place of PARP Inhibitors in Ovarian Cancer Treatment?," Curr Oncol Rep, 2016, 18:29, 9 pages.
Mantovani et al., "The chemokine system in cancer biology and therapy," Science Direct, Feb. 2010, 21(1):27-39.
Matulonis et al., "A phase 3 randomized double-blind trial of maintenance with niraparib versus placebo in patients with platinum-sensitive ovarian cancer (ENGOT-OV16/NOVA trial).," Journal of Clinical Oncology, 2014, 32(15):Suppl. 5625 (Abstract).
Morales et al., "Review of poly (ADP-ribose) polymerase (PARP) mechanisms of action and rationale for targeting in cancer and other diseases," Critical Reviews in Eukaryotic Gene Expression, 2014, 24(1):15-28.
PCT International Preliminary Report on Patentability in International Application No. PCT/US2018/067653, dated Jun. 30, 2020, 11 pages.
PCT International Search Report and Written Opinion in International Application No. PCT/US2018/067653, dated May 27, 2019, 18 pages.
Pop et al., "Genetic alterations in sporadic triple negative breast cancer," The Breast, Dec. 5, 2017, 38:30-38.
Robillard et al., "Abstract 3650: Preclinical evaluation of the PARP inhibitor rucaparib in combination with PD-1 and PD-L1 inhibition in a syngeneic BRCA1 mutant ovarian cancer model," Cancer Research, Jul. 1, 2017, 77(13_Supplement):3650.
Sarin et al., "Genomic instability in pancreatic adenocarcinoma: a new step towards precision medicine and novel therapeutic approaches", Expert Review of Gastroenterology & Hepatology, vol. 10 (8): 893-905, Aug. 2016.
sec.gov, [online] "Tesaro, Inc.," Jun. 27, 2012, retrieved on Mar. 13, 2023, retrieved from URL<https://www.sec.gov/Archives/edgar/data/1491576/000104746912006982/a2210096z424b4.htm>, 206 pages.
Sisay et al., "PARP inhibitors as potential therapeutic agents for various cancers: focus on niraparib and its first global approval for maintenance therapy of gynecologic cancers," Gynecologic Oncology Research and Practice, Nov. 29, 2017, 4(8):1-13.
Stolze et al., "Comparative analysis of KRAS codon 12, 13, 18, 61 and 117 mutations using human MCF10A isogenic cell lines," Science Reports, Feb. 23, 2015, 5:8535, 9 pages.
Sun et al., "Abstract A102: A comparative pharmacokinetic-pharmacodynamic-treatment study of PARP inhibitors demonstrates favorable properties for niraparib activity in preclinical tumor models," Molecular Cancer Therapeutics, Jan. 2018, 17(1 Supplement): A102.
Vela et al., "Chemokine receptor-specific antibodies in cancer immunotherapy: achievements and challenges," Frontiers in Immunology, Jan. 30, 2015, 6(12):1-15.
Yehia et al., "The Clinical Spectrum of PTEN Mutations," Annu. Rev. Med., Jan. 27, 2020, 71:103-16.
Zielinski et al., "Arzneimittel Profil Niraparib," Arzneimittel Profil Onkologie, May 31, 2019, retrieved on Feb. 23, 2022, retrieved from URL<https://media.medonline.at/2019/05/AMP_Niraparib_2019_kh_kjk_WEB.pdf>, 13 pages (with machine translation).
Dangi-Garimella, "New PARP Inhibitor, Niraparib, Approved as Maintenance Therapy for Ovarian and Other Cancers," AJMC, Mar. 28, 2017, retrieved on Oct. 26, 2023, retrieved from URL <https://www.ajmc.com/view/new-parp-inhibitor-niraparib-approved-as-maintenance-therapy-for-ovarian-and-other-cancers>, 4 pages.
Bois et al., "A phase I and pharmacokinetic study of novel taxane BMS-188797 and cisplatin in patients with advanced solid tumors," Br. J Cancer, 2006, 94(1):79-84.
Brown et al., "Combining DNA damaging therapeutics with immunotherapy: more haste, less speed", British Journal of Cancer, Nov. 9, 2017, 118 (3):312-324.
chemicalbook.com, "Niraparib tosylate," retrieved on Nov. 24, 2021, from URL<https://www.chemicalbook.com/ChemicalProductProperty_EN_CB53336280.htm>, 2 pages.
ClinicalTrials.gov [online], "A Maintenance Study with Niraparib Versus Placebo in Patients with Platinum Sensitive Ovarian Cancer," dated May 6, 2013, retrieved Nov. 24, 2021, from URL <https://clinicaltrials.gov/ct2/show/NCT01847274>, 14 pages.
ClinicalTrials.gov [online], "A Phase I/II Study of MEDI4736 in Combination with Olaparib in Patients with Advanced Solid Tumors. (MEDIOLA)," U.S. National Library of Medicine, Apr. 12, 2016, retrieved on Jul. 6, 2022, retrieved from URL<https://clinicaltrials.gov/ct2/show/NCT02734004>, 15 pages.
ClinicalTrials.gov [online], "NCT02657889: Niraparib in Combination with Pembrolizumab in Patients with Triple-negative Breast

(56) References Cited

OTHER PUBLICATIONS

Cancer or Ovarian Cancer," Oct. 27, 2021, retrieved on Nov. 28, 2022, retrieved from URL:<https://clinicaltrials.gov/ct2/show/NCT02657889>, 10 pages.
Dann et al., "BRCA 1/2 mutations and expression: response to platinum chemotherapy in patients with advanced stage epithelial ovarian cancer," Gynecol. Oncol., 2012, 125(3):677-682.
Hamanishi et al., "Immune Checkpoint Inhibition in Ovarian Cancer," International Immunology, Apr. 7, 2016, 28(7): 339-348.
Hamanishi et al., "PD1/PDL1 Blockade in Cancer Treatment: Perspectives and Issues," Int. J. Clin. Oncol., Feb. 22, 2016, 21: 462-473.
Hennessy et al., "Somatic Mutations in BRCA1 and BRCA2 Could Expand the Number of Patients That Benefit from Poly (ADP Ribose) Polymerase Inhibitors in Ovarian Cancer," J Clin Oncol. 2010, 28(22):3570-3576.
Jiao et al., "PARP inhibitor upregulates PD-L1 expression and enhances cancer-associated immunosuppression," Clinical Cancer Research, Feb. 2017, 23(14):3711-3720.
Merriam-Webster.com [online], "Deficient," Merriam-Webster dictionary, 2022, 7 pages.
Ohmoto et al., "Current status of poly(ADP-ribose) polymerase inhibitors and future directions," Onco. Targets Ther., Oct. 26, 2017, 10:5195-5208.
PCT Invitation to Pay Additional Fees in International Application No. PCT/US2018/067653, dated Apr. 2, 2019, 18 pages.
Zhu et al., "Programmed death-1 pathway blockade produces a synergistic antitumor effect: combined application in ovarian cancer," Journal of Gynecologic Oncology, Sep. 2017, 28(5):e64, 19 pages.
European Search Report in European Application No. 23211450.4, dated Feb. 15, 2024, 11 pages.
Jackson et al., "Personalised Cancer Medicine," Int. J. Cancer, Jul. 15, 2015, 137(2):262-266.
Michels et al., "Predictive biomarkers for cancer therapy with PARP inhibitors," Oncogene, Jul. 24, 2014, 33(30):3894-3907.
SRL-group.co.jp, "myChoice Diagnostic System," Jan. 4, 2021, retrieved on Jun. 3, 2024, retrieved from URL: <https://www.srl-group.co.jp/assets/pdf/news/testing/2021-01.pdf>, 4 pages (with Machine Translation).
Chemicalbook.com [online], "CAS No. 1613220-15-7—Niraparib tosylate," Sep. 18, 2016, retrieved on Nov. 24, 2021, retrieved from URL: <https://www.chemicalbook.com/ChemicalProductProperty_EN_CB53336280.htm>, 2 pages.
Feng et al., "Homologous recombination deficiency status predicts response to platinum-based chemotherapy in Chinese patients with high-grade serous ovarian carcinoma," Journal of Ovarian Research, Mar. 15, 2023, 16(53):1-11.
[No Author Listed], "Assessment report—Zejula," European Medicines Agency, Sep. 17, 2017, 122 pages.
[No Author Listed], "Dear Health Care Provider Letter (Niraparib)—Important Prescribing Information,", GSK, Nov. 2022, 3 pages.
[No Author Listed], "Medical Review 206162Orig1s000 (Olaparib)," Center for Drug Evaluation and Research, 2014, 133 pages.
Adams, "Tesaro's PARP ovarian cancer drug hits PhIII goal; prepares to file," Jun. 29, 2016, retrieved from URL <https://www.fiercebiotech.com/biotech/tesaro-s-parp-ovarian-cancer-drug-hits-phiii-goal-prepares-to-file>, 2 pages.
Akay et al., "An In-Depth Review of Niraparib in Ovarian Cancer: Mechanism of Action, Clinical Efficacy and Future Directions," Oncology and Therapy, Dec. 2021, 9:347-364.
Al Hilli et al., "Abstract PR05: In vivo antitumor activity of the PARP inhibitor niraparib (MK-4827) in homologous recombination deficient and proficient ovarian cancer," Clin Cancer Res., 2013, 19 (19_Supplement), 5 pages.
ASCOpost.com [online], "NOVA: Final Analysis Confirms No Significant Overall Survival Benefit for Maintenance Niraparib in Recurrent Ovarian Cancer," May 25, 2024, retrieved from URL <https://ascopost.com/issues/may-25-2023/nova-final-analysis-confirms-no-significant-overall-survival-benefit-for-maintenance-niraparib-in-recurrent-ovarian-cancer/>, 3 pages.
ClinicalTrials.gov [online], "NCT01847274—A Maintenance Study With Niraparib Versus Placebo in Patients With Platinum Sensitive Ovarian Cancer," version 32, May 11, 2016, retrieved from URL <https://clinicaltrials.gov/study/NCT01847274?tab=history&a=32#version-content-panel>, 11 pages.
ClinialTrials.gov [online], "Protocol of clinical trial NCT01847274—A Maintenance Study With Niraparib Versus Placebo in Patients With Platinum Sensitive Ovarian Cancer," Dec. 23, 2014, retrieved from URL <https://clinicaltrials.gov/study/NCT01847274?tab=history&a=28#version-content-panel>, 19 pages.
ClinialTrials.gov [online], "Protocol of clinical trial NCT01847274—A Maintenance Study With Niraparib Versus Placebo in Patients With Platinum Sensitive Ovarian Cancer," May 11, 2016, retrieved from URL <https://clinicaltrials.gov/study/NCT01847274?tab=history&a=32#version-content-panel>, 14 pages.
Drew, "The development of PARP inhibitors in ovarian cancer: from bench to bedside," Br. J. Cancer 2015, 113:S3-S9.
Globenewswire.com [online], "TESARO's Niraparib Significantly Improved Progression—Free Survival for Patients With Ovarian Cancer in Both Cohorts of the Phase 3 NOVA Trial," Jun. 29, 2016, retrieved from URL <https://www.globenewswire.com/news-release/2016/06/29/852247/0/en/TESARO-s-Niraparib-Significantly-Improved-Progression-Free-Survival-for-Patients-With-Ovarian-Cancer-in-Both-Cohorts-of-the-Phase-3-NOVA-Trial.html>, 3 pages.
How et al., "Modification of Homologous Recombination Deficiency Score Threshold and Association with Long-Term Survival in Epithelial Ovarian Cancer," Cancers (Basel), Feb. 24, 2021, 13(946):1-17.
Kaye, "Progress in the treatment of ovarian cancer—lessons from homologous recombination deficiency—the first 10 years," SB Annals of Oncology, Apr. 2016, 27(Supplement 1):i1-i3.
Konstantinopoulos et al., "BRCA status in epithelial ovarian cancer: implications for management and future clinical trial design," Clinical Investigation, 2013, 3(8):777-790.
Mirza et al., "Abstract 941TP: ENGOT-OV16/NOVA: A Phase 3 Randomized Double-Bline Trial of Maintenance with PARP-Inhibitor Niraparib versus Placebo in Patients with Platinum-Sensitive Ovarian Cancer," Annals of Oncology, 2014, 25 (Supplement 4), iv325,1 page.
Myriad.com [online], "myChoice HRD(TM) Test Identifies Breast Cancer Patients Likely to Respond to Platinum-Containing Therapies," Press Release Myriad genetics Press Release, Dec. 10, 2015, retrieved from URL <https://investor.myriad.com/news-releases/news-release-detail/?newsItemId=11981>, 5 pages.
Ngoi et al., "The role of homologous recombination deficiency testing in ovarian cancer and its clinical implications: do we need it?," ESMO Open, 2021, 6(3):1-12.
OncLive.com [online], "Role of PARP Inhibitors in Advanced Ovarian Cancer," May 30, 2023, retrieved from URL <https://www.onclive.com/view/role-of-parp-inhibitors-in-advanced-ovarian-cancer>, 7 pages.
OncLive.com [online], "Treatment of HRD-Negative Cancer," Oct. 24, 2019, retrieved from URL <https://www.onclive.com/view/treatment-of-hrd-negative-ovarian-cancer>, 5 pages.
Sehouli et al., "PARP Inhibitors for Recurrent Ovarian Carcinoma: Current Treatment Options and Future Perspectives," Geburtshilfe Frauenheilkd, Feb. 2016, 76(2):164-169.
Stronach et al., "Biomarker Assessment of HR Deficiency, Tumor *BRCA1/2* Mutations, and *CCNE1* Copy Number in Ovarian Cancer: Associations with Clinical Outcome Following Platinum Monotherapy," Mol Cancer Res, 2018, 16(7):1103-1111.
Symeonides et al., "Ovarian cancer molecular stratification and tumor heterogeneity: a necessity and a challange," Frontiers in Oncology, Oct. 2015, 5(229):1-5.
Telli, "PARP Inhibitors in cancer: moving beyond BRCA," The Lancet Oncology, 2011, 12:827-828.
Tesarobio.com [online], "NIRAPARIB," available on or before Jun. 22, 2016, via internet archive: Wayback Machine, retrieved from URL <https://web.archive.org/web/20160622232504/http:/www.tesarobio.com/niraparib>, 4 pages.

(56) References Cited

OTHER PUBLICATIONS

Turner et al., "A synthetic lethal siRNA screen indentifying genes mediating sensitivity to a PARP inhibitor," EMBO Journal, Apr. 2008, 27:1368-1377.

U.S. Food and Drug Administration, "Zejula (niraparib) capsules: Highlights of Prescribing Information," Dec. 2022, 32 pages.

ClinicalTrials.gov [online], "A Maintenance Study With Niraparib Versus Placebo in Patients With Platinum Sensitive Ovarian Cancer," NCT01847274, Last updated on Jun. 2, 2023, retrieved on Mar. 15, 2025, retrieved from URL <https://clinicaltrials.gov/study/NCT01847274>, 65 pages.

ClinicalTrials.gov [online], "A study of MK 4827 in combination with standard chemotherapy in participants with advanced solid tumors (MK-4827-008AM1)," NCT01110603, Last updated on May 5, 2016, retrieved on Mar. 15, 2025, retrieved from URL <https://clinicaltrials.gov/study/NCT01110603>, 19 pages.

ClinicalTrials.gov [online], "A Study of MK4827 in Participants With Advanced Solid Tumors or Hematologic Malignancies (MK-4827-001 AM8)," NCT00749502, Last updated on Jul. 25, 2013, retrieved on Apr. 15, 2025, retrieved from URL >https://clinicaltrials.gov/study/NCT00749502?term=NCT00749502&rank=1>, 39 pages.

\* cited by examiner

| END POINT | gBRCAmut | | non-gBRCAmut HRDpositive | | non-gBRCAmut OVERALL | |
|---|---|---|---|---|---|---|
| | NIRAPARIB (N=138) | PLACEBO (N=65) | NIRAPARIB (N=106) | PLACEBO (N=56) | NIRAPARIB (N=234) | PLACEBO (N=116) |
| CHEMOTHERAPY-FREE INTERVAL | | | | | | |
| MEDIAN (95% CI) — MO | 22.8 (17.9, NR) | 9.4 (7.9, 10.6) | 18.2 (14.2, 24.3) | 7.7 (6.3, 10.6) | 12.7 (11.0, 14.7) | 8.6 (6.9, 10.0) |
| P VALUE | <0.0001 | | <0.0001 | | <0.0001 | |
| HAZARD RATIO (95% CI) | 0.26 (0.169, 0.414) | | 0.31 (0.190, 0.493) | | 0.50 (0.370, 0.666) | |
| TIME TO FIRST SUBSEQUENT THERAPY | | | | | | |
| MEDIAN (95% CI) — MO | 21.0 (17.5, NR) | 8.4 (6.6, 10.6) | 15.9 (12.4, NR) | 6.0 (4.7, 9.8) | 11.8 (9.9, 13.1) | 7.2 (5.7, 8.5) |
| P VALUE | <0.0001 | | <0.0001 | | <0.0001 | |
| HAZARD RATIO (95% CI) | 0.31 (0.205, 0.481) | | 0.36 (0.232, 0.565) | | 0.54 (0.411, 0.719) | |
| PROGRESSION-FREE SURVIVAL 2 | | | | | | |
| MEDIAN (95% CI) — MO | 25.8 (20.3, NR) | 16.0 (10.8, 21.9) | 22.3 (18.6, NR) | 17.6 (11.8, NR) | 18.4 (16.0, 21.1) | 15.1 (12.2, 20.3) |
| P-VALUE | 0.0005 | | 0.0472 | | 0.0078 | |
| HAZARD RATIO (95% CI) | 0.41 (0.242, 0.687) | | 0.58 (0.340, 0.999) | | 0.64 (0.465, 0.892) | |

Figure 11

METHODS OF TREATING OVARIAN CANCER

CROSS-REFERENCE TO RELATED APPLICATIONS

The present application is a continuation of International Application No. PCT/US17/40039 filed Jun. 29, 2017; which claims priority to U.S. Provisional Application No. 62/470,141 filed Mar. 10, 2017, U.S. Provisional Application No. 62/402,427 filed Sep. 30, 2016, and U.S. Provisional Application No. 62/356,461 filed Jun. 29, 2016, the disclosures of which are hereby incorporated by reference.

BACKGROUND

Cancer is a serious public health problem, with 562,340 people in the United States of America dying of cancer in 2009 alone. American Cancer Society, Cancer Facts & Figures 2009 (available at American Cancer Society website). One of the primary challenges in cancer treatment is discovering relevant, clinically useful characteristics of a patient's own cancer and then, based on these characteristics, administering a treatment plan best suited to the patient's cancer.

Ovarian cancer is the $5^{th}$ overall cause for cancer death in women and represents 5% of all cancer deaths in women. In 2014 it is estimated that there will be 21,980 new cases of ovarian cancer and an estimated 14,270 women will die of this disease. The expected incidence of epithelial ovarian cancer in women in the United States in 2012 is approximately 22,280 (15,500 deaths) and in Europe in 2012 was estimated at 65,538 patient cases (42,704 deaths). Epithelial carcinoma makes up 85% to 90% of ovarian cancers. While historically considered to start on the surface of the ovary, new evidence suggests at least some ovarian cancer begins in special cells in a part of the fallopian tube. The fallopian tubes, small ducts that link a woman's ovaries to her uterus, are a part of a woman's reproductive system. In a normal female reproductive system, there are two fallopian tubes, one located on each side of the uterus. Cancer cells that begin in the fallopian tube may go to the surface of the ovary early on. The term 'ovarian cancer' is often used to describe epithelial cancers that begin in the ovary, the fallopian tube, and the lining of the abdominal cavity, called the peritoneum. At diagnosis, most women present with advanced disease, which accounts for the high mortality rate.

Standard therapy for advanced ovarian cancer typically consists of surgical debulking and a chemotherapy regimen. Initial chemotherapy consists of either taxane or platinum chemotherapy, or a combination thereof. While approximately 75% of patients respond to front line therapy, 70% of those patients who initially respond eventually relapse within 1 to 3 years. After relapse, patients respond moderately or poorly to subsequent chemotherapy. Additionally, intolerance to platinum agents is a clinical concern, as the risk of cumulative toxicities increases over the course of continued treatments. There is a significant unmet need due to the high recurrence rate, despite an initially high response rate. Attempts to improve the standard two-drug chemotherapy (carboplatin and paclitaxel) by adding a third cytotoxic drug (topotecan, gemcitabine, or doxil) have failed (du Bois et al, 2006 and Pfisterer et al, 2006). The great challenge for the near future will be the selection of patients with advanced ovarian cancer who will most benefit from specific targeted agents in the frontline treatment or maintenance setting. Maintenance therapy after the achievement of a response from initial chemotherapy may represent an approach to provide clinical benefit by delaying disease progression side effects, delaying the need for toxic chemotherapy and prolonging overall survival.

Poly(ADP-ribose) polymerases (PARPs) are a family of enzymes involved in various activities in response to DNA damage. PARP-1 is a key DNA repair enzyme that mediates single strand break (SSB) repair through the base excision repair (BER) pathway. PARP inhibitors have been demonstrated to selectively kill tumor cells that harbor BRCA1 and BRCA2 mutations. In addition, pre-clinical and preliminary clinical data suggest that PARP inhibitors are selectively cytotoxic for tumors with homologous recombination repair deficiency caused by dysfunction of genes other than BRCA1 or BRCA2.

SUMMARY

The present invention is based in part on the discovery that PARP inhibitors can be used to treat cancers characterized by wild type or mutant BRCA1 and/or BRCA2 ("BRCA genes"), e.g. in the absence or presence of a mutation in the BRCA genes. Accordingly, aspects of the invention relate to methods for treating cancer patients involving administration of an anti-PARP therapy to a patient independent of BRCA status or independent of the DNA repair status of the patient or cancer. In other aspects, the invention relates to methods for treating cancer patients involving administration of an anti-PARP therapy to a patient, wherein the therapy is commenced prior to determining the BRCA status or HRD status of the patient or the cancer. In other aspects, the invention relates to methods for treating cancer patients involving administration of an anti-PARP therapy to a patient, wherein the therapy is commenced in the absence of determining the BRCA status or DNA repair status of the patient or cancer. In other aspects, the invention relates to methods for treating cancer patients involving administration of an anti-PARP therapy to a patient characterized by an absence of a mutation in BRCA1 and/or BRCA2. In other aspects, the invention relates to methods for treating cancer patients involving administration of an anti-PARP therapy to a patient characterized by an absence of a mutation in a gene involved in DNA repair. In other aspects, the invention relates to methods for treating cancer patients involving administration of an anti-PARP therapy to a patient characterized by an absence of a mutation in a gene involved in homologous recombination. In aspects, the invention relates to methods for treating cancer patients involving administration of an anti-PARP therapy to a patient having a cancer characterized by an absence of a mutation in BRCA1 or BRCA2. In aspects, the invention relates to methods for treating cancer patients involving administration of an anti-PARP therapy to a patient having a cancer characterized by an absence of a mutation in a gene involved in homologous recombination.

In embodiments, the anti-PARP therapy is administered at a dose equivalent to about 100 mg, about 200 mg, or about 300 mg of niraparib or a salt or derivative thereof. In certain embodiments, the anti-PARP therapy is administered at a dose equivalent to about 100 mg of niraparib or a salt or derivative thereof. In certain embodiments, the anti-PARP therapy is administered at a dose equivalent to about 200 mg of niraparib or a salt or derivative thereof. In certain embodiments, the anti-PARP therapy is administered at a dose equivalent to about 300 mg of niraparib or a salt or derivative thereof.

In some embodiments, the anti-PARP therapy is administered in a regimen determined to achieve i) prolonged progression free survival as compared to control, ii) a reduced hazard ratio for disease progression or death as compared to control, iii) prolonged overall survival as compared to control, or iv) an overall response rate of at least 30%.

In embodiments, the anti-PARP therapy comprises administration of an agent that inhibits PARP-1 and/or PARP-2. In some embodiments, the agent is a small molecule, a nucleic acid, a polypeptide (e.g., an antibody), a carbohydrate, a lipid, a metal, or a toxin. In related embodiments, the agent is ABT-767, AZD 2461, BGB-290, BGP 15, CEP 9722, E7016, E7449, fluzoparib, INO1001, JPI 289, MP 124, niraparib, olaparib, ONO2231, rucaparib, SC 101914, talazoparib, veliparib, WW 46, or salts or derivatives thereof. In some related embodiments, the agent is niraparib, olaparib, rucaparib, talazoparib, veliparib, or salts or derivatives thereof. In certain embodiments, the agent is niraparib or a salt or derivative thereof. In certain embodiments, the agent is olaparib or a salt or derivative thereof. In certain embodiments, the agent is rucaparib or a salt or derivative thereof. In certain embodiments, the agent is talazoparib or a salt or derivative thereof. In certain embodiments, the agent is veliparib or a salt or derivative thereof.

In some embodiments, the methods prolong progression free survival as compared to control. In some embodiments, the methods reduce the hazard ratio for disease progression or death as compared to control. In some embodiments, the methods prolong overall survival as compared to control. In some embodiments, the methods achieve an overall response rate of at least 30%. In some embodiments, the methods achieve improved progression free survival 2 as compared to control. In some embodiments, the methods achieve improved chemotherapy free interval as compared to control. In some embodiments, the methods achieve improved time to first subsequent therapy as compared to control. In some embodiments, the methods achieve improved time to second subsequent therapy as compared to control. In some embodiments, the methods have been determined to not have a detrimental effect on Quality of Life as determined by FOSI and/or EQ-5D-5L. In some embodiments, the methods have been determined to not impact the effectiveness of a subsequent treatment with a chemotherapeutic agent (e.g., a platinum agent, including but not limited to, cisplatin, carboplatin, oxaliplatin, nedaplatin, triplatin tetranitrate, phenanthriplatin, picoplatin, or satraplatin.

In some embodiments, such cancers are selected from gynecologic cancers (i.e., cancers of the female reproductive system). In some embodiments, cancers of the female reproductive system include, but are not limited to, ovarian cancer, cancer of the fallopian tube(s), peritoneal cancer and breast cancer. In some embodiments, a gynecologic cancer is associated with homologous recombination repair deficiency/homologous repair deficiency ("HRD") and/or BRCA1/2 mutation(s). In some embodiments, a gynecologic cancer is platinum-sensitive. In some embodiments, a gynecologic cancer has responded to a platinum-based therapy. In some embodiments, a gynecologic cancer has developed resistance to a platinum-based therapy. In some embodiments, a gynecologic cancer has at one time shown a partial or complete response to platinum-based therapy. In some embodiments, a gynecologic cancer is now resistant to platinum-based therapy.

In certain embodiments, the cancer is ovarian cancer, cancer of the fallopian tube(s), or peritoneal cancer. In certain embodiments, the cancer is breast cancer.

In some embodiments, the cancer is a recurrent cancer.

In some embodiments, anti-PARP therapy is useful in treating cancer patients exhibiting a positive HRD status. In some embodiments, anti-PARP therapy is useful in treating cancer patients exhibiting a positive HRD status, wherein the patients are further characterized by the absence of a mutation in BRCA1 and/or BRCA2. In some embodiments, anti-PARP therapy is useful in treating cancer patients exhibiting a positive HRD status, wherein the patients are further characterized by the absence of a germline mutation in BRCA1 and/or BRCA2. In some embodiments, a positive HRD status is determined by quantifying in a patient sample a number of Indicator Chromosomal Aberration ("CA") regions. In some embodiments, a tumor sample from a patient has a positive HRD status.

In some embodiments, anti-PARP therapy is useful in treating cancer patients exhibiting an absence of a germline mutation in BRCA1 and BRCA2. In some embodiments, anti-PARP therapy is useful in treating cancer patients with platinum sensitive tumors that also exhibit an absence of a germline mutation in BRCA1 and BRCA2.

In some embodiments, anti-PARP therapy is useful in treating cancer patients exhibiting an absence of HRD. In some embodiments, anti-PARP therapy is useful in treating platinum sensitive, recurrent ovarian cancer patients, wherein the patient does not have HRD or wherein the patient is characterized by an absence of HRD. In some embodiments, the absence of HRD is further characterized by lacking "chromosomal aberrations" or "CA". CA refers to a detectable variation in a sample's chromosomal DNA. In some embodiments, CA may fall into at least one of three overlapping categories: loss of heterozygosity (LOH), allelic imbalance (e.g., telomeric allelic imbalance (TAI)), or large scale transition (LST).

Accordingly, in some embodiments, the present invention provides a method of administering anti-PARP therapy to a patient having recurrent and/or platinum sensitive cancer selected from ovarian cancer, fallopian tube cancer, or primary peritoneal cancer comprising administering anti-PARP therapy to the patient according to a regimen determined to achieve prolonged progression free survival as compared to control.

Among other things, the present invention demonstrates remarkable clinical efficacy of niraparib, for example when administered to certain patient populations (e.g., populations suffering from or susceptible to certain tumors; populations characterized by presence or level of a particular marker, such as for example HRD status and/or BRCA1/2 mutation, etc.; populations that may or may not have received or be receiving other therapy, etc.) and/or according to certain regimens. In some embodiments, the present invention provides a method of administering anti-PARP therapy to a patient having a recurrent and/or platinum sensitive cancer selected from ovarian cancer, fallopian tube cancer, or primary peritoneal cancer comprising administering anti-PARP therapy to the patient according to a regimen determined to achieve a reduced hazard ratio for disease progression or death as compared to control.

In some embodiments, the present invention provides a method of administering anti-PARP therapy to a patient having a recurrent and/or platinum sensitive cancer selected from ovarian cancer, fallopian tube cancer, or primary peritoneal cancer comprising administering anti-PARP therapy to the patient according to a regimen determined to achieve prolonged overall survival as compared to control.

In some embodiments, the present invention provides a method of administering anti-PARP therapy to a patient having a recurrent and/or platinum sensitive cancer selected from ovarian cancer, fallopian tube cancer, or primary peritoneal cancer comprising administering anti-PARP therapy to the patient according to a regimen determined to achieve an overall response rate of at least 30%. In some embodiments an overall response rate is assessed according to RECIST v1.1 guidelines.

In some embodiments, the method of administering anti-PARP therapy is according to a regimen determined to achieve prolonged progression free survival 2 as compared to control.

In some embodiments, the method of administering anti-PARP therapy is according to a regimen determined to achieve extended chemotherapy free interval as compared to control.

In some embodiments, the method of administering anti-PARP therapy is according to a regimen determined to achieve extended time to first subsequent therapy as compared to control.

In some embodiments, the method of administering anti-PARP therapy is according to a regimen determined to achieve extended time to second subsequent therapy as compared to control.

In some embodiments, the recurrent and/or platinum sensitive cancer is ovarian cancer. In some embodiments, the ovarian cancer is platinum sensitive ovarian cancer at the commencement of anti-PARP therapy administration. In some embodiments, the ovarian cancer is recurrent, platinum sensitive ovarian cancer at the commencement of anti-PARP therapy administration. In some embodiments, the ovarian cancer responded to the most recent platinum-based chemotherapy regimen prior to commencement of anti-PARP therapy administration. In some embodiments, response to the most recent platinum-based chemotherapy regimen is a complete response. In some embodiments, response to the most recent platinum-based chemotherapy regimen is a partial response. In some embodiments, the ovarian cancer responded to the penultimate platinum-based chemotherapy regimen prior to commencement of anti-PARP therapy administration.

In some embodiments, the recurrent and/or platinum sensitive cancer is fallopian tube cancer. In some embodiments, the fallopian tube cancer is platinum sensitive at the commencement of anti-PARP therapy administration. In some embodiments, the recurrent, fallopian tube cancer is platinum sensitive at the commencement of anti-PARP therapy administration. In some embodiments, the fallopian tube cancer responded to the most recent platinum-based chemotherapy regimen prior to commencement of anti-PARP therapy administration. In some embodiments, response to the most recent platinum-based chemotherapy regimen is a complete response. In some embodiments, response to the most recent platinum-based chemotherapy regimen is a partial response. In some embodiments, the fallopian tube cancer responded to the penultimate platinum-based chemotherapy regimen prior to commencement of anti-PARP therapy administration.

In some embodiments, the recurrent and/or platinum sensitive cancer is primary peritoneal cancer. In some embodiments, the primary peritoneal cancer is platinum sensitive at the commencement of anti-PARP therapy administration. In some embodiments, the recurrent, primary peritoneal cancer is platinum sensitive at the commencement of anti-PARP therapy administration. In some embodiments, the primary peritoneal responded to the most recent platinum-based chemotherapy regimen prior to commencement of anti-PARP therapy administration. In some embodiments, response to the most recent platinum-based chemotherapy regimen is a complete response. In some embodiments, response to the most recent platinum-based chemotherapy regimen is a partial response. In some embodiments, the primary peritoneal cancer responded to the penultimate platinum-based chemotherapy regimen prior to commencement of anti-PARP therapy administration.

In some embodiments, the patient has at least one mutation selected from (i) a germline mutation in BRCA1 and/or BRCA2, or (ii) a sporadic mutation in BRCA1 and/or BRCA2.

In some embodiments, the patient has a germline mutation in BRCA1 and/or BRCA2.

In some embodiments, the regimen is determined to achieve a hazard ratio for disease progression of less than about 0.5. In some embodiments, the hazard ratio for disease progression is less than about 0.4. In some embodiments, the hazard ratio for disease progression is less than about 0.3.

In some embodiments, the regimen is determined to achieve prolonged progression free survival of at least 9 months. In some embodiments, the prolonged progression free survival is at least 12 months. In some embodiments, the prolonged progression free survival is at least 15 months. In some embodiments, the prolonged progression free survival is at least 21 months.

In some embodiments, the patient has a sporadic mutation in BRCA1 or BRCA2.

In some embodiments, the patient is characterized by an absence of a germline mutation in BRCA1 or BRCA2. In some embodiments, the patient is characterized by an absence of HRD. In some embodiments, the patient is characterized by an absence of a germline mutation in BRCA1 or BRCA2 and by an absence of HRD.

In some embodiments, the patient is characterized by an absence of a sporadic mutation in BRCA1 or BRCA2. In some embodiments, the patient is characterized by an absence of HRD. In some embodiments, the patient is characterized by an absence of a sporadic mutation in BRCA1 or BRCA2 and by an absence of HRD. In some embodiments, the absence of HRD is further characterized by lacking "chromosomal aberrations" or "CA". CA refers to a detectable variation in a sample's chromosomal DNA. In some embodiments, CA may fall into at least one of three overlapping categories: loss of heterozygosity (LOH), allelic imbalance (e.g., telomeric allelic imbalance (TAI)), or large scale transition (LST).

In some embodiments, the patient is characterized by an absence of a mutation in BRCA1 or BRCA2 (e.g., lacking both germline BRCA1/2 and sporadic BRCA1/2 mutations).

In some embodiments, the patient has a tumor with a positive homologous recombination deficiency status.

In some embodiments, the present invention provides a method of administering anti-PARP therapy to a patient characterized by an absence of a germline BRCA1/2 mutation, wherein the patient has a tumor with a positive homologous recombination deficiency status.

In some embodiments, the present invention provides a method of administering anti-PARP therapy to a patient having a sporadic mutation in BRCA1 or BRCA2, wherein the patient has a tumor with a positive homologous recombination deficiency status.

In some embodiments, the present invention provides a method of administering anti-PARP therapy to a patient characterized by an absence of a mutation in BRCA1/2 (i.e., a BRCA$^{wt}$ patient), wherein the patient has a tumor with a positive homologous recombination deficiency status.

In some embodiments, the patient has a tumor with a negative homologous recombination deficiency status. In some embodiments, the patient has a tumor further characterized by being negative for germline mutations in BRCA1 or BRCA2.

In some embodiments, the present invention provides a method of administering anti-PARP therapy to a patient characterized by a germline mutation in BRCA1 or BRCA2 (gBRCA$^{mut}$) according to a regimen determined to achieve a hazard ratio for disease progression of less than about 0.4. In some such embodiments, the hazard ratio for disease progression is less than about 0.3.

In some embodiments, the present invention provides a method of administering anti-PARP therapy to a patient characterized by a germline mutation in BRCA1 or BRCA2 (gBRCA$^{mut}$) according to a regimen determined to achieve prolonged progression free survival of at least 9 months. In some such embodiments, the prolonged progression free survival is at least 12 months or at least 21 months.

In some embodiments, the present invention provides a method of administering anti-PARP therapy to a patient characterized by an absence of a germline BRCA1/2 mutation, wherein the patient has a tumor with a positive homologous recombination deficiency status, according to a regimen determined to achieve a hazard ratio for disease progression of less than about 0.5. In some such embodiments, the hazard ratio for disease progression is less than about 0.4.

In some embodiments, the present invention provides a method of administering anti-PARP therapy to a patient characterized by an absence of a germline BRCA1/2 mutation, wherein the patient has a tumor with a positive homologous recombination deficiency status, according to a regimen determined to achieve prolonged progression free survival of at least 12 months.

In some embodiments, the present invention provides a method of administering anti-PARP therapy to a patient characterized by an absence of a germline BRCA1/2 mutation according to a regimen determined to achieve a hazard ratio for disease progression of less than about 0.5.

In some embodiments, the present invention provides a method of administering anti-PARP therapy to a patient characterized by an absence of a germline BRCA1/2 mutation according to a regimen determined to achieve prolonged progression free survival of at least 9 months or at least 12 months.

In some embodiments, the present invention provides a method of administering anti-PARP therapy to a patient having a sporadic mutation in BRCA1 or BRCA2, wherein the patient has a tumor with a positive homologous recombination deficiency status, according to a regimen determined to achieve a hazard ratio for disease progression of less than about 0.4. In some embodiments, the hazard ratio for disease progression is less than about 0.3.

In some embodiments, the present invention provides a method of administering anti-PARP therapy to a patient having a sporadic mutation in BRCA1 or BRCA2, wherein the patient has a tumor with a positive homologous recombination deficiency status, according to a regimen determined to achieve prolonged progression free survival of at least 20 months.

In some embodiments, the present invention provides a method of administering anti-PARP therapy to a patient characterized by an absence of a BRCA1/2 mutation (i.e., a BRCA$^{wt}$ patient), wherein the patient has a tumor with a positive homologous recombination deficiency status, according to a regimen determined to achieve a hazard ratio for disease progression of less than about 0.5. In some embodiments, the hazard ratio for disease progression is less than about 0.4.

In some embodiments, the present invention provides a method of administering anti-PARP therapy to a patient characterized by an absence of a BRCA1/2 mutation (i.e., a BRCA$^{wt}$ patient), wherein the patient has a tumor with a positive homologous recombination deficiency status, according to a regimen determined to achieve prolonged progression free survival of at least 9 months or at least 12 months.

In some embodiments, the present invention provides a method of administering anti-PARP therapy to a patient characterized by an absence of a germline BRCA1/2 mutation, wherein the patient has a tumor with a negative homologous recombination deficiency status.

In some embodiments, the patient has high grade serous ovarian cancer or high grade predominantly serous histology ovarian cancer.

In some embodiments, the methods involve continued treatment until disease progression or unacceptable toxicity.

In some embodiments, the methods involve reducing the dose of the anti-PARP therapy in response to treatment toxicity. In some related embodiments, the methods involve reducing the dose of the anti-PARP therapy from about a dose equivalent to about 300 mg to a dose equivalent to about 200 mg.

In some embodiments, the regimen comprises a plurality of oral doses.

In some embodiments, the regimen comprises once daily (QD) dosing.

In some embodiments, the regimen comprises at least one 28 day cycle of anti-PARP therapy dosing.

In some embodiments, the oral dose is administered in one or more unit dosage forms.

In some embodiments, the one or more unit dosage forms are capsules.

In some embodiments, the oral dose is an amount of anti-PARP therapy equivalent to a range of about 5 to about 400 mg of niraparib. In some embodiments, the amount of anti-PARP therapy is equivalent to about 5, about 10, about 25, about 50, about 100, about 150, about 200, about 250, about 300, about 350, or about 400 mg of niraparib. In some embodiments, the amount of anti-PARP therapy is equivalent to about 300 mg of niraparib. In some embodiments, the amount of anti-PARP therapy is equivalent to about 200 mg of niraparib.

In some embodiments, each unit dosage form is equivalent to about 100 mg, about 200 mg, or about 300 mg of niraparib.

In some embodiments, each QD dose is equivalent to about 100 mg, about 200 mg, or about 300 mg of niraparib. In some embodiments, each QD dose is administered as three unit dosage forms equivalent to about 100 mg of niraparib.

In some embodiments, progression free survival is characterized by a complete response of one or more target tumors.

In some embodiments, progression free survival is characterized by a partial response of one or more target tumors.

In some embodiments, the patient is in a fasted state.

In some embodiments, the patient is in a fed state.

In some embodiments, the prolonged progression free survival is at least 9 months. In some embodiments, the prolonged progression free survival is at least 12 months. In some embodiments, the prolonged progression free survival is at least 18 months. In some embodiments, the prolonged progression free survival is at least 21 months. In some embodiments, the prolonged progression free survival is at least 24 months. In some embodiments, the prolonged progression free survival is at least 27 months. In some embodiments, the prolonged progression free survival is at least 30 months. In some embodiments, the prolonged progression free survival is at least 33 months. In some embodiments, the prolonged progression free survival is at least 36 months.

In some embodiments, the hazard ratio for disease progression is about 0.3. In some embodiments, the hazard ratio for disease progression is about 0.45. In some embodiments, the hazard ratio for disease progression is about 0.5. In some embodiments, the hazard ratio for disease progression is less than about 0.5. In some embodiments, the hazard ratio for disease progression is less than about 0.45. In some embodiments, the hazard ratio for disease progression is less than about 0.4. In some embodiments, the hazard ratio for disease progression is less than about 0.35. In some embodiments, the hazard ratio for disease progression is less than about 0.3.

In some embodiments, anti-PARP therapy is administered as a maintenance therapy.

In some embodiments, the anti-PARP therapy maintenance therapy has no significant impact on the efficacy of the next line of therapy (e.g., a subsequent treatment). In some embodiments, the next line of therapy is includes administration of a chemotherapeutic agent. In some embodiments, the chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

BRIEF DESCRIPTION OF THE DRAWING

FIG. 11 sets forth a table of secondary endpoints in the primary efficacy populations.

DETAILED DESCRIPTION OF CERTAIN EMBODIMENTS

Definitions

Figure 1:
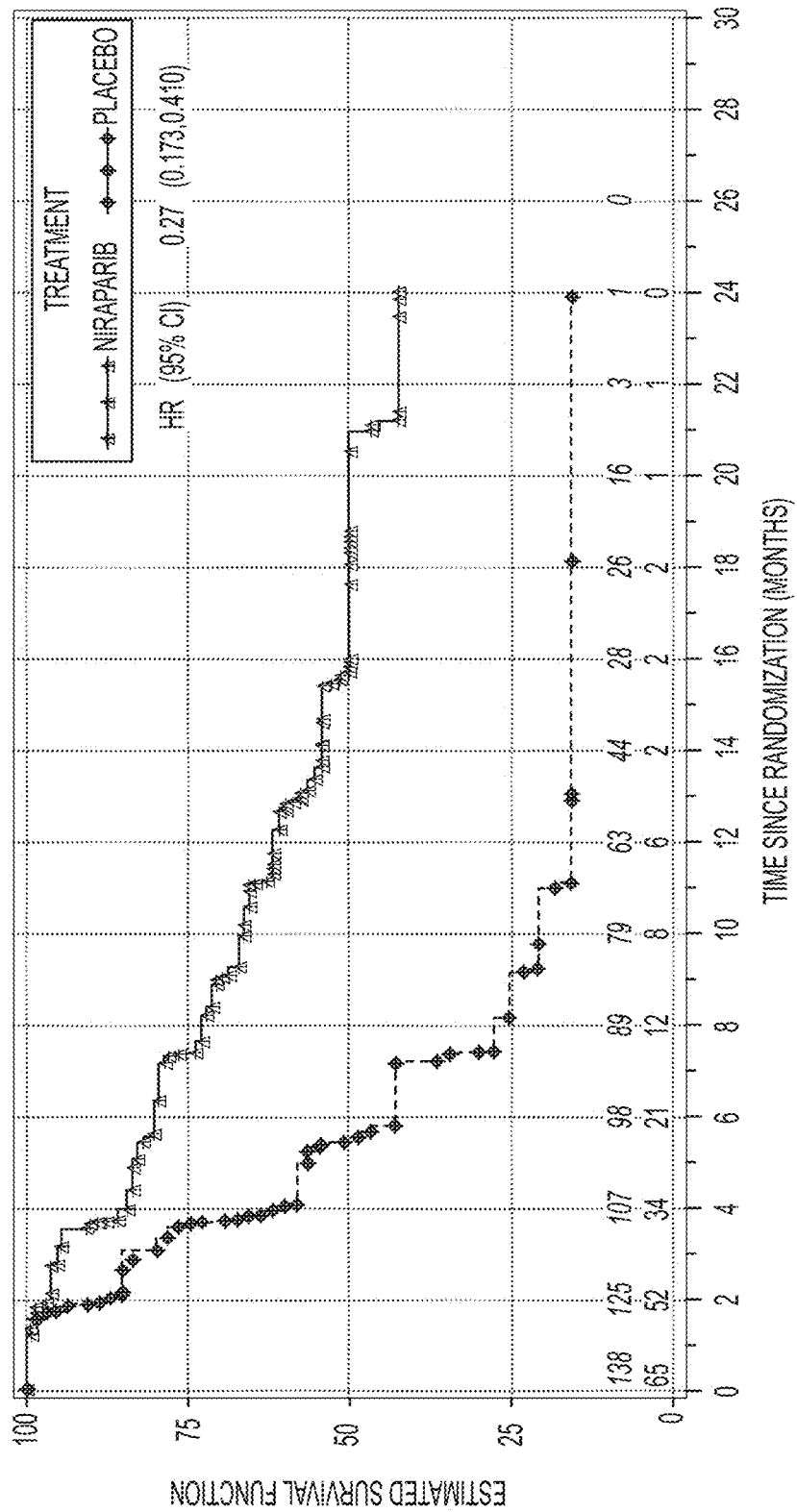
FIG. 1 relates to progression-free survival of a gBRCAmut cohort: the figure depicts a graphical representation of the progression free survival of patients harboring a genomic BRCA mutation (gBRCA$^{mut}$) when treated with niraparib or with placebo. The y-axis shows the estimated survival function value and the x-axis shows the time (in months) since randomization. The hazard ratio for disease progression is shown on the graph as HR (95% CI) 0.27 (0.173, 0.410).

As used herein, the term "administration" typically refers to the administration of a composition to a subject or system. Those of ordinary skill in the art will be aware of a variety of routes that may, in appropriate circumstances, be utilized for administration to a subject, for example a human subject. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

As used herein, the terms "dosage form" or "unit dosage form" refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a regimen that has been determined to correlate with a desired or beneficial outcome when administered to a relevant population (i.e., with a therapeutic regimen). Those of ordinary skill in the art appreciate that the total amount of a therapeutic composition or agent administered to a particular subject is determined by one or more attending physicians and may involve administration of multiple dosage forms.

As used herein, the term "regimen" refers to a set of unit doses (typically more than one) that are administered individually to a subject, typically separated by one or more periods of time. In some embodiments, a given therapeutic agent is administered according to a regimen, which may involve one or more doses. In some embodiments, a regimen comprises a plurality of doses each of which is separated in time from other doses. In some embodiments, individual doses are separated from one another by a time period of the same length; in some embodiments, a regimen comprises a plurality of doses, wherein the doses are separated by time periods of different length. In some embodiments, a regimen comprises doses of the same amount. In some embodiments, a regimen comprises doses of different amounts. In some embodiments, a regimen comprises at least one dose, wherein the dose comprises one unit dose of the therapeutic agent. In some embodiments, a regimen comprises at least one dose, wherein the dose comprises two or more unit doses of the therapeutic agent. For example, a dose of 250 mg can be administered as a single 250 mg unit dose or as two 125 mg unit doses. In some embodiments, a regimen is correlated with or result in a desired or beneficial outcome when administered across a relevant population (i.e., is a therapeutic regimen).

As used herein, the term "patient", "subject", or "test subject" refers to any organism to which provided compound or compounds described herein are administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.). In a preferred embodiment, a subject is a human. In some embodiments, a subject may be suffering from, and/or susceptible to a disease, disorder, and/or condition (e.g., cancer such as ovarian cancer, cancer of the fallopian tube(s), peritoneal cancer and breast cancer). In some embodiments, a patient is a human possessing one or more female reproductive organs. In some embodiments, a patient is a human female (i.e., a woman) that has been diagnosed with a gynecological cancer (e.g., cancer such as ovarian cancer, cancer of the fallopian tube(s), peritoneal cancer and breast cancer). As used herein, a "patient population" or "population of subjects" refers to a plurality of patients or subjects.

As used herein, a "therapeutically effective amount" refers to an amount of a therapeutic agent that produces the desired effect for which it is administered. In some embodiments, the term refers to an amount that is sufficient, when administered to a population suffering from or susceptible to a disease, disorder, and/or condition in accordance with a regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a regimen.

As used herein, a "chemotherapeutic agent" refers to a chemical agent that inhibits the proliferation, growth, lifespan and/or metastatic activity of cancer cells. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

As used herein, "CA-125" means cancer antigen 125. A CA-125 test is used to measure the amount of the protein CA-125 in the blood of a patient. A CA-125 test may be used to monitor certain cancers during and after treatment, including use to evaluate prolongation of progression free survival.

In some cases, a CA-125 test may be used to look for early signs of ovarian cancer in women with a very high risk of the disease.

As used herein, "homologous recombination" refers to a process wherein nucleotide sequences between distinct stands of DNA are exchanged. Homologous recombination is involved in a number of different biological processes, for example, homologous recombination occurs as part of the DNA repair process (e.g., doubled-strand break repair pathway and synthesis-dependent strand annealing pathway) and during process of meiosis/gametogenesis of eukaryotic organisms. As used herein, "homologous recombination deficiency," "homologous recombination repair deficiency", "homologous repair deficiency" or "HRD" refers to a reduction or impairment of the homologous recombination process. Without wishing to be bound by theory, it believed that since homologous recombination is involved in DNA repair, a homologous recombination deficient sample would be unable or have a reduced ability to repair DNA damage such as double-strand breaks. As such, a sample that is HRD would accumulate genomic errors or chromosomal aberrations can be used as a biomarker for HRD. As used herein, "chromosomal aberration" or "CA" refers to a detectable variation in a sample's chromosomal DNA. In some embodiments, CA may fall into at least one of three overlapping categories: loss of heterozygosity (LOH), allelic imbalance (e.g., telomeric allelic imbalance (TAI)), or large scale transition (LST). In some embodiments, "HRD status" is determined by the detection of CA in a sample (e.g., a tumor sample) obtained from a patient. In some embodiments, a positive HRD status refers to when a sample obtained from a patient meets a threshold number or level of CAs at a specified number of chromosomal indicator regions. In some embodiments, HRD status is determined using a commercially available diagnostic to detect chromosomal aberrations in a sample (e.g. a tumor sample) and/or to assess if a sample is unable to repair double-strand DNA breaks. Commercially available diagnostics to assess HRD status include the myChoice HRD™ diagnostic kit.

As used herein, loss of heterozygosity (LOH) refers to the change from heterozygosity to homozygosity a polymorphic loci of interest. Polymorphic loci within the human genome (e.g., single nucleotide polymorphisms (SNPs)) are generally heterozygous within an individual's germline since that individual typically receives one copy from the biological father and one copy from the biological mother. Somatically, however, this heterozygosity can change (via mutation) to homozygosity, referred to herein as LOH. LOH may result from several mechanisms. For example, in some cases, a locus of one chromosome can be deleted in a somatic cell. The locus that remains present on the other chromosome (the other non-sex chromosome for males) is an LOH locus as there is only one copy (instead of two copies) of that locus present within the genome of the affected cells. This type of LOH event results in a copy number reduction. In other cases, a locus of one chromosome (e.g., one non-sex chromosome for males) in a somatic cell can be replaced with a copy of that locus from the other chromosome, thereby eliminating any heterozygosity that may have been present within the replaced locus. In such cases, the locus that remains present on each chromosome is an LOH locus and can be referred to as a copy neutral LOH locus. LOH and its use in determining HRD is described in detail in International Application no. PCT/US2011/040953 (published as WO/2011/160063), the entire contents of which are incorporated herein by reference.

A broader class of chromosomal aberration, which encompasses LOH, is allelic imbalance. Allelic imbalance occurs when the relative copy number (i.e., copy proportion) at a particular locus in somatic cells differs from the germline. For example, if the germline has one copy of allele A and one copy of allele B at a particular locus and a somatic cell has two copies of A and one copy of B, there is allelic imbalance at the locus because the copy proportion of the somatic cell (2:1) differs from the germline (1:1). LOH is an example of allelic imbalance since the somatic cell has a copy proportion (1:0 or 2:0) that differs from the germline (1:1). But allelic imbalance encompasses more types of chromosomal aberration, e.g., 2:1 germline going to 1:1 somatic; 1:0 germline going to 1:1 somatic; 1:1 germline going to 2:1 somatic, etc. Analysis of regions of allelic imbalance encompassing the telomeres of chromosomes is particularly useful in the invention. Thus, a "telomeric allelic imbalance region" or "TAI Region" is defined as a region with allelic imbalance that (a) extends to one of the subtelomeres and (b) does not cross the centromere. TAI and its use in determining HRD is described in detail in International Application no. PCT/US2011/048427 (published as WO/2012/027224), the entire contents of which are incorporated herein by reference.

A class of chromosomal aberrations that is broader still, which encompasses LOH and TAI, is referred to herein as large scale transition ("LST"). LST refers to any somatic copy number transition (i.e., breakpoint) along the length of a chromosome where it is between two regions of at least some minimum length (e.g., at least 3, 4, 5, 6, 7, 8 9, 10, 11 12, 13, 14, 15, 16, 17, 18, 19 or 20 or more megabases) after filtering out regions shorter than some maximum length (e.g., 0.1, 0.2, 0.3, 0.4, 0.5, 0.6, 0.7, 0.8, 0.9, 1, 1.5, 2, 2.5, 3, 3.5, 4 or more megabases). For example, if after filtering out regions shorter than 3 megabases the somatic cell has a copy number of 1:1 for, e.g., at least 10 megabases and then a breakpoint transition to a region of, e.g., at least 10 megabases with copy number 2:2, this is an LST. An alternative way of defining the same phenomenon is as an LST Region, which is genomic region with stable copy number across at least some minimum length (e.g., at least 3, 4, 5, 6, 7, 8, 9, 10, 11 12, 13, 14, 15, 16, 17, 18, 19 or 20 megabases) bounded by breakpoints (i.e., transitions) where the copy number changes for another region also at least this minimum length. For example, if after filtering out regions shorter than 3 megabases the somatic cell has a region of at least 10 megabases with copy number of 1:1 bounded on one side by a breakpoint transition to a region of, e.g., at least 10 megabases with copy number 2:2, and bounded on the other side by a breakpoint transition to a region of, e.g., at least 10 megabases with copy number 1:2, then this is two LSTs. Notice that this is broader than allelic imbalance because such a copy number change would not be considered allelic imbalance (because the copy proportions 1:1 and 2:2 are the same, i.e., there has been no change in copy proportion). LST and its use in determining HRD is described in detail in Popova et al., Ploidy and large-scale genomic instability consistently identify basal-like breast carcinomas with BRCA1/2 inactivation, CANCER RES. (2012) 72:5454-5462.

As used herein, "BRCA mutation" or "mutation of BRCA" refers to a change or difference in the sequence of at least one copy of either or both of the BRCA1 or BRCA2 genes relative to an appropriate reference sequence (e.g., a wild type reference and/or a sequence that is present in non-cancerous cells in the subject). A mutation in the BRCA1/2 gene may result in a BRCA1/2 deficiency, which may include, for example a loss or reduction in the expression or function of the BRCA gene and/or encoded protein. Such mutations may also be referred to as "deleterious mutations" or may be suspected to be deleterious mutations. A BRCA mutation can be a "germline BRCA mutation," which indicates it was inherited from one or both parents. Germline mutations affect every cell in an organism and are passed on to offspring. A BRCA mutation can also be acquired during one's lifetime, i.e. spontaneously arising in any cell in the body ("soma") at any time during the patient's life, (i.e., non-inherited), which is referred to herein as a "sporadic BRCA mutation" or a "somatic BRCA mutation" interchangeably. Genetic tests are available, and known by those of skill in the art. For example, the BRACAnalysis CDx® kit is an in vitro diagnostic for detection and classification of BRCA1/2 variants. Using isolated genomic DNA, the BRACAnalysis CDx identifies mutations in the protein coding regions and intron/exon boundaries of the BRCA1 and BRCA2 genes. Single nucleotide variants and small insertions and deletions (indels) may be identified by polymerase chain reaction (PCR) and nucleotide sequencing. Large deletions and duplications in BRCA1 and BRCA2 may be detected using multiplex PCR. Indication of a "BRCA status" refers to, in at least some cases, whether a mutation is present in at least one copy of either BRCA1 or BRCA2. In some embodiments, indication of a BRCA status may refer to the mRNA expression level, methylation level or other epigenetic modification of either or both of BRCA1 and BRCA2. In some embodiments, a patient with a "positive BRCA status" refers to a patient from whom a sample has been determined to contain a mutation in BRCA1 and/or BRCA2. In some embodiments, a positive BRCA status refers to the presence of either a germline BRCA mutation (gBRCA$^{mut}$) or a somatic BRCA mutation (sBRCA$^{mut}$). In some embodiments, a patient with a "positive BRCA status" refers to a patient from whom a sample has been determined to have a reduced expression of BRCA1 and/or BRCA2. In some embodiments, BRCA status is determined for germline BRCA mutations (e.g., gBRCA$^{mut}$) and is performed on a blood sample of a subject. In some embodiments, BRCA status is determined for somatic BRCA mutations (sBRCA$^{mut}$) or total BRCA mutations (tBRCA$^{mut}$, which includes both somatic and BRCA germline mutations).

As used herein, the term "genes involved in DNA repair" means any gene involved in repair of DNA in the cell. Table 8 lists a representative set of genes involved in DNA repair. These include genes involved in homologous recombination ("HR"), which is genetic recombination in which nucleotide sequences are exchanged between two similar or identical molecules of DNA. HR is most widely used by cells to accurately repair harmful breaks that occur on both strands of DNA, known as double-strand breaks. For example, BRCA1, BRCA2, ATM, BARD1, BRIP1, CHEK2, DMC1, EME1(MMS4L), EME2, GEN1, GIYD2(SLX1B), MRE11A, MUS81, NBN, PALB2, RAD50, RAD51, RAD51B, RD51C, RAD51D, RAD52, RAD54B, RAD54L, RBBP8, SHFM1 (DSS1), XRCC2, XRCC3 are genes known to be involved in HR. One of skill in the art will be able to determine whether a gene is involved in DNA repair or homologous recombination. DNA repair status refers to the presence or absence of mutations in one or more of a gene involved in DNA repair. In certain embodiments, the invention involves use of a PARP inhibitor to treat a cancer patient regardless of DNA repair status.

As used herein, the term "PARP inhibitor" means an agent that inhibits the activity or decreases the function of any one of the poly(ADP-ribose) polymerase (PARP) family of proteins. This may include inhibitors of any one of more of the over 15 different enzymes in the PARP family, which engage in a variety of cellular functions, including cell cycle regulation, transcription, and repair of DNA damage.

As used herein, the term "progression free survival" means the time period for which a subject having a disease (e.g. cancer) survives, without a significant worsening of the disease state. Progression free survival may be assessed as a period of time in which there is no progression of tumor growth and/or wherein the disease status of a patient is not determined to be a progressive disease. In some embodiments, progression free survival of a subject having cancer is assessed by evaluating tumor (lesion) size, tumor (lesion) number, and/or metastasis.

As used herein, "progression free survival 2" (PFS2) is defined as time period from treatment randomization to the earlier date of assessment progression on the next anticancer therapy following study treatment or death by any cause. In some embodiments, determination of progression may be assessed by clinical and/or radiographic assessment.

The term "progression" of tumor growth or a "progressive disease" (PD) as used herein in reference to cancer status indicates an increase in the sum of the diameters of the target lesions (tumors). In some embodiments, progression of tumor growth refers to at least a 20% increase in the sum of diameters of target lesions, taking as reference the smallest sum on study (this includes the baseline sum if that is the smallest on study). In some embodiments, in addition to a relative increase of 20%, the sum of diameters of target lesions must also demonstrate an absolute increase of at least 5 mm. An appearance of one or more new lesions may also be factored into the determination of progression of tumor growth. Progression for the purposes of determining progression free survival may also be determined if at least one of the following criteria is met: 1) tumor assessment by CT/MRI unequivocally shows progressive disease according to RECIST 1.1 criteria; or 2) additional diagnostic tests (e.g. histology/cytology, ultrasound techniques, endoscopy, positron emission tomography) identify new lesions or determine existing lesions qualify for unequivocal progressive disease AND CA-125-progression according to Gynecologic Cancer Intergroup (GCIG)-criteria (see Rustin et al., Int J Gynecol Cancer 2011; 21: 419-423 which is incorporated herein in its entirety); 3) definitive clinical signs and symptoms of PD unrelated to non-malignant or iatrogenic causes ([i] intractable cancer-related pain; [ii] malignant bowel obstruction/worsening dysfunction; or [iii] unequivocal symptomatic worsening of ascites or pleural effusion) AND CA-125-progression according to GCIG-criteria.

As used herein, the term "partial response" or "PR" refers to a decrease in tumor progression in a subject as indicated by a decrease in the sum of the diameters of the target lesions, taking as reference the baseline sum diameters. In some embodiments, PR refers to at least a 30% decrease in the sum of diameters or target lesions, taking as reference the baseline sum diameters. Exemplary methods for evaluating partial response are identified by RECIST guidelines. See E. A. Eisenhauer, et al., "New response evaluation criteria in solid tumors: Revised RECIST guideline (version 1.1.)," *Eur. J. of Cancer*, 45: 228-247 (2009).

As used herein, "stabilization" of tumor growth or a "stable disease" (SD) refers to neither sufficient shrinkage to qualify for PR nor sufficient increase to qualify for PD. In some embodiments, stabilization refers to a less than 30%, 25%, 20%, 15%, 10% or 5% change (increase or decrease) in the sum of the diameters of the target lesions, taking as reference the baseline sum diameters. Exemplary methods for evaluating stabilization of tumor growth or a stable disease are identified by RECIST guidelines. See E. A. Eisenhauer, et al., "New response evaluation criteria in solid tumors: Revised RECIST guideline (version 1.1.)," *Eur. J. of Cancer*, 45: 228-247 (2009).

As used herein, the term "complete response" or "CR" is used to mean the disappearance of all or substantially all target lesions. In some embodiments, CR refers to an 80%, 85%, 90%, 91%, 92%, 93%, 94%, 95%, 96%, 97%, 98%, 99% or 100% decrease in the sum of the diameters of the target lesions (i.e. loss of lesions), taking as reference the baseline sum diameters. In some embodiments, CR indicates that less than 10%, 9%, 8%, 7%, 6%, 5%, 4%, 3%, 2%, 1% or less of the total lesion diameter remains after treatment. Exemplary methods for evaluating complete response are identified by RECIST guidelines. See E. A. Eisenhauer, et al., "New response evaluation criteria in solid tumors: Revised RECIST guideline (version 1.1.)," *Eur. J. of Cancer*, 45: 228-247 (2009).

As used herein, a "hazard ratio" (or "HR" when used in the context of niraparib treatment effect calculations, e.g. HR 0.38) is the expression of the hazard or chance of events occurring in the treatment arm as a ratio of the events occurring in the control arm. Hazard ratios may be determined by the Cox model, a regression method for survival data, which provides an estimate of the hazard ratio and its confidence interval. The hazard ratio is an estimate of the ratio of the hazard rate in the treated versus the control group. The hazard rate is the probability that if the event in question has not already occurred, it will occur in the next time interval, divided by the length of that interval. An assumption of proportional hazards regression is that the hazard ratio is constant over time.

In some embodiments, the present invention involves comparisons of results achieved for two or more agents, entities, situations, sets of conditions, populations etc. As will be understood by those of skill in the art, such agents, entities, situations, sets of conditions, populations, etc. can be considered "comparable" to one another when they are not identical but are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Comparisons as described herein are often made to an appropriate "reference". As used herein, the term "reference" refers to a standard or control relative to which a comparison is performed. For example, in some embodiments, an agent, animal, individual, population, sample, sequence, or value of interest is compared with a reference or control agent, animal, individual, population, sample, sequence, or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used here, the term "fasted state" refers to a state of a subject wherein food has not been consumed by the subject for a certain period of time. In some embodiments, a fasted state indicates that there is substantially no residual food in the stomach of the subject. In some embodiments, a fasted state refers to the state of the subject during the time from about 2 or more hours after food consumption up until about 30 minutes before the next food consumption. In some embodiments, the fasted state of a subject includes the time from about 2 hours after food consumption, 3 hours after food consumption, 3.5 hours after food consumption, 4 hours after food consumption, 6 hours after food consumption, 8 hours after food consumption, or 12 hours after food consumption up until about 30 minutes before the next food consumption, or any time points between, end points inclusive.

As used here, the term "fed state" refers to a state of a subject wherein there is food in the stomach of the subject at the time of administration of a therapeutic agent (e.g., niraparib). In some embodiments, a fed state refers to the state of the subject during the time from the start of food consumption to about 2 hours after food consumption, such as during food consumption, immediately after food consumption, about 30 minutes after food consumption, about 1 hour after food consumption, about 1.5 hours after food consumption, or about 2 hours after food consumption, or any time between any of the two numbers, end points inclusive. As used herein, food consumption refers to consuming a substantial amount of food, such as at least one third of a normal meal of a subject, either by volume or by total number of calories consumed.

As used herein, the term "polymorph" refers to a crystal structure of a compound. As used herein, the term "solvate" refers to a crystal form with either a stoichiometric or non-stoichiometric amount of solvent incorporated into the crystal structure. Similarly, the term "hydrate" refers to a crystal form with either a stoichiometric or non-stoichiometric amount of water incorporated into the crystal structure.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, pastes for application to the tongue. A pharmaceutical composition can also refer to a medicament.

As used herein, the term "niraparib" means any of the free base compound ((3S)-3-[4-{7-(aminocarbonyl)-2H-indazol-2-yl}phenyl]piperidine), a salt form, including pharmaceutically acceptable salts, of (3S)-3-[4-{7-(aminocarbonyl)-2H-indazol-2-yl}phenyl]piperidine (e.g., (3S)-3-[4-{7-(aminocarbonyl)-2H-indazol-2-yl}phenyl]piperidine tosylate), or a solvated or hydrated form thereof (e.g., (3S)-3-[4-{7-(aminocarbonyl)-2H-indazol-2-yl}phenyl]piperidine tosylate monohydrate). In some embodiments, such forms may be individually referred to as "niraparib free base", "niraparib tosylate" and "niraparib tosylate monohydrate", respectively. Unless otherwise specified, the term "niraparib" includes all forms of the compound (3S)-3-[4-{7-(aminocarbonyl)-2H-indazol-2-yl}phenyl]piperidine.

As used herein, the term "maintenance therapy" or "maintenance treatment" is a treatment that is given to prevent relapse of a disease. For example, a maintenance therapy may prevent or minimize growth of a cancer after it has been substantially reduced or eliminated following an initial therapy (cancer treatment). Maintenance therapy may be a continuous treatment where multiple doses are administered at spaced intervals such as every day, every other day, every week, every 2 weeks, every 3 weeks, every 4 weeks, or every 6 weeks. In some embodiments a maintenance therapy may continue for a predetermined length of time. In some embodiments, a maintenance therapy may continue until unacceptable toxicity occurs and/or disease progression occurs. In the course of maintenance treatment, treatment may be interrupted upon the occurrence of toxicity as indicated by an adverse event. If toxicity is appropriately resolved to baseline or grade 1 or less within 28 days, the patient may restart treatment with niraparib, which may include a dose level reduction, if prophylaxis is not considered feasible.

As used herein, overall survival ("OS") is defined as time from commencement of treatment to death from any cause. With respect to use as a clinical trial endpoint, it is defined as the time from randomization until death from any cause, and is measured in the intent to treat population.

As used herein, "objective response rate ("ORR") is defined as the proportion of patients with tumor size reduction of a predefined amount and for a minimum period of time. Response duration is usually measured from the time of initial response until documented tumor progression. Generally, the ORR can be defined as the sum of partial responses plus complete responses.

As used herein, "time to first subsequent therapy" (TFST) is defined as the date of randomization in the current study to the start date of the first subsequent treatment regimen (e.g., anticancer therapy).

As used herein, "time to second subsequent therapy" (TSST) is defined as the date of randomization in the current study to the start date of the second subsequent treatment regimen (e.g., anticancer therapy).

As used herein, "chemotherapy-free interval" (CFI) is defined as the time from last dose of the last anticancer therapy (e.g., platinum-based chemotherapy) until the initiation of the next Ovarian Cancer Ovarian cancer begins when healthy cells in an ovary change and grow uncontrollably, forming a mass called a tumor. A tumor can be cancerous or benign. A cancerous tumor is malignant, meaning it can grow and spread to other parts of the body. A benign tumor means the tumor can grow but will not spread. Removing the ovary or the part of the ovary where the tumor is located can treat a noncancerous ovarian tumor. An ovarian cyst, which forms on the surface of the ovary, is different than a noncancerous tumor and usually goes away without treatment. A simple ovarian cyst is not cancerous. They often occur during the normal menstrual cycle. Types of ovarian cancer include: epithelial carcinoma, germ cell tumors, or stromal tumors.

Epithelial carcinoma makes up 85% to 90% of ovarian cancers. While historically considered to start on the surface of the ovary, new evidence suggests at least some ovarian cancer begins in special cells in a part of the fallopian tube. The fallopian tubes are small ducts that link a woman's ovaries to her uterus that are a part of a woman's reproductive system. Every woman has two fallopian tubes, one located on each side of the uterus. Cancer cells that begin in the fallopian tube may go to the surface of the ovary early on. The term 'ovarian cancer' is often used to describe epithelial cancers that begin in the ovary, in the fallopian tube, and from the lining of the abdominal cavity, called the peritoneum. Germ cell tumor. This uncommon type of ovarian cancer develops in the egg-producing cells of the ovaries. This type of tumor is more common in females ages 10 to 29. Stromal tumor. This rare form of ovarian cancer develops in the connective tissue cells that hold the ovaries together, which sometimes is the tissue that makes female hormones called estrogen. Over 90% of these tumors are adult or childhood granulosa cell tumors. Granulosa cell tumors may secrete estrogen resulting in unusual vaginal bleeding at the time of diagnosis.

The expected incidence of epithelial ovarian cancer in women in the United States in 2012 is approximately 22,280 (15,500 deaths) and in Europe in 2012 was estimated at 65,538 patient cases (42,704 deaths). At diagnosis, most women present with advanced disease, which accounts for the high mortality rate. Initial chemotherapy consists of either taxane or platinum chemotherapy or a combination of both. While approximately 75% of patients respond to front line therapy 70% of those eventually relapse within 1 to 3 years. There is a significant unmet need due to the high recurrence rate, despite an initially high response rate. Attempts to improve the standard two-drug chemotherapy (carboplatin and paclitaxel) by adding a third cytotoxic drug (topotecan, gemcitabine, or doxil) have failed (du Bois et al, 2006 and Pfisterer et al, 2006). The great challenge for the near future will be the selection of patients with advanced ovarian cancer who will most benefit from specific targeted agents in the frontline maintenance setting. Maintenance therapy after the achievement of a response from initial chemotherapy may represent an approach to provide clinical benefit by delaying disease progression side effects, delaying the need for toxic chemotherapy and prolonging overall survival. However there is currently no widely accepted standard of care in the ovarian cancer maintenance setting.

The lack of successful treatment strategies led the Cancer Genome Atlas (TCGA) researchers to comprehensively measure genomic and epigenomic abnormalities on clinically annotated HGS-OvCa samples to identify molecular factors that influence pathophysiology affect outcome and constitute therapeutic targets (TCGA, 2011). Ovarian tumors are characterized by deficiencies in DNA repair such as BRCA mutations. BRCA 1 and 2 were initially identified as tumor suppressor genes that were associated with increased incidence of certain malignancies when defective, including ovarian cancer. BRCA deficiency was noted in 34% of ovarian cancers, owing to a combination of germline and sporadic mutations and promoter hypermethylation. BRCA plays a key role in DNA repair, including homologous recombination. This study estimated over half of high grade serous ovarian cancer suffered from defects in DNA repair. Tumor cells with BRCA deficiency/Homologous Recombination Deficiency (HRD) may provide an opportunity for therapeutic intervention with agents that inhibit DNA repair pathways and exploit synthetic lethality mechanisms of cancer treatment. Recent studies have suggested that HR deficiency in epithelial ovarian cancer (EOC) is not solely due to germline BRCA1 and BRCA2 mutations (Hennessy, 2010; TCGA, 2011; Byler Dann, 2012). The Cancer Genome Atlas Research Network reported a defect in at least one HR pathway gene in approximately half of the ~500 EOC in the data set.

Role of Poly(ADP-Ribose) Polymerases (PARPs)

Poly(ADP-ribose) polymerases (PARPs) are a family of enzymes that cleave NAD+, releasing nicotinamide, and successively add ADP-ribose units to form ADP-ribose polymers. Accordingly, activation of PARP enzymes can lead to depletion of cellular NAD+ levels (e.g., PARPs as NAD+ consumers) and mediates cellular signaling through ADP-ribosylation of downstream targets. PARP-1 is a zinc-finger DNA-binding enzyme that is activated by binding to DNA double or single strand breaks. It was known that anti-alkylating agents could deplete the NAD+ content of tumor cells, and the discovery of PARPs explained these phenomena. (Parp Inhibitors and Cancer Therapy. Curtin N. in Poly ADP Ribosylation. ed. Alexander Burke, Lands Bioscience and Springer Bioscience, 2006: 218-233). Anti-alkylating agents induce DNA strand breaks, which activates of PARP-1, which is part of the DNA repair pathway. Poly ADP-ribosylation of nuclear proteins by PARP-1 converts DNA damage into intracellular signals that can either activate DNA repair (e.g. by the base excision repair (BER) pathway); or trigger cell death in the presence of DNA damage that is too extensive and cannot be efficiently repaired.

The role of PARP enzymes in DNA damage response (e.g. repair of DNA in response to genotoxic stress) has led to the compelling suggestion that PARP inhibitors may be useful anti-cancer agents. Numerous studies are directed to investigating of the activity of PARP inhibitors, alone or in combination with other agents, as cancer therapeutics. PARP inhibitors may be particularly effective in treating cancers resulting from germ line or sporadic deficiency in the homologous recombination DNA repair pathway, such as BRCA-1, BRCA-2, and/or ATM deficient cancers. Additionally, simultaneous administration of genotoxic chemotherapy with PARP inhibition may enhance the killing effect of such chemotherapy by suppressing BER.

Pre-clinical ex vivo and in vivo experiments suggest that PARP inhibitors are selectively cytotoxic for tumors with homozygous inactivation of either the BRCA-1 or BRCA-2 genes, which are known to be important in the homologous recombination (HR) DNA repair pathway. The biological basis for the use of PARP-1 inhibitors as single agents in cancers with defects in HR is the requirement of PARP-1 and PARP-2 for base excision repair (BER) of the damaged DNA. Upon formation of single-strand DNA breaks, PARP-1 and PARP-2 bind at sites of lesions, become activated, and catalyze the addition of long polymers of ADP-ribose (PAR chains) on several proteins associated with chromatin, including histones, PARP itself, and various DNA repair proteins. This results in chromatin relaxation and fast recruitment of DNA repair factors that access and repair DNA breaks. Normal cells repair up to 10,000 DNA defects daily and single strand breaks are the most common form of DNA damage. Cells with defects in the BER pathway enter S phase with unrepaired single strand breaks. Pre-existing single strand breaks are converted to double strand breaks as the replication machinery passes through the break. Double strand breaks present during S phase are preferentially repaired by the error-free HR pathway. Cells unable to use HR (i.e., due to inactivation of genes required for HR, such as BRCA-1 or BRCA-2) accumulate stalled replication forks during S phase and may use error-prone non-homologous end joining (NHEJ) to repair damaged DNA. Both the inability to complete S phase (because of stalled replication forks) and error-prone repair by NHEJ, are thought to contribute to cell death.

Without wishing to be bound by theory, it is hypothesized that treatment with PARP inhibitors represents a novel opportunity to selectively kill a subset of cancer cells with deficiencies in DNA repair pathways. For example, a tumor arising in a patient with a germline BRCA mutation has a defective homologous recombination DNA repair pathway and would be increasingly dependent on BER, a pathway blocked by PARP inhibitors, for maintenance of genomic integrity. Non-BRCA deficiencies in homologous recombination DNA repair genes could also enhance tumor cell sensitivity to PARP inhibitors. This concept of inducing death by use of PARP inhibitors to block one DNA repair pathway in tumors with pre-existing deficiencies in a complementary DNA repair pathways is called synthetic lethality.

Germline mutations of BRCA-1 and BRCA-2 genes are found in a majority of patients with an inherited breast or ovarian cancer. Inactivation of BRCA-1 and BRCA-2 gene by other mechanisms, including somatic BRCA-1/2 mutations and/or gene silencing by promoter hypermethylation, occurs in a significant portion of several sporadic cancers. In particular, for ovarian cancer, somatic BRCA-1 or BRCA-2 mutations are found in 10%-15% of all epithelial ovarian carcinomas (EOCs), and strongly reduced expression of BRCA-1 has been observed in a significant portion of sporadic ovarian cancers. Collectively, up to 40%-60% of ovarian cancers might be responsive to PARP inhibitors as a consequence of defects in the BRCA-HR pathway, indicating a great potential for this approach in the therapy of ovarian cancer.

HR is a complex pathway, and several genes other than BRCA-1 and BRCA-2 are required either to sense or repair DNA double strand breaks via the HR pathway. Not surprisingly, therefore, PARP inhibitors are also selectively cytotoxic for cancer cells with deficiencies in DNA repair-proteins other than BRCA-1 and BRCA-2 including RecA homologs (RAD51 and RAD54), X-ray repair complementing defective repair in Chinese hamster cells (XRCC2 and XRCC3), DSS1, replication protein A1 (RPA1), ataxia telangiectasia mutated (ATM), ATM and Rad3-related (ATR), check point kinases (CHK1, CHK2), Nijmegen breakage syndrome 1 (NBS1), and the components of the Fanconi anemia repair pathway. Some of these genes are known to be mutated or down-regulated in different sporadic tumors, which might therefore be "addicted" to HR- but possibly also non-HR mediated DNA repair and therefore respond to PARP inhibitors. More recently, it has been also demonstrated that tumor cells with deletion of the PTEN-gene are indeed sensitive to PARP inhibitors, possibly as a consequence of HR defects.

The therapeutic potential of PARP inhibitors is further expanded by the observation that PARP-1 inhibitors not only have monotherapy activity in HR-deficient tumors, but are also effective in preclinical models in combination with cisplatin, carboplatin, alkylating and methylating agents, radiation therapy, and topoisomerase I inhibitors. In contrast to the rationale for monotherapy in which PARP inhibition alone is sufficient for cell death in HR-deficient cancers (due to endogenous DNA damage), PARP is required for repair of DNA damage induced by standard cytotoxic chemotherapy. In some cases, the specific role of PARP is not known, but PARP-1 is known to be required to release trapped topoisomerase I/irinotecan complexes from DNA. Temozolomide-induced DNA damage is repaired by the BER pathway, which requires PARP to recruit repair proteins. Combination therapies that enhance or synergize with cytotoxic agents without significantly increasing toxicity would provide substantial benefit to ovarian as well other types of cancer patients.

Treatment with PARP inhibitors (e.g., PARP-1/2 inhibitors) represents a novel opportunity to selectively kill a subset of cancer cell types by exploiting their deficiencies in DNA repair. Human cancers exhibit genomic instability and an increased mutation rate due to underlying defects in DNA repair. These deficiencies render cancer cells more dependent on the remaining DNA repair pathways and targeting these pathways is expected to have a much greater impact on the survival of the tumor cells than on normal cells. While PARP inhibitors represent a promising class of potential cancer therapeutics, the clinical efficacy of these compounds is unclear. Specifically, results regarding the clinical outcomes of different PARP inhibitors (e.g., PARP-1/2 inhibitors) as cancer therapeutics are in some cases unclear and potentially even conflicting. For example, an analysis of results of clinical trials testing the PARP inhibitor olaparib have shown conflicting long term outcomes for overall survival in patients with ovarian cancer. For example, an analysis of three clinical trials found that while on average olaparib, when added to a conventional treatment, slowed the progression of platinum-sensitive epithelial ovarian cancer in women with germline BRCA mutations compared with placebo or no-treatment, there was, however, no significant change observed in the overall survival of patients. Further, olaparib trials found that serious adverse events were more common in the olaparib group compared to the control group. See, Wiggins et al., (2015) "Poly(ADP-ribose) polymerase (PARP) inhibitors for the treatment of ovarian cancer." Cochrane Database of Systematic Reviews, Issue 5. Art. No.: CD007929. Another clinical trial with the PARP inhibitor veliparib had a relatively small sample size, and was unable to show any effect of veliparib on the progression of ovarian cancer. Thus, the art has failed to establish clinical efficacy for these PARP inhibitors and there remains a continuing need to identify, characterize, and/or develop PARP inhibitors as effective cancer therapeutics. The present disclosure satisfies this need. Among other things, the present disclosure provides niraparib compositions and methodologies that achieve effective cancer treatment, in particular as therapy for cancers of the female reproductive system (e.g. ovarian cancer). In some embodiments, the present disclosure provides niraparib compositions and/or methods that achieve progression-free survival rates and/or hazard ratios as described herein. In some embodiments, provided compositions and/or methods achieve such effects with an overall treatment emergent adverse event rate (TEAE) that is not more than about three times, or in some embodiments two times, higher than that observed with comparable placebo treatment. provided compositions and/or methods achieve such effects with a serious TEAE rate that is not more than about 5 times, or about 4.5 times, or about 4 times higher than that observed with comparable placebo treatment.

Platinum-sensitive, recurrent ovarian cancer remains an unmet medical need. Both the National Comprehensive Cancer Network (NCCN) and the European Society of Medical Oncology (ESMO) guidelines recommend re-treatment of patients with a platinum-based combination chemotherapy when relapse occurs >6 months after response to an initial platinum-based treatment. Paclitaxel plus carboplatin is the most frequently used regimen for platinum-sensitive patients who have recurred. Most patients who recur and are treated with a second round of platinum-based chemotherapy do not receive any type of treatment after response to the chemotherapy as there is no approved product for maintenance use after chemotherapy in the US. The standard of care in the US is "watchful waiting."

Unfortunately, the utility of platinum-based chemotherapy diminishes over time; the PFS and platinum-free intervals generally become shorter after each subsequent treatment with tumors ultimately becoming platinum resistant or refractory. Furthermore, patients generally do not receive more than 6 cycles of platinum-based chemotherapy per treatment course due to cumulative toxicities with platinum agents and taxanes. New agents are needed to prolong the response to platinum-based chemotherapy, reduce the risk of recurrence or death, and increase the platinum-free interval.

The poly(ADP-ribose) polymerase (PARP) family of proteins consists of over 15 different enzymes, which engage in a variety of cellular functions, including cell cycle regulation, transcription, and repair of DNA damage. BRCA1, BRCA2 and PALB2 are proteins that are important for the repair of double-strand DNA breaks by the error-free homologous recombinational repair, or HRR, pathway. When the gene for either protein is mutated, the change can lead to errors in DNA repair that can eventually cause cancer, including for example, breast or ovarian cancers.

PARP-1 is the most abundant and best characterized protein in this group and is critical to the repair of single-strand DNA breaks through the base excision repair pathway. If such breaks persist unrepaired until DNA is replicated (which must precede cell division), then the replication itself can cause double strand breaks to form. Effective inhibition of PARP-1 leads to the accumulation of single-strand breaks, which ultimately results in double-strand breaks. Usually such double-strand breaks are repaired by homologous recombination (HR), but in cells with defective HR, PARP inhibition can result in chromosomal instability, cell cycle arrest, and subsequent apoptosis. DNA is damaged thousands of times during each cell cycle, and that damage must be repaired. When subjected to enough damage at one time, the altered gene can cause the death of the cells. Normal cells that don't replicate their DNA as often as cancer cells, and that lack any mutated BRCA1 or BRCA2 still have homologous repair operating, which allows them to survive the inhibition of PARP. PARP inhibitors function by blocking PARP enzyme activity, which prevents the repair of DNA damage and ultimately may cause cell death. They also are believed to function by localizing PARP proteins at sites of DNA damage, which has relevance to their anti-tumor activity. The trapped PARP protein-DNA complexes are highly toxic to cells because they block DNA replication.

PARP proteins are typically released from DNA once the DNA binding and repair process is underway. There is evidence to demonstrate that, when the proteins are bound to PARP inhibitors, they become trapped on DNA. The trapped PARP-DNA complexes are more toxic to cells than the unrepaired single-strand DNA breaks that accumulate in the absence of PARP activity. Therefore, without being limited as to theory, there are at least two mechanisms of PARP inhibitor-inhibition of repair and PARP trapping.

The inability of HR to correct double-stranded breaks has been observed in tumors with mutations in the breast cancer-related genes BRCA1 and BRCA2, which code for proteins essential for normal HR function. The use of small-molecule PARP inhibitors to exploit this genetic vulnerability in DNA damage repair is an example of synthetic lethality, in which the simultaneous inhibition of two pathways leads to cell death, whereas blocking either pathway alone is not lethal. Encouraging preclinical results for PARP inhibitors in the treatment of BRCA-mutated tumor cells provided strong rationale for the clinical testing of these agents in patient populations most likely to carry these mutations, such as those with breast or ovarian cancer. This therapeutic strategy has now been validated by the recent US Food and Drug Administration (FDA)-accelerated approval for the PARP inhibitors olaparib and rucaparib as monotherapies to treat patients with BRCA-mutated advanced ovarian cancer. Surprisingly, the instant invention demonstrates that PARP inhibition is effective in prolonging progression free survival in human cancer patients regardless of the presence or absence of a mutation in BRCA1 or BRCA2. Niraparib is the first PARP inhibitor to demonstrate this ability, but the result can be achieved with other PARP inhibitors. Niraparib and other such PARP inhibitors are discussed below.

Niraparib, (3S)-3-[4-{7-(aminocarbonyl)-2H-indazol-2-yl}phenyl]piperidine, is an orally available, potent, poly (adenosine diphosphate [ADP]-ribose) polymerase (PARP)-1 and -2 inhibitor. See WO 2008/084261 (published on Jul. 17, 2008) and WO 2009/087381 (published Jul. 16, 2009), the entirety of each of which is hereby incorporated by reference. Niraparib can be prepared according to Scheme 1 of WO 2008/084261.

In some embodiments, niraparib can be prepared as a pharmaceutically acceptable salt. One of skill in the art will appreciate that such salt forms can exist as solvated or hydrated polymorphic forms. In some embodiments, niraparib is prepared in the form of a hydrate.

In certain embodiments, niraparib is prepared in the form of a tosylate salt. In some embodiments, niraparib is prepared in the form of a tosylate monohydrate.

The crystalline tosylate monohydrate salt of niraparib is being developed as a monotherapy agent for tumors with defects in the homologous recombination (HR) deoxyribonucleic acid (DNA) repair pathway and as a sensitizing agent in combination with cytotoxic agents and radiotherapy.

Niraparib is a potent and selective PARP-1 and PARP-2 inhibitor with inhibitory concentration at 50% of control ($IC_{50}$)=3.8 and 2.1 nM, respectively, and is at least 100-fold selective over other PARP-family members. Niraparib inhibits PARP activity, stimulated as a result of DNA damage caused by addition of hydrogen peroxide, in various cell lines with an $IC_{50}$ and an inhibitory concentration at 90% of control ($IC_{90}$) of about 4 and 50 nM, respectively.

Niraparib demonstrates selective anti-proliferative activity for cancer cell lines that have been silenced for BRCA-1 or BRCA-2, or carry BRCA-1 or BRCA-2 mutations compared to their wild type counterparts. The antiproliferative activity of niraparib on BRCA-defective cells is a consequence of a cell cycle arrest in G2/M followed by apoptosis. Niraparib is also selectively cytotoxic for selected Ewing's sarcoma, acute lymphocytic leukemia (ALL), non-small cell lung cancer (NSCLC), and small cell lung cancer (SCLC) cell lines, as well as for tumor cell lines carrying homozygous inactivation of the ATM gene. Niraparib demonstrates weak activity on normal human cells. In vivo studies demonstrated strong antitumor activity with BRCA-1 mutant breast cancer (MDA-MB-436), BRCA-2 mutant pancreatic cancer (CAPAN-1), ATM-mutant mantle cell lymphoma (GRANTA-519), serous ovarian cancer (OVCAR3), colorectal cancer (HT29 and DLD-1), patient derived Ewing's sarcoma, and TNBC xenograft models in mice.

Target engagement has also been demonstrated by measuring PARP activity in tumor homogenates from tumor xenograft studies. Inhibition of PARP activity has also been measured in peripheral blood mononuclear cells (PBMCs) from mice dosed with niraparib. Niraparib has been shown to induce cell cycle arrest, particularly arrest in the G2/M phase of the cell cycle. Accordingly, in some embodiments, the present invention provides a method of inducing cell cycle arrest of a tumor cell, the method comprising administering niraparib to a patient in need thereof. In some embodiments, the present invention provides a method of inducing arrest of the G2/M phase of the cell cycle of a tumor cell, the method comprising administering niraparib to a patient in need thereof. In some embodiments, the present invention provides a method of inducing arrest in the G2/M phase of the cell cycle of BRCA-1 and/or BRCA-2-deficient cells, the method comprising administering niraparib to a patient in need thereof.

Olaparib acts as an inhibitor of the enzyme poly ADP ribose polymerase (PARP), and is termed a PARP inhibitor. The chemical name is 4-[(3-{[4-(cyclopropylcarbonyl)piperazin-1-yl]carbonyl}-4-fluorophenyl)methyl]phthalazin-1 (2H)-one. Clinical trials of olaparib were initiated in breast, ovarian and colorectal cancer. Preliminary activity was seen in ovarian cancer, with 7 responses in 17 patients with BRCA1 or BRCA2 mutations and 11 responses in the 46 who did not have these mutations. However, an interim analysis of a phase II study that looked at using olaparib to maintain progression free survival or response after success with platinum-based chemotherapy indicated that a reported progression-free survival benefit was unlikely to translate into an overall survival benefit for the intent to treat populations. However, planned analysis of the subset of patients who had BRCA mutations found a clear advantage with olaparib (Ledermann et al., New England Journal of Medicine, 366; 15 (2012); Lancet Oncol. 15 (8): 852-61). Olaparib is approved as monotherapy, at a recommended dose of 400 mg taken twice per day, in germline BRCA mutated (gBRCAmut) advanced ovarian cancer that has received three or more prior lines of chemotherapy. BRCA1/2 mutations may be genetically predisposed to development of some forms of cancer, and may be resistant to other forms of cancer treatment. However, these cancers sometimes have a unique vulnerability, as the cancer cells have increased reliance on PARP to repair their DNA and enable them to continue dividing. This means that drugs which selectively inhibit PARP may be of benefit if the cancers are susceptible to this treatment. Thus, the olaparib clinical data demonstrated that PARP inhibitors would not be beneficial to prolong progression free survival in the treatment of cancer characterized by the absence of mutations in BRCA1 or BRCA2.

Similarly, rucaparib acts as an inhibitor of the enzyme poly ADP ribose polymerase (PARP), and is also termed a PARP inhibitor. The chemical name is 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl)methanesulfonic acid salt. It is also approved as indicated as monotherapy for the treatment of patients with deleterious BRCA mutation (germline and/or somatic) associated advanced ovarian cancer who have been treated with two or more chemotherapies. The efficacy of rucaparib was investigated in 106 patients in two multi-center, single-arm, open-label clinical trials, Study 1 and Study 2, in patients with advanced BRCA-mutant ovarian cancer who had progressed after 2 or more prior chemotherapies. All 106 patients received rucaparib 600 mg orally twice daily as monotherapy until disease progression or unacceptable toxicity. Response assessment by independent radiology review was 42% (95% CI [32, 52]), with a median DOR of 6.7 months (95% CI [5.5, 11.1]). Investigator-assessed ORR was 66% (52/79; 95% CI [54, 76]) in platinum-sensitive patients, 25% (5/20; 95% CI [9, 49]) in platinum-resistant patients, and 0% (0/7; 95% CI [0, 41]) in platinum-refractory patients. ORR was similar for patients with a BRCA1 gene mutation or BRCA2 gene mutation. Thus, the rucaparib clinical data demonstrated that PARP inhibitors would not be beneficial to prolong progression free survival in the treatment of cancer characterized by the absence of mutations in BRCA1 or BRCA2.

Similarly, talazoparib acts as an inhibitor of the enzyme poly ADP ribose polymerase (PARP), and is also termed a PARP inhibitor. It is currently being evaluated in clinical studies for the treatment of patients with gBRCA mutated breast cancer (i.e., advanced breast cancer in patients whose BRCA genes contain germline mutations). The primary objective of the study is to compare PFS of patients treated with talazoparib as a monotherapy relative to those treated with protocol-specified physicians' choice.

Similarly, veliparib acts as an inhibitor of the enzyme poly ADP ribose polymerase (PARP), and is also termed a PARP inhibitor. The chemical name of veliparib is 2-[(R)-2-methylpyrrolidin-2-yl]-1H-benzimidazole-4-carboxamide.

At diagnosis of ovarian cancer, most women present with advanced disease, which accounts for the high mortality rate. Patients with stage 2, 3 or 4 disease will undergo tumor reductive surgery if the disease is potentially resectable and may undergo subsequent chemotherapy for 4-8 cycles. Initial chemotherapy may consist of either IV chemotherapy or a combination of IV and intraperitoneal (IP) chemotherapy. IV chemotherapy usually consists of a taxane (paclitaxel or docetaxel) and a platinum (cisplatin or carboplatin). Approximately 75% of patients respond to front line therapy and are considered platinum sensitive, standardly defined as a minimum duration of 6 months following treatment with no relapse or disease progression. However, up to 70% of patients eventually relapse within 1 to 3 years. Attempts to improve the standard platinum based two-drug chemotherapy by adding a third cytotoxic drug have failed to affect either progression-free survival or overall survival and resulted in an increase in toxic effects (du Bois et al, 2006 and Pfisterer, 2006 et al). There is a high unmet need due to the high recurrence rate, even after an initially high response rate.

The Cancer Genome Atlas (TCGA) researchers tested clinically annotated HGS-OvCa samples to identify molecular factors that influence pathophysiology, affect outcome and constitute therapeutic targets (TCGA, 2011). Ovarian tumors are characterized by deficiencies in DNA repair such as BRCA mutations. BRCA 1 and 2 have been identified as tumor suppressor genes that were associated with increased incidence of certain malignancies when defective, including ovarian cancer. BRCA plays a key role in DNA repair, including homologous recombination. Tumor cells with BRCA deficiency/Homologous Recombination Deficiency (HRD) are particularly sensitive to DNA damage. Niraparib inhibits PARP activity, stimulated as a result of DNA damage and demonstrates selective anti-proliferative activity for cancer cell lines that have been silenced for BRCA1 or BRCA2, or carry BRCA-1 or BRCA-2 mutations compared to their wild type counterparts. The antiproliferative activity of niraparib on BRCA-defective cells is a consequence of a cell cycle arrest in G2/M followed by apoptosis. PARP inhibitors block alt-NHEJ and BER, forcing tumors with BRCA deficiencies to use the error-prone NHEJ to repair double strand breaks. Non-BRCA deficiencies in homologous recombination DNA repair genes could also enhance tumor cell sensitivity to PARP inhibitors. PARP inhibitors including niraparib is useful for treating individuals with tumors bearing mutations in DNA repair pathways, including those with germline BRCA mutations (gBRCAmut) who develop ovarian cancer.

In an attempt to address the high recurrence rates, anti-PARP therapy may be administered as a maintenance therapy in patients with recurrent and/or platinum sensitive ovarian cancer, including fallopian and peritoneal cancers, as an approach to prolong the initially high response rates associated with frontline platinum chemotherapy, wherein said administration prolongs progression-free survival and/or prolongs overall survival. Such a prolongation of progression free survival may result in a reduced hazard ratio for disease progression or death. Prolonged progression free survival has the potential to provide clinical benefit in several ways, including delay of disease symptoms, delay in toxicity burden of chemotherapy, and delay in quality of life deterioration. In another embodiment, the patients with platinum sensitive ovarian cancer are further characterized as having a BRCA deficiency and/or HRD (e.g. a positive HRD status). In another embodiment, the patients with recurrent and/or platinum sensitive ovarian cancer are further characterized by the absence of a germline BRCA mutation that is deleterious or suspected to be deleterious. In another embodiment, the patients with recurrent and/or platinum sensitive ovarian cancer are further characterized by the absence of a BRCA mutation either germline or sporadic.

The present invention is based in part on the discovery that PARP inhibitors can be used to treat cancers characterized by wild type or mutant BRCA1 and/or BRCA2 ("BRCA genes"), e.g. in the absence or presence of a mutation in the BRCA genes. Accordingly, aspects of the invention relate to methods for treating cancer patients involving administration of an anti-PARP therapy to a patient independent of BRCA status or independent of the DNA repair status of the patient or cancer. In other aspects, the invention relates to methods for treating cancer patients involving administration of an anti-PARP therapy to a patient, wherein the therapy is commenced prior to determining the BRCA status or HRD status of the patient or the cancer. In other aspects, the invention relates to methods for treating cancer patients involving administration of an anti-PARP therapy to a patient, wherein the therapy is commenced in the absence of determining the BRCA status or DNA repair status of the patient or cancer. In other aspects, the invention relates to methods for treating cancer patients involving administration of an anti-PARP therapy to a patient characterized by an absence of a mutation in BRCA1 and/or BRCA2. In other aspects, the invention relates to methods for treating cancer patients involving administration of an anti-PARP therapy to a patient characterized by an absence of a mutation in a gene involved in DNA repair. In other aspects, the invention relates to methods for treating cancer patients involving administration of an anti-PARP therapy to a patient characterized by an absence of a mutation in a gene involved in homologous recombination. In aspects, the invention relates to methods for treating cancer patients involving administration of an anti-PARP therapy to a patient having a cancer characterized by an absence of a mutation in BRCA1 or BRCA2. In aspects, the invention relates to methods for treating cancer patients involving administration of an anti-PARP therapy to a patient having a cancer characterized by an absence of a mutation in a gene involved in homologous recombination.

In embodiments, the anti-PARP therapy is administered at a dose equivalent to about 100 mg, about 200 mg, or about 300 mg of niraparib or a salt or derivative thereof. In certain embodiments, the anti-PARP therapy is administered at a dose equivalent to about 100 mg of niraparib or a salt or derivative thereof. In certain embodiments, the anti-PARP therapy is administered at a dose equivalent to about 200 mg of niraparib or a salt or derivative thereof. In certain embodiments, the anti-PARP therapy is administered at a dose equivalent to about 300 mg of niraparib or a salt or derivative thereof.

In some embodiments, the anti-PARP therapy is administered in a regimen determined to achieve i) prolonged progression free survival as compared to control, ii) a reduced hazard ratio for disease progression or death as compared to control, iii) prolonged overall survival as compared to control, or iv) an overall response rate of at least 30%.

In embodiments, the anti-PARP therapy comprises administration of an agent that inhibits PARP-1 and/or PARP-2. In some embodiments, the agent is a small molecule, a nucleic acid, a polypeptide (e.g., an antibody), a carbohydrate, a lipid, a metal, or a toxin. In related embodiments, the agent is ABT-767, AZD 2461, BGB-290, BGP 15, CEP 9722, E7016, E7449, fluzoparib, INO1001, JPI 289, MP 124, niraparib, olaparib, ONO2231, rucaparib, SC 101914, talazoparib, veliparib, WW 46, or salts or derivatives thereof. In some related embodiments, the agent is niraparib, olaparib, rucaparib, talazoparib, veliparib, or salts or derivatives thereof. In certain embodiments, the agent is niraparib or a salt or derivative thereof. In certain embodiments, the agent is olaparib or a salt or derivative thereof. In certain embodiments, the agent is rucaparib or a salt or derivative thereof. In certain embodiments, the agent is talazoparib or a salt or derivative thereof. In certain embodiments, the agent is veliparib or a salt or derivative thereof.

In some embodiments, the methods prolong progression free survival as compared to control. In some embodiments, the methods reduce the hazard ratio for disease progression or death as compared to control. In some embodiments, the methods prolong overall survival as compared to control. In some embodiments, the methods achieve an overall response rate of at least 30%. In some embodiments, the methods achieve improved progression free survival 2 as compared to control. In some embodiments, the methods achieve improved chemotherapy free interval as compared to control. In some embodiments, the methods achieve improved time to first subsequent therapy as compared to control. In some embodiments, the methods achieve improved time to second subsequent therapy as compared to control. In some embodiments, the methods have been determined to not have a detrimental effect on Quality of Life as determined by FOSI and/or EQ-5D-5L. In some embodiments, the methods have been determined to not impact the effectiveness of a subsequent treatment with a chemotherapeutic agent (e.g., a platinum agent, including but not limited to, cisplatin, carboplatin, oxaliplatin, nedaplatin, triplatin tetranitrate, phenanthriplatin, picoplatin, or satraplatin.

In some embodiments, such cancers are selected from gynecologic cancers (i.e., cancers of the female reproductive system). In some embodiments, cancers of the female reproductive system include, but are not limited to, ovarian cancer, cancer of the fallopian tube(s), peritoneal cancer and breast cancer. In some embodiments, a gynecologic cancer is associated with homologous recombination repair deficiency/homologous repair deficiency ("HRD") and/or BRCA1/2 mutation(s). In some embodiments, a gynecologic cancer is platinum-sensitive. In some embodiments, a gynecologic cancer has responded to a platinum-based therapy. In some embodiments, a gynecologic cancer has developed resistance to a platinum-based therapy. In some embodiments, a gynecologic cancer has at one time shown a partial or complete response to platinum-based therapy. In some embodiments, a gynecologic cancer is now resistant to platinum-based therapy.

In certain embodiments, the cancer is ovarian cancer, cancer of the fallopian tube(s), or peritoneal cancer. In certain embodiments, the cancer is breast cancer.

In some embodiments, the cancer is a recurrent cancer.

In one embodiment, niraparib is administered as a maintenance therapy in patients with recurrent ovarian cancer (including fallopian and peritoneal cancers), wherein said administration of niraparib results in prolongation of progression free survival. In one embodiment, niraparib is administered as a monotherapy for the maintenance treatment of patients with recurrent ovarian, fallopian tube, or primary peritoneal cancer, wherein the patient is in response to platinum-based chemotherapy. In one embodiment, niraparib is administered as a monotherapy for the maintenance treatment of patients with deleterious or suspected deleterious germline or somatic BRCA mutated or homologous recombination deficient recurrent ovarian, fallopian tube, or primary peritoneal cancer, wherein the patient is in response to platinum-based chemotherapy.

Such a prolongation of progression free survival may result in a reduced hazard ratio for disease progression or death. Maintenance therapy is administered during the interval between cessation of initial therapy with the goal of delaying disease progression and the subsequent intensive therapies that may present tolerability issues for patients. In another embodiment, the patients with recurrent ovarian cancer are further characterized as having a BRCA deficiency or HRD. In another embodiment, the patients with recurrent ovarian cancer are further characterized by the absence of a germline BRCA mutation that is deleterious or suspected to be deleterious.

In one embodiment, niraparib is administered as a maintenance therapy in patients with recurrent ovarian cancer (including fallopian and peritoneal cancers) who have a complete response or partial response following multiple platinum-based chemotherapy treatment, wherein said administration of niraparib results in prolongation of progression free survival. Such a prolongation of progression free survival may result in a reduced hazard ratio for disease progression or death. Maintenance therapy is administered during the interval between cessation of chemotherapy with the goal of delaying disease progression and the subsequent intensive therapies that may present tolerability issues for patients. In another embodiment, the patients with recurrent ovarian cancer are further characterized as having a BRCA deficiency or HRD. In another embodiment, the patients with recurrent ovarian cancer are further characterized by the absence of a germline BRCA mutation that is deleterious or suspected to be deleterious.

In another embodiment, a second approach to address the high recurrence rate of ovarian cancers is to select patients with advanced ovarian cancer who will most benefit from specific targeted agents in the frontline therapy or maintenance setting. Accordingly, niraparib is administered as a therapy in patients with advanced ovarian cancer, wherein said administration results in an increase in overall survival and wherein administration is either as a treatment (in the case of continued disease following 1-4 prior lines of therapy) or a maintenance treatment (in the case of a patient with a PR or CR to a prior therapy). In another embodiment, the patients with advanced ovarian cancer are further characterized as having a BRCA deficiency or HRD. In another embodiment, the patients with recurrent ovarian cancer are further characterized by the absence of a germline BRCA mutation that is deleterious or suspected to be deleterious.

In some embodiments, the present invention provides a method of administering niraparib to a patient having recurrent or platinum sensitive ovarian cancer, fallopian tube cancer, or primary peritoneal cancer comprising administering niraparib according to a regimen determined to achieve prolonged progression free survival. In some embodiments, the progression free survival is greater in patients receiving niraparib, for example as compared with patients not receiving niraparib. In some embodiments, progression free survival is greater in patients receiving niraparib than in patients receiving alternative cancer therapy, for example such as therapy with a different PARP inhibitor.

In some embodiments, the prolonged progression free survival is at least 9 months. In some embodiments, the progression free survival is at least 12 months. In some embodiments, the progression free survival is at least 15 months. In some embodiments, the progression free survival is at least 18 months. In some embodiments, the progression free survival is at least 21 months. In some embodiments, the progression free survival is at least 24 months. In some embodiments, the progression free survival is at least 27 months. In some embodiments, the progression free survival is at least 30 months. In some embodiments, the progression free survival is at least 33 months. In some embodiments, the progression free survival is at least 36 months.

In some embodiments, the patient has a germline mutation in BRCA1 and/or BRCA2 (gBRCA$^{mut}$). In some embodiments, the prolonged progression free survival is at least 9 months. In some embodiments, the prolonged progression free survival is at least 12 months. In some embodiments, the prolonged progression free survival is at least 15 months. In some embodiments, the prolonged progression free survival is at least 18 months. In some embodiments, the prolonged progression free survival is at least 21 months. In some embodiments, the prolonged progression free survival is at least 24 months. In some embodiments, the prolonged progression free survival is at least 27 months. In some embodiments, the prolonged progression free survival is at least 30 months. In some embodiments, the prolonged progression free survival is at least 33 months. In some embodiments, the prolonged progression free survival is at least 36 months.

In some embodiments, the patient is characterized by an absence of a germline mutation in BRCA1 and/or BRCA2 (non-gBRCA$^{mut}$). In some embodiments, the patient has a tumor with a positive homologous recombination deficiency status. In some embodiments, the patient has a negative recombination deficiency status. In some embodiments, the prolonged progression free survival is at least 9 months. In some embodiments, the prolonged progression free survival is at least 12 months. In some embodiments, the prolonged progression free survival is at least 15 months. In some embodiments, the prolonged progression free survival is at least 18 months. In some embodiments, the prolonged progression free survival is at least 21 months. In some embodiments, the prolonged progression free survival is at least 24 months. In some embodiments, the prolonged progression free survival is at least 27 months. In some embodiments, the prolonged progression free survival is at least 30 months. In some embodiments, the prolonged progression free survival is at least 33 months. In some embodiments, the prolonged progression free survival is at least 36 months.

In some embodiments, the patient is characterized by an absence of a mutation in BRCA1 and/or BRCA2 (BRCA$^{wt}$). In some embodiments, the patient has a tumor with a positive homologous recombination deficiency status. In some embodiments, the patient has a negative homologous recombination deficiency status. In some embodiments, the prolonged progression free survival is at least 9 months. In some embodiments, the prolonged progression free survival is at least 12 months. In some embodiments, the prolonged progression free survival is at least 15 months. In some embodiments, the prolonged progression free survival is at least 18 months. In some embodiments, the prolonged progression free survival is at least 21 months. In some embodiments, the prolonged progression free survival is at least 24 months. In some embodiments, the prolonged progression free survival is at least 27 months. In some embodiments, the prolonged progression free survival is at least 30 months. In some embodiments, the prolonged progression free survival is at least 33 months. In some embodiments, the prolonged progression free survival is at least 36 months.

In some embodiments, the present invention provides a method of administering niraparib to a patient having recurrent or platinum sensitive ovarian cancer, fallopian tube cancer, or primary peritoneal cancer comprising administering niraparib according to a regimen determined to achieve a hazard ratio for disease progression or death. In some embodiments, the hazard ratio is improved in patients receiving niraparib, for example as compared with patients not receiving niraparib. In some embodiments, the hazard ratio is improved in patients receiving niraparib than in patients receiving alternative cancer therapy, for example such as therapy with a different PARP inhibitor.

In some embodiments, the hazard ratio for disease progression is about 0.3. In some embodiments, the hazard ratio for disease progression is about 0.4. In some embodiments, the hazard ratio for disease progression is about 0.45. In some embodiments, the hazard ratio for disease progression is about 0.5. In some embodiments, the hazard ratio for disease progression is less than about 0.5. In some embodiments, the hazard ratio for disease progression is less than about 0.45. In some embodiments, the hazard ratio for disease progression is less than about 0.4. In some embodiments, the hazard ratio for disease progression is less than about 0.35. In some embodiments, the hazard ratio for disease progression is less than about 0.3.

In some embodiments, the patient has a germline mutation in BRCA1 and/or BRCA2 (gBRCA$^{mut}$). In some embodiments, the hazard ratio for disease progression is about 0.3. In some embodiments, the hazard ratio for disease progression is about 0.4. In some embodiments, the hazard ratio for disease progression is about 0.45. In some embodiments, the hazard ratio for disease progression is about 0.5. In some embodiments, the hazard ratio for disease progression is less than about 0.5. In some embodiments, the hazard ratio for disease progression is less than about 0.45. In some embodiments, the hazard ratio for disease progression is less than about 0.4. In some embodiments, the hazard ratio for disease progression is less than about 0.35. In some embodiments, the hazard ratio for disease progression is less than about 0.3.

In some embodiments, the patient is characterized by an absence of a germline mutation in BRCA1 and/or BRCA2 (non-gBRCA$^{mut}$). In some embodiments, the patient has a tumor with a positive homologous recombination deficiency status. In some embodiments, the patient has a negative recombination deficiency status. In some embodiments, the hazard ratio for disease progression is about 0.3. In some embodiments, the hazard ratio for disease progression is about 0.4. In some embodiments, the hazard ratio for disease progression is about 0.45. In some embodiments, the hazard ratio for disease progression is about 0.5. In some embodiments, the hazard ratio for disease progression is less than about 0.5. In some embodiments, the hazard ratio for disease progression is less than about 0.45. In some embodiments, the hazard ratio for disease progression is less than about 0.4. In some embodiments, the hazard ratio for disease progression is less than about 0.35. In some embodiments, the hazard ratio for disease progression is less than about 0.3.

In some embodiments, the present invention provides a method of administering niraparib to a patient having recurrent and/or platinum sensitive ovarian cancer, fallopian tube cancer, or primary peritoneal cancer comprising administering niraparib according to a regimen determined to achieve prolonged overall survival. In some embodiments, the prolonged overall survival is greater in patients receiving niraparib, for example as compared with patients not receiving niraparib. In some embodiments, prolonged overall survival is greater in patients receiving niraparib than in patients receiving alternative cancer therapy, for example such as therapy with a different PARP inhibitor.

In some embodiments, the patient has at least (i) a germline mutation in BRCA1 or BRCA2 or (ii) a sporadic mutation in BRCA1 or BRCA2.

In some embodiments, the patient has high grade serous ovarian cancer or high grade predominantly serous histology ovarian cancer.

In some embodiments, the patient is further characterized by an absence of a germline mutation in BRCA1 or BRCA2.

In some embodiments, the patient is further characterized by an absence of a sporadic mutation in BRCA1 or BRCA2.

In some embodiments, the patient is further characterized by a negative BRCA1/2 status. In some embodiments, a germline mutation in BRCA1 or BRCA2 is not detected in a sample from a patient.

In some embodiments, progression for the purposes of determining progression free survival is determined by 1) tumor assessment by CT/MRI showing unequivocal progressive disease according to RECIST 1.1 criteria; and/or 2) additional diagnostic tests (e.g. histology/cytology, ultrasound techniques, endoscopy, positron emission tomography) identifying new lesions.

In some embodiments, the patient is characterized by having homologous recombination deficiency. In some embodiments, the patient has a positive homologous recombination deficiency status. Homologous recombination deficiency status may be established according to methods known by those in the art. For example, in some embodiments, recombinant deficiency status is established by determining in a patient sample the number of Indicator CA Regions. In some embodiments, the number of Indicator CA Regions comprises at least two types chosen from Indicator LOH Regions, Indicator TAI Regions, or Indicator LST Regions in at least two pairs of human chromosomes of a cancer cell. In some embodiments a CA Region (whether an LOH Region, TAI region, or LST Region) is an Indicator CA Region (whether an Indicator LOH Region, Indicator TAI region, or Indicator LST Region) if it is at least 3, 4, 5, 6, 7, 8, 9, 10, 11, 12, 13, 14, 15, 16, 17, 18, 19, 20, 25, 30, 35, 40, 45, 50, 60, 70, 80, 90, or 100 megabases or more in length.

In some embodiments, Indicator LOH Regions are LOH Regions that are longer than about 1.5, 5, 12, 13, 14, 15, 16, 17 or more (preferably 14, 15, 16 or more, more preferably 15 or more) megabases but shorter than the entire length of the respective chromosome within which the LOH Region is located. Alternatively or additionally, the total combined length of such Indicator LOH Regions may be determined. In some embodiments, Indicator TAI Regions are TAI Regions with allelic imbalance that (a) extend to one of the subtelomeres, (b) do not cross the centromere and (c) are longer than 1.5, 5, 12, 13, 14, 15, 16, 17 or more (preferably 10, 11, 12 or more, more preferably 11 or more) megabases. Alternatively or additionally, the total combined length of such Indicator TAI Regions may be determined. Because the concept of LST already involves regions of some minimum size (such minimum size being determined based on its ability to differentiate HRD from HDR intact samples), Indicator LST Regions as used herein are the same as LST Regions. Furthermore, an LST Region Score can be either derived from the number of regions showing LST as described above or the number of LST breakpoints. In some embodiments the minimum length of the region of stable copy number bounding the LST breakpoint is at least 3, 4, 5, 6, 7, 8, 9, 10, 11 12, 13, 14, 15, 16, 17, 18, 19 or 20 megabases (preferably 8, 9, 10, 11 or more megabases, more preferably 10 megabases) and the maximum region remaining unfiltered is less than 0.1, 0.2, 0.3, 0.4, 0.5, 0.6, 0.7, 0.8, 0.9, 1, 1.5, 2, 2.5, 3, 3.5, 4 or fewer megabases (preferably 2, 2.5, 3, 3.5, or 4 or fewer megabases, more preferably fewer than 3 megabases). As used herein, a patient is determined to have a positive HRD status when a sample from said patient has a number of Indicator CA Regions or a CA Region Score (as defined herein) that exceeds that of a reference or threshold value.

In some embodiments, the present invention provides a method of administering niraparib, the method comprising steps of:
  administering niraparib to a population of subjects having one or more of the following characteristics:
    a BRCA mutation;
    a positive homologous recombination deficiency status; or
    exhibited response to prior therapy;
  according to a regimen determined to achieve prolonged progression free survival.

In some embodiments, the population of subjects has a BRCA mutation. In some embodiments, the BRCA mutation is a germline BRCA mutation (gBRCA$^{mut}$). In some embodiments, the BRCA mutation is a somatic (or sporadic) BRCA mutation (sBRCA$^{mut}$). In some embodiments, the population of subjects has a positive homologous recombination deficiency status. In some embodiments, the population of subjects exhibits non-mutated BRCA1/2 "BRCA$^{wt}$" or "BRCA$^{wt}$".

Measuring Tumor Response

Tumor response can be measured by, for example, the RECIST v 1.1 guidelines. The guidelines are provided by E. A. Eisenhauer, et al., "New response evaluation criteria in solid tumors: Revised RECIST guideline (version 1.1.)," Eur. J. of Cancer, 45: 228-247 (2009), which is incorporated by reference in its entirety. The guidelines require, first, estimation of the overall tumor burden at baseline, which is used as a comparator for subsequent measurements. Tumors can be measured via use of any imaging system known in the art, for example, by a CT scan, or an X-ray. Measurable disease is defined by the presence of at least one measurable lesion. In studies where the primary endpoint is tumor progression (either time to progression or proportion with progression at a fixed date), the protocol must specify if entry is restricted to those with measurable disease or whether patients having non-measurable disease only are also eligible.

When more than one measurable lesion is present at baseline, all lesions up to a maximum of five lesions total (and a maximum of two lesions per organ) representative of all involved organs should be identified as target lesions and will be recorded and measured at baseline (this means in instances where patients have only one or two organ sites involved a maximum of two and four lesions respectively will be recorded).

Target lesions should be selected on the basis of their size (lesions with the longest diameter), be representative of all involved organs, but in addition should be those that lend themselves to reproducible repeated measurements.

Lymph nodes merit special mention since they are normal anatomical structures which may be visible by imaging even if not involved by tumor. Pathological nodes which are defined as measurable and may be identified as target lesions must meet the criterion of a short axis of P15 mm by CT scan. Only the short axis of these nodes will contribute to the baseline sum. The short axis of the node is the diameter normally used by radiologists to judge if a node is involved by solid tumor. Nodal size is normally reported as two dimensions in the plane in which the image is obtained (for CT scan this is almost always the axial plane; for MRI the plane of acquisition may be axial, saggital or coronal). The smaller of these measures is the short axis.

For example, an abdominal node which is reported as being 20 mm·30 mm has a short axis of 20 mm and qualifies as a malignant, measurable node. In this example, 20 mm should be recorded as the node measurement. All other pathological nodes (those with short axis P10 mm but <15 mm) should be considered non-target lesions. Nodes that have a short axis <10 mm are considered non-pathological and should not be recorded or followed.

A sum of the diameters (longest for non-nodal lesions, short axis for nodal lesions) for all target lesions will be calculated and reported as the baseline sum diameters. If lymph nodes are to be included in the sum, then as noted above, only the short axis is added into the sum. The baseline sum diameters will be used as reference to further characterize any objective tumor regression in the measurable dimension of the disease.

All other lesions (or sites of disease) including pathological lymph nodes should be identified as non-target lesions and should also be recorded at baseline. Measurements are not required and these lesions should be followed as 'present', 'absent', or in rare cases 'unequivocal progression.' In addition, it is possible to record multiple nontarget lesions involving the same organ as a single item on the case record form (e.g. 'multiple enlarged pelvic lymph nodes' or 'multiple liver metastases').

General Protocol

As described herein, provided methods comprise administering niraparib to a patient, a subject, or a population of subjects according to a regimen that achieves any one of or combination of: prolonged progression free survival; reduced hazard ratio for disease progression or death; and/or prolonged overall survival or a positive overall response rate. In some embodiments, niraparib is administered simultaneously or sequentially with an additional therapeutic agent, such as, for example, a chemotherapeutic agent (e.g., a platinum-based agent). In some embodiments, niraparib is administered before, during, or after administration of a chemotherapeutic agent.

Administration of niraparib simultaneously or sequentially with an additional therapeutic agent (e.g., a chemotherapeutic agent) is referred to as "combination therapy." In combination therapy, niraparib can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the chemotherapeutic agent to a subject in need thereof. In some embodiments niraparib and the chemotherapeutic agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

In some embodiments, niraparib is administered to a patient or population of subjects who has exhibited response to prior therapy. In some embodiments, the patient or population of subjects has exhibited response to prior therapy with a chemotherapeutic agent. In some such embodiments, the chemotherapeutic agent is a platinum agent.

In some embodiments, niraparib is administered as a maintenance therapy following complete or partial response to at least one platinum based therapy. In some embodiments, the at least one platinum-based therapy comprises administering to a patient in need thereof a platinum-based agent selected from cisplatin, carboplatin, oxaliplatin, nedaplatin, triplatin tetranitrate, phenanthriplatin, picoplatin, or satraplatin. In some embodiments, response to the most recent platinum-based chemotherapy regimen is a complete response. In some embodiments, response to the most recent platinum-based chemotherapy regimen is a partial response.

In some embodiments, the regimen comprises at least one oral dose of niraparib. In some embodiments, the regimen comprises a plurality of oral doses. In some embodiments, the regimen comprises once daily (QD) dosing.

In some embodiments, the regimen comprises at least one 28 day cycle. In some embodiments, the regimen comprises a plurality of 28 day cycles. In some embodiments, the regimen comprises one 28 day cycle. In some embodiments, the regimen comprises two 28 day cycles. In some embodiments, the regimen comprises three 28 day cycles. In some embodiments, the regimen comprises continuous 28 day cycles. In some embodiments, the regimen comprises administration of an effective dose of niraparib daily until disease progression or unacceptable toxicity occurs. In some embodiments, the regimen comprises a daily dose of at least 100, 200 or 300 mg niraparib per day dosed until disease progression or unacceptable toxicity occurs.

In some embodiments, the oral dose is an amount of niraparib within a range of about 5 to about 400 mg. In some embodiments, the amount of niraparib is about 5, about 10, about 25, about 50, about 100, about 150, about 200, about 250, about 300, about 350, or about 400 mg. In some embodiments, the amount of niraparib is about 300 mg of niraparib. In some embodiments, the regimen comprises administration of 300 mg of niraparib once daily.

In some embodiments, the oral dose is administered in one or more unit dosage forms. In some embodiments, the one or more unit dosage forms are capsules. In some embodiments, each unit dosage form comprises about 5, about 10, about 25, about 50, or about 100 mg of niraparib. It is understood that any combination of unit dosage forms can be combined to form a once daily (QD) dose. For example, three 100 mg unit dosage forms can be taken once daily such that 300 mg or niraparib is administered once daily. In some embodiments, niraparib is administered as a single 300 mg unit dosage form. In some embodiments, niraparib is administered 300 mg QD. In some embodiments, niraparib is administered as 3×100 mg QD (i.e., niraparib is administered as three unit dosage forms of 100 mg). In some embodiments, niraparib is administered as 2×150 mg QD (i.e., niraparib is administered as two unit dosage forms of 150 mg)

Pharmacokinetics

Pharmacokinetic data can be obtained by known techniques in the art. Due to the inherent variation in pharmacokinetic and pharmacodynamic parameters of drug metabolism in human subjects, appropriate pharmacokinetic and pharmacodynamic profile components describing a particular composition can vary. Typically, pharmacokinetic and pharmacodynamic profiles are based on the determination of the mean parameters of a group of subjects. The group of subjects includes any reasonable number of subjects suitable for determining a representative mean, for example, 5 subjects, 10 subjects, 16 subjects, 20 subjects, 25 subjects, 30 subjects, 35 subjects, or more. The mean is determined by calculating the average of all subject's measurements for each parameter measured.

In some embodiments, the pharmacokinetic parameter(s) can be any parameters suitable for describing the present composition. For example, in some embodiments, the $C_{max}$ is not less than about 500 ng/ml; not less than about 550 ng/ml; not less than about 600 ng/ml; not less than about 700 ng/ml; not less than about 800 ng/ml; not less than about 880 ng/ml, not less than about 900 ng/ml; not less than about 100 ng/ml; not less than about 1250 ng/ml; not less than about 1500 ng/ml, not less than about 1700 ng/ml, or any other $C_{max}$ appropriate for describing a pharmacokinetic profile of niraparib.

In some embodiments wherein the active metabolite is formed in vivo after administration of a drug to a subject, the $C_{max}$ is not less than about 500 pg/ml; not less than about 550 pg/ml; not less than about 600 pg/ml; not less than about 700 pg/ml; not less than about 800 pg/ml; not less than about 880 pg/ml, not less than about 900 pg/ml; not less than about 1000 pg/ml; not less than about 1250 pg/ml; not less than about 1500 pg/ml, not less than about 1700 pg/ml, or any other $C_{max}$ appropriate for describing a pharmacokinetic profile of a compound formed in vivo after administration of niraparib to a subject.

In some embodiments, the $T_{max}$ is, for example, not greater than about 0.5 hours, not greater than about 1.0 hours, not greater than about 1.5 hours, not greater than about 2.0 hours, not greater than about 2.5 hours, or not greater than about 3.0 hours, or any other $T_{max}$ appropriate for describing a pharmacokinetic profile of niraparib.

In general, AUC as described herein is the measure of the area under the curve that corresponds to the concentration of an analyte over a selected time period following administration of a dose of a therapeutic agent. In some embodiments, such time period begins at the dose administration (i.e., 0 hours after dose administration) and extends for about 2, about 3, about 4, about 5, about 6, about 7, about 8, about 9, about 10, about 11, about 12, about 14, about 16, about 18, about 20, about 22, about 24, about 30, about 40, or more hours after the dose administration. In some embodiments, AUC is that achieved from 0 hours to 12 hours following administration of a dose described herein. In some embodiments, AUC is that achieved from 0 hours to 18 hours following administration of a dose described herein. In some embodiments, AUC is that achieved from 0 hours to 24 hours following administration of a dose described herein. In some embodiments, AUC is that achieved from 0 hours to 36 hours following administration of a dose described herein.

The $AUC_{(0-inf)}$ can be, for example, not less than about 590 ng·hr/mL, not less than about 1500 ng·hr/mL, not less than about 2000 ng·hr/mL, not less than about 3000 ng·times·hr/ml, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, or any other AUCco-int) appropriate for describing a pharmacokinetic profile of a therapeutic agent (e.g., niraparib). In some embodiments wherein an active metabolite is formed in vivo after administration of a therapeutic agent (e.g., niraparib) to a subject; the $AUC_{(0-inf)}$ can be, for example, not less than about 590 pg·hr/mL, not less than about 1500 pg·hr/mL, not less than about 2000 pg·hr/mL, not less than about 3000 pg·hr/mL, not less than about 3500 pg·hr/mL, not less than about 4000 pg·hr/mL, not less than about 5000 pg·hr/mL, not less than about 6000 pg·hr/mL, not less than about 7000 pg·hr/mL, not less than about 8000 pg·hr/mL, not less than about 9000 pg·hr/mL, or any other $AUC_{(0-inf)}$ appropriate for describing a pharmacokinetic profile of a compound formed in vivo after administration of niraparib to a subject.

The plasma concentration of niraparib about one hour after administration can be, for example, not less than about 140 ng/ml, not less than about 425 ng/ml, not less than about 550 ng/ml, not less than about 640 ng/ml, not less than about 720 ng/ml, not less than about 750 ng/ml, not less than about 800 ng/ml, not less than about 900 ng/ml, not less than about 1000 ng/ml, not less than about 1200 ng/ml, or any other plasma concentration of niraparib.

In some embodiments, a patient population includes one or more subjects ("a population of subjects") suffering from metastatic disease.

In some embodiments, a patient population includes one or more subjects that are suffering from or susceptible to cancer. In some such embodiments, the cancer is ovarian cancer, cancer of the fallopian tubes, peritoneal cancer or breast cancer. In some embodiments, a patient population includes one or more subjects (e.g., comprises or consists of subjects) suffering from cancer. For example, in some embodiments, a patient population suffering from cancer may have previously been treated with chemotherapy, such as, e.g., treatment with a chemotherapeutic agent such as a platinum-based agent.

In some embodiments, the present disclosure provides methodologies that surprisingly can achieve substantially the same PK profile for niraparib when administered to a patient in a fed state or in a fasted state. Niraparib can be administered to a patient in either a fed or fasted state. Specifically, is has been surprisingly discovered that the bioavailability of niraparib is substantially similar for patients being administered niraparib in either a fed or fasted state. In some embodiments, administration of niraparib to a patient in a fed or fasted state produces substantially bioequivalent niraparib plasma $C_{max}$ values. In some embodiments, administration to the patient in a fed or fasted state produces bioequivalent niraparib plasma $T_{max}$ values. In some embodiments, administration to the patient in a fed or fasted state produces bioequivalent niraparib plasma AUC values. Accordingly, in some embodiments, niraparib is administered in either a fed or a fasted state. In some embodiments, niraparib is administered in a fasted state. In another embodiment, niraparib is administered in a fed state.

In some embodiments, a unit dose of niraparib can be administered to a patient in a fasted state. In some embodiments, a unit dose of niraparib can be administered to a patient in a fed state. In some embodiments, administration in one of the fed or fasted states is excluded. In some embodiments, the unit dose can be administered for therapeutic purposes in either the fed or the fasted state, with the subject having the option for each individual dose as to whether to take it with or without food. In some embodiments, the unit dose of niraparib can be administered immediately prior to food intake (e.g., within 30 or within 60 minutes before), with food, right after food intake (e.g., within 30, 60 or 120 minutes after food intake). In some embodiments, it can be administered, for example, at least 2 hours, 3 hours, 4 hours, 5 hours, 6 hours, 7 hours, 8 hours, 9 hours, 10 hours, 11 hours, 12 hours, or more after food intake, or any time there between. In some embodiments, the unit dose of niraparib is administered after overnight fasting. In some embodiments, the unit dose of the composition can be administered 30 minutes before food intake, 1 hour, 2 hours, 3 hours, 4 hours, 5 hours, 6 hours, 7 hours, 8 hours, 9 hours, 10 hours, 11 hours, 12 hours or more before food intake, or any time there between.

EXAMPLES

The following examples are provided to illustrate, but not limit the claimed invention.

Example 1. Treatment of Platinum Sensitive Ovarian Cancer

In NOVA, platinum-sensitive recurrent ovarian cancer patients who were in response following platinum-based treatment were prospectively randomized to receive either niraparib or placebo. Two cohorts were treated: the germline BRCA mutant positive cohort ($gBRCA^{mut}$) and the non-germline BRCA cohort (non-$gBRCA^{mut}$). Therefore, the $gBRCA^{mut}$ cohort of NOVA was designed to prospectively test the treatment effect of niraparib versus placebo in patients with platinum-sensitive recurrent ovarian cancer who were in response after platinum-based treatment. Patients in this cohort were germline BRCA mutation carriers as assessed by the FDA-approved Integrated BRACAnalysis test. Patients in the non-$gBRCA^{mut}$ were negative in the FDA-approved Integrated BRACAnalysis test.

The double-blind, 2:1 randomized, study evaluated niraparib as maintenance therapy in patients with recurrent and/or platinum sensitive ovarian cancer who had either $gBRCA^{mut}$ or a tumor with high-grade serous histology. The study compared maintenance treatment with niraparib with to placebo and is evaluating the efficacy of niraparib as maintenance therapy in patients who have recurrent ovarian cancer as assessed by the prolongation of progression-free survival (PFS). This objective is independently evaluated in a cohort of patients with germline BRCA mutation ($gBRCA^{mut}$) and in a cohort of patients who have high grade serous or high grade predominantly serous histology but without such gBRCA mutations (non-gBRCA$^{mut}$). Some patients in the non-gBRCA$^{mut}$ cohort have been reported to share distinctive DNA repair defects with gBRCA$^{mut}$ carriers, a phenomenon broadly described as "BRCAness." (See Turner, N., A. Tutt, and A. Ashworth, Hallmarks of 'BRCAness' in sporadic cancers. Nat. Rev. Cancer 4(10), 814-9, (2004)). Recent studies have suggested that homologous recombination deficiency (HRD) in epithelial ovarian cancer (EOC) is not solely due to germline BRCA1 and BRCA2 mutations. (See Hennessy, B. T. et al. Somatic mutations in BRCA1 and BRCA2 could expand the number of patients that benefit from poly (ADP ribose) polymerase inhibitors in ovarian cancer. Journal of clinical oncology: official journal of the American Society of Clinical Oncology 28, 3570-3576, (2010); TCGA "Integrated genomic analyses of ovarian carcinoma." Nature 474(7353), 609-615, (2011); and Dann R B, DeLoia J A, Timms K M, Zorn K K, Potter J, Flake D D 2nd, Lanchbury J S, Krivak T C. BRCA 1/2 mutations and expression: Response to platinum chemotherapy in patients with advanced stage epithelial ovarian cancer. Gynecol Oncol. 125(3), 677-82, (2012)). Non-BRCA deficiencies in homologous recombination DNA repair genes could also enhance tumor cell sensitivity to PARP inhibitors. Accordingly, HRD is used as a tumor biomarker classifier to be evaluated.

Patients enrolled in this study had received at least two platinum-based regimens, had a response (complete or partial) to their last regimen, and had no measurable disease >2 cm and normal cancer antigen CA125 (or >90% decrease) following their last treatment. Patients were assigned to one of two independent cohorts—one with deleterious gBRCA mutations (gBRCA$^{mut}$) and the other with high-grade serous histology but without such gBRCA mutations (non-gBRCA$^{mut}$) according to the following criteria:

| Mutation Status | Cohort for Randomization |
| --- | --- |
| Positive for a Deleterious Mutation | gBRCA$^{mut}$ cohort |
| Genetic Variant, Suspected Deleterious | gBRCA$^{mut}$ cohort |
| Genetic Variant, Favor Polymorphism | non-gBRCA$^{mut}$ cohort |
| Genetic Variant of Uncertain Significance | non-gBRCA$^{mut}$ cohort |
| No Mutation Detected | non-gBRCA$^{mut}$ cohort |

Patients were also assessed for HRD status and were further classified as HRD positive (HRDpos) or HRD negative (HRDneg).

Study treatment was dispensed to patients on Day 1 and every cycle (28 days) thereafter until the patient discontinued study treatment. Study treatment was administered orally once daily continuously. Three capsules of 100 mg strength were taken at each dose administration. Clinic visits occurred in each cycle (every 4 weeks±3 days). Response evaluation criteria in solid tumors (RECIST) tumor assessment via computed tomography (CT) or magnetic resonance imaging (MRI) scan of abdomen/pelvis and clinically indicated areas was required at the end of every 2 cycles (8 weeks with a window of ±7 days from date of visit) through Cycle 14, then at the end of every 3 cycles (12 weeks with a window of ±7 days from date of visit) until progression.

Patients were assessed by the prolongation of progression-free survival (PFS). More specifically, progression was determined if at least one of the following criteria is met: 1) tumor assessment by CT/MRI unequivocally shows progressive disease according to RECIST 1.1 criteria; 2) additional diagnostic tests (e.g. histology/cytology, ultrasound techniques, endoscopy, positron emission tomography) identify new lesions or determine existing lesions qualify for unequivocal progressive disease and CA-125 progression according to Gynecologic Cancer Intergroup (GCIG)-criteria (see Rustin et al., Int J Gynecol Cancer 2011; 21: 419-423); 3) definitive clinical signs and symptoms of PD unrelated to non-malignant or iatrogenic causes ([i] intractable cancer-related pain; [ii] malignant bowel obstruction/worsening dysfunction; or [iii] unequivocal symptomatic worsening of ascites or pleural effusion and CA-125 progression according to GCIG-criteria. Response Evaluation Criteria in Solid Tumors (RECIST) was used for tumor assessment via a computed tomography (CT) or magnetic resonance imaging (MRI) scan of abdomen/pelvis and clinically indicated areas, which was required at the end of every 2 cycles (8 weeks) through cycle 14 (56 weeks), and then at the end of every 3 cycles (12 weeks) until progression.

Patients continued to receive their assigned treatment until disease progression, unacceptable toxicity, death, withdrawal of consent, and/or lost to follow-up. Dose interruption and/or reduction were available at any time for any grade toxicity considered intolerable by the patient.

Results

Niraparib significantly prolonged PFS compared to control among patients who are germline BRCA mutation (gBRCA$^{mut}$) carriers irrespective of HRD status, among patients who are not germline BRCA mutation (non-gBRCA$^{mut}$) carriers but who have homologous recombination deficient (HRD) tumors, and overall in patients who are non-gBRCA$^{mut}$. The overall population in the non-gBRCA$^{mut}$ cohort also included patients with tumors that were HRDneg. Analyses demonstrated that the HRDneg population also benefitted from niraparib treatment. The determination of gBRCA status and HRD status can include determinations made by a standardized laboratory test, such as the Myriad myChoice® HRD test and also including those tests approved by a relevant regulatory authority.

Figure 6:
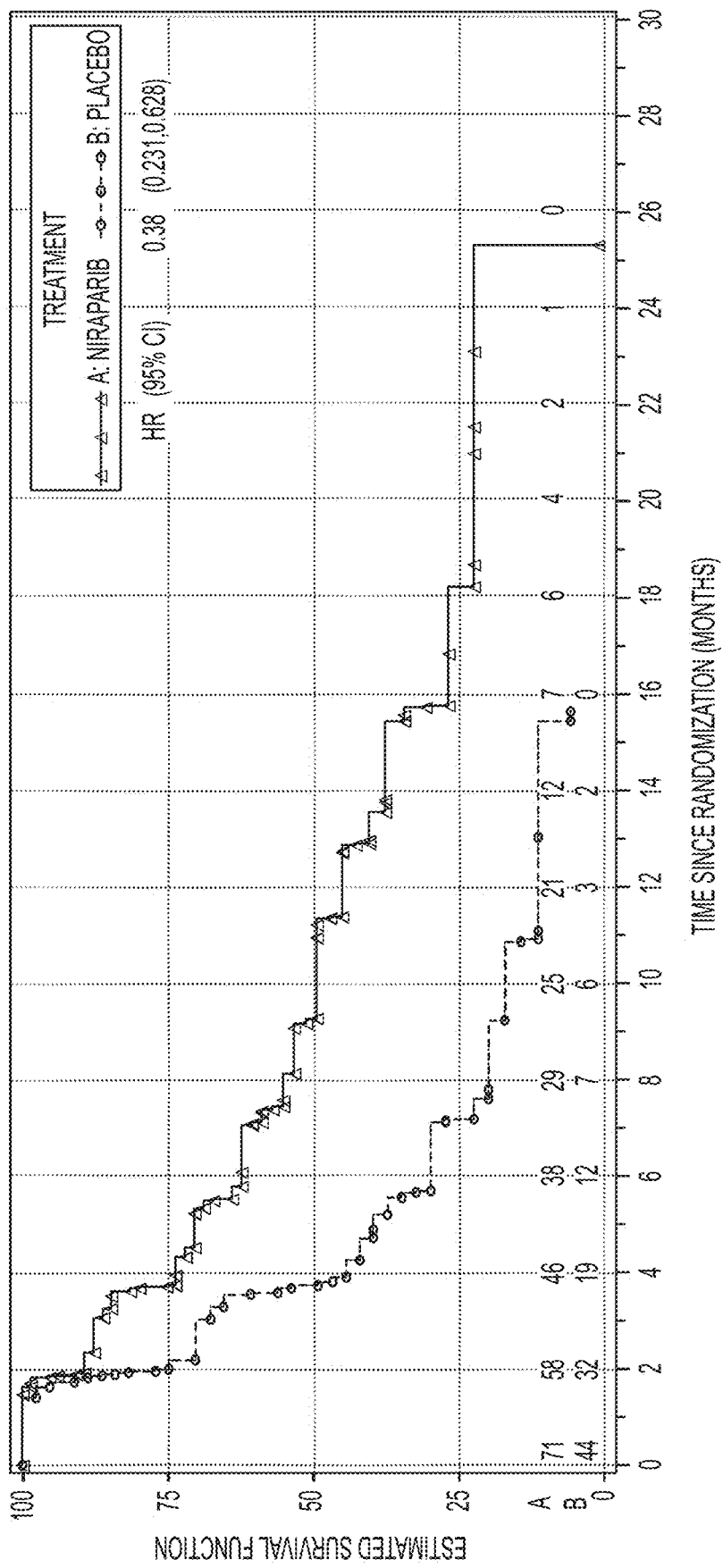
FIG. 6 depicts a graphical representation of the progression-free survival in the HRDpos/BRCAwt subgroup of the non-gBRCAmut cohort when treated with niraparib or with placebo. The y-axis shows the estimated survival function value and the x-axis shows the time (in months) since randomization.

For all populations, median PFS was significantly longer for patients who received niraparib than for patients who received placebo. Both of the primary efficacy populations in the non-gBRCA$^{mut}$ cohort (HRD positive and overall) demonstrated a significant treatment effect of niraparib compared to placebo (HR 0.38 versus HR 0.45, respectively; HR=hazard ratio). All populations exhibited a consistent and durable niraparib treatment effect as evidenced by the Kaplan Meyer curves (see FIGS. 1-4). Importantly, this same consistent durable benefit of niraparib treatment was observed in all exploratory subgroups tested within this cohort. In the non-gBRCA$^{mut}$ cohort, the HRD positive group included patients with somatic tumor BRCA mutations (HRDpos/sBRCA$^{mut}$) and patients who were wildtype for BRCA (HRDpos/BRCA$^{wt}$). Importantly, the observed treatment benefit within the HRDpos group was not driven solely by the effect in the HRDpos/sBRCA$^{mut}$ subgroup. The HRDpos/BRCA$^{wt}$ subgroup also experienced a consistent, durable benefit from niraparib treatment relative to the HRDpos overall group; with a hazard ratio of 0.38 (FIG. 6).

Figure 2:
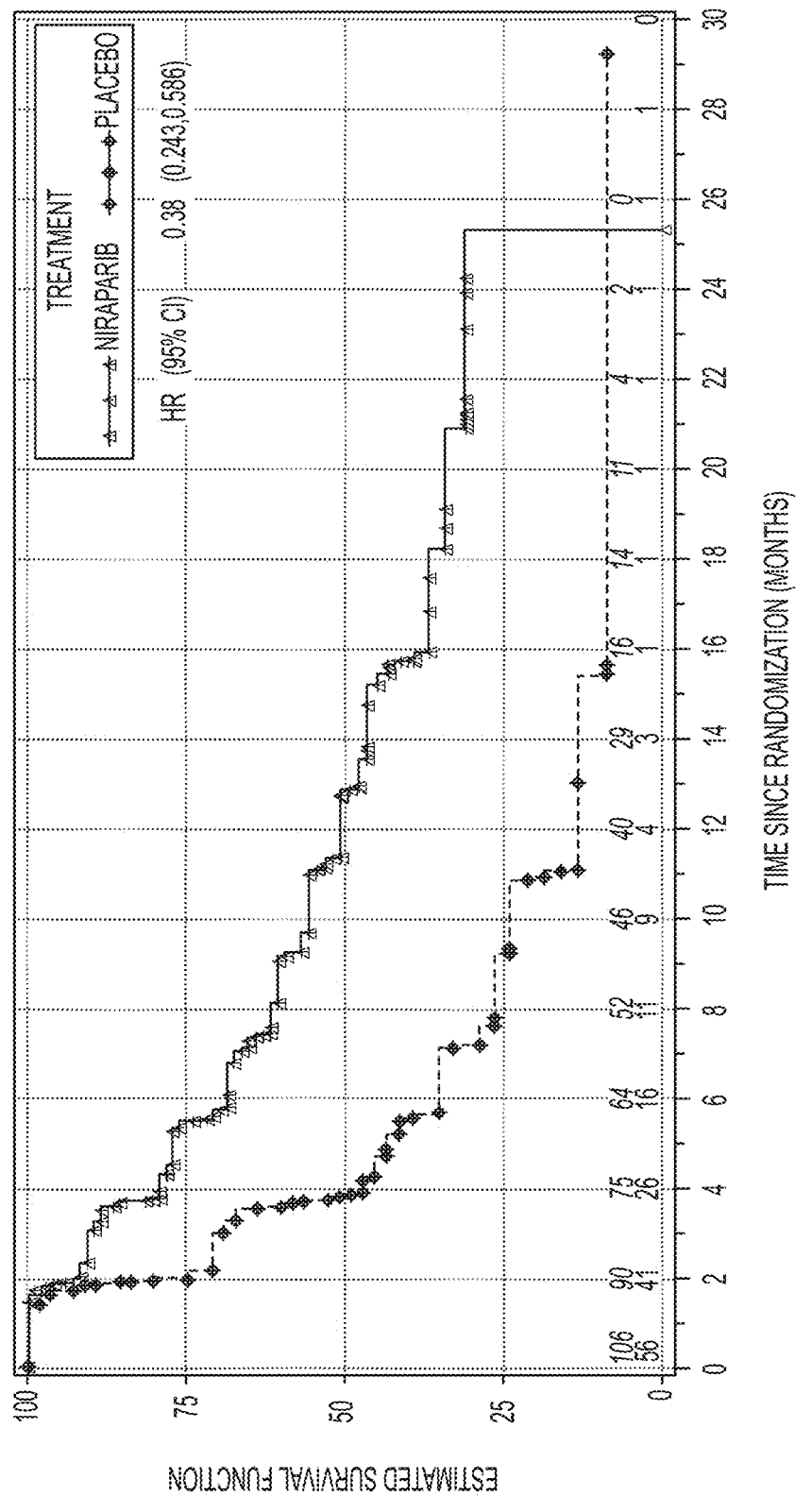
FIG. 2 relates to progression-free survival of a non-gBRCA-HRD positive cohort: the figure depicts a graphical representation of the progression free survival of patients who lack a genomic BRCA mutation (non-gBRCA) but have a HRD-positive tumor (positive HRD status) when treated with niraparib or with placebo. The y-axis shows the estimated survival function value and the x-axis shows the time (in months) since randomization. The hazard ratio for disease progression is shown on the graph as HR (95% CI) 0.38 (0.243, 0.586).

Among patients who were germline BRCA mutation carriers (gBRCA$^{mut}$), the niraparib arm successfully achieved statistical significance over the control arm for the primary endpoint of PFS, with a hazard ratio of 0.27. The median PFS for patients treated with niraparib was 21.0 months, compared to 5.5 months for control (p<0.0001). FIG. 1 depicts the PFS curve for gBRCA$^{mut}$ patients treated with niraparib and placebo. These results were markedly better than those from "Study 19" (N Engl J Med. 2012; 366(15):1382-1392), which was similar to NOVA in study design and assessed the activity of the PARP inhibitor olaparib versus placebo in a similar patient population. Study 19 reported a median PFS of 11.2 versus 4.3 months in the olaparib versus control arm for patients with BRCA mutations. For patients who were not germline BRCA mutation carriers (non-gBRCA$^{mut}$) but whose tumors were determined to be HRD positive using the Myriad myChoice® HRD test, the niraparib arm successfully achieved statistical significance over the control arm for the primary endpoint of PFS, with a hazard ratio of 0.38. The median PFS for patients with HRD-positive tumors who were treated with niraparib was 12.9 months, compared to 3.8 months for control (p<0.0001). FIG. 2 depicts the PFS curve for non-gBRCA$^{mut}$/HRD positive patients treated with niraparib and placebo.

Figure 3:
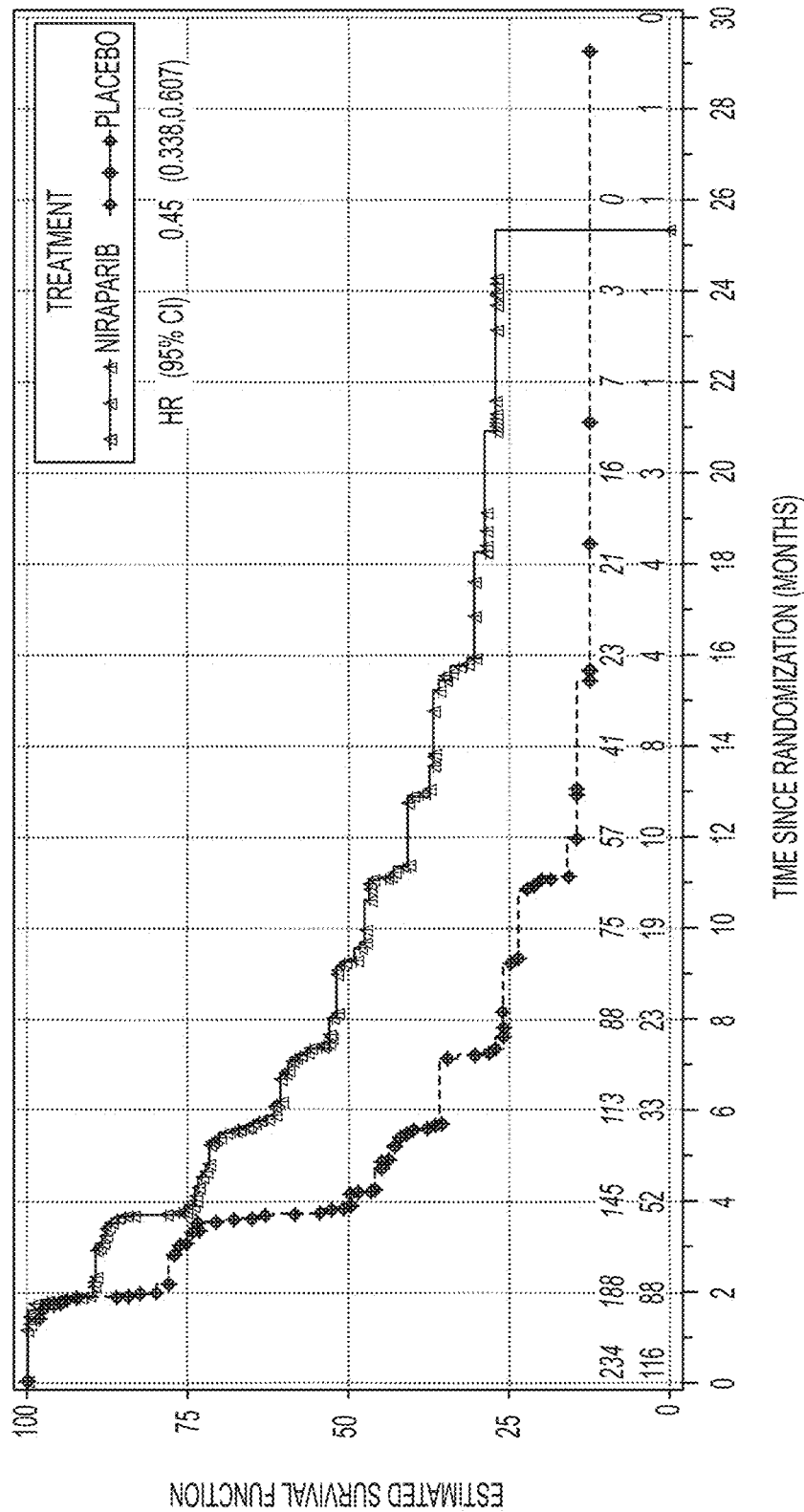
FIG. 3 relates to progression-free survival of non-gBRCA overall: the figure depicts a graphical representation of the progression free survival of patients that lack a genomic BRCA mutation (non-gBRCA) when treated with niraparib or with placebo. This population includes patients with or without HRD. The y-axis shows the estimated survival function value and the x-axis shows the time (in months) since randomization. The hazard ratio for disease progression is shown on the graph as HR (95% CI) 0.45 (0.338, 0.607).

Niraparib also showed statistical significance in the overall non-germline BRCA mutant cohort (non-gBRCA$^{mut}$), which included patients with both HRD-positive and HRD-negative tumors. The niraparib arm successfully achieved statistical significance over the control arm for the primary endpoint of PFS, with a hazard ratio of 0.45. The median PFS for patients treated with niraparib was 9.3 months, compared to 3.9 months for control (p<0.0001). FIG. 3 depicts the PFS curve for non-gBRCA$^{mut}$ patients (including both HRD-positive and HRD-negative patients) treated with niraparib and placebo.

Figure 4:
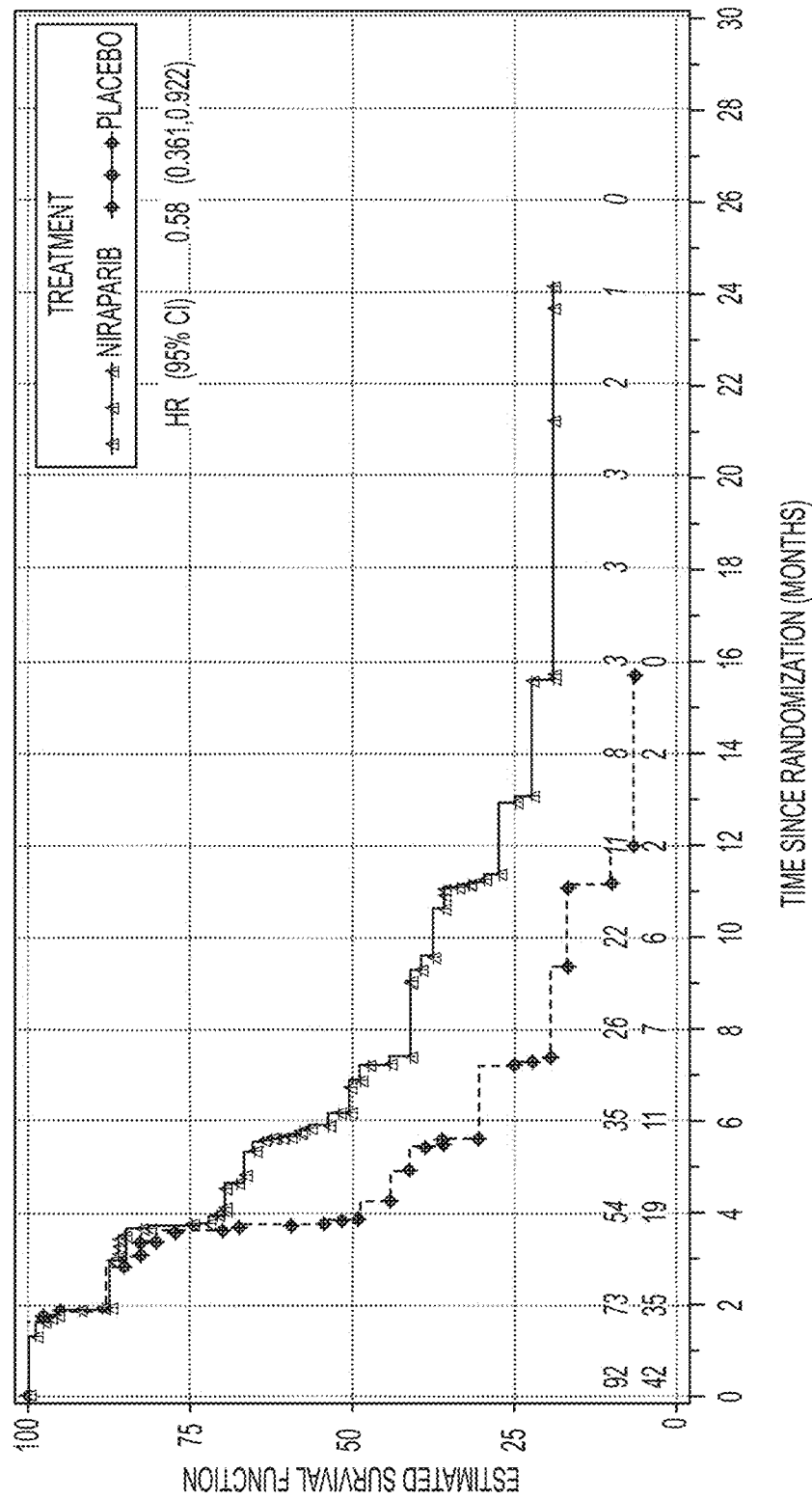
FIG. 4 relates to the progression-free survival of a non-gBRCA-HRD negative cohort: the figure depicts a graphical representation of the progression free survival of patients who lack a genomic BRCA mutation (non-gBRCA) and have a HRD-negative tumor (negative HRD status) when treated with niraparib or with placebo. The y-axis shows the estimated survival function value and the x-axis shows the time (in months) since randomization. The hazard ratio for disease progression is shown on the graph as HR (95% CI) 0.58 (0.361, 0.922).

Niraparib also showed statistical significance in the non-germline BRCA mutant (non-gBRCA$^{mut}$) patients with HRD-negative tumors. The niraparib arm successfully achieved statistical significance over the control arm for the primary endpoint of PFS, with a hazard ratio of 0.58. The median PFS for patients treated with niraparib was 6.9 months, compared to 3.8 months for control (p<0.0226). The PFS for non-germline BRCA mutant (non-gBRCA$^{mut}$) patients with HRD-negative tumors is shown in FIG. 4.

Figure 5:
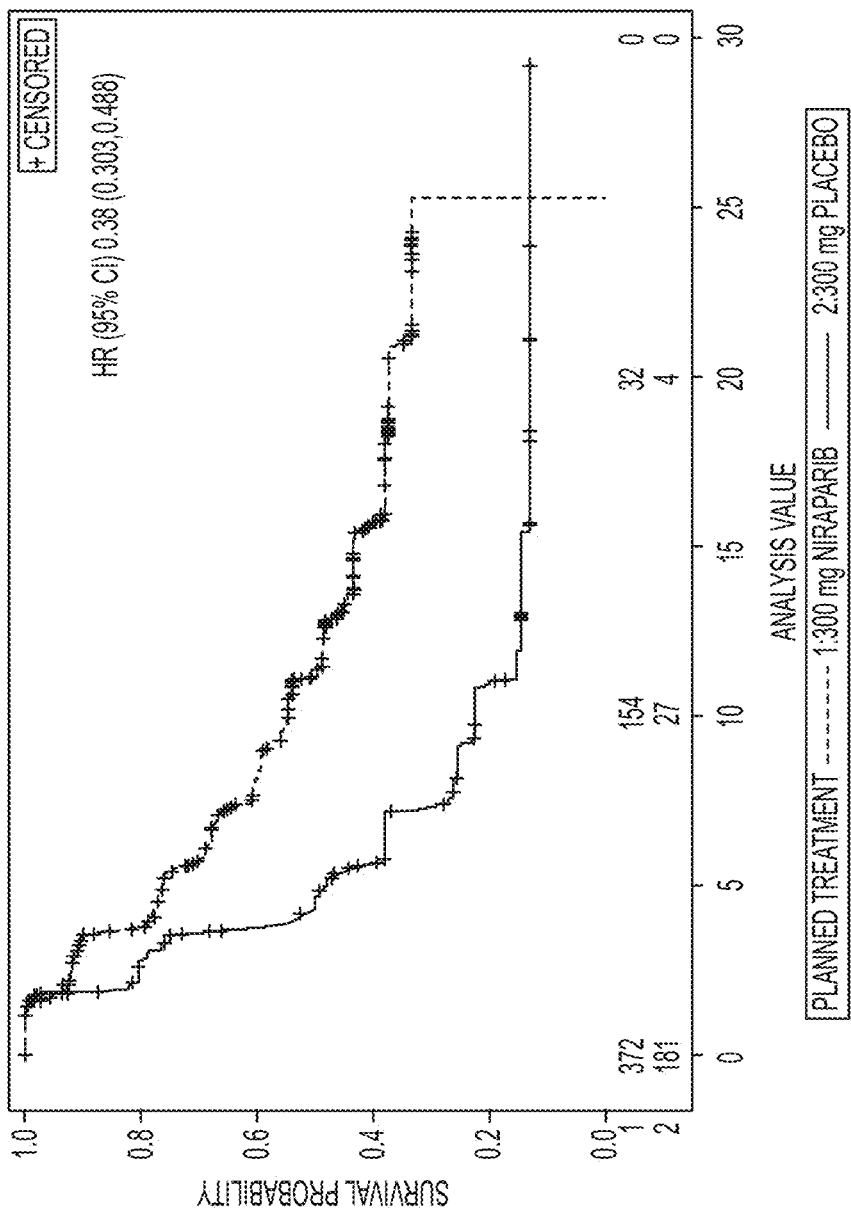
FIG. 5 relates to progression-free survival of a combined study population (2 cohorts combined: gBRCAmut and non-gBRCA mut): the figure depicts a graphical representation of the progression-free survival of the combined study population made up of the gBRCAmut and non-gBRCAmut populations when treated with niraparib or with placebo. The y-axis shows the estimated survival function value and the x-axis shows the time (in months) since randomization.

In an exploratory pooled analysis looking at the combined study population (2 cohorts combined gBRCA$^{mut}$ and non-gBRCA$^{mut}$), PFS was longer with niraparib than with placebo. The median PFS for all patients treated with niraparib was 11.3 months compared to 4.7 months for placebo treated patients, HR 0.38, 95% CI, 0.303, 0.488, p<0.0001) (FIG. 5). In addition, the treatment effect, as observed in the Kaplan Meier (KM) curves from the gBRCA$^{mut}$ and non-gBRCAmut cohort, the subgroups within the non-gBRCA$^{mut}$ cohort and the combined cohort analysis, was substantial, durable, and consistent.

A summary of the Progression Free Survival of the different patient cohorts is provided in Tables 1 through 3, below. "NR" means "not reached." "95% CI" means a 95% confidence interval. Exploratory analyses of biomarker-related subgroups in the non-gBRCA$^{mut}$ cohort were performed; the subgroups analyzed were HRDpos/somatic BRCA$^{mut}$, HRDpos/BRCA$^{wt}$, and HRDneg.

TABLE 1

Progression Free Survival (Primary)

| | gBRCA$^{mut}$ Cohort | | HRD-positive, non-gBRCA | | Overall non-gBRCA | |
|---|---|---|---|---|---|---|
| | Niraparib N = 35 | Placebo N = 12 | Niraparib N = 71 | Placebo N = 44 | Niraparib N = 92 | Placebo N = 42 |
| PFS (Months): Median (95% CI) | 21.0 (12.9, NR) | 5.5 (3.8, 7.2) | 12.9 (8.1, 15.9) | 3.8 (3.5, 5.7) | 9.3 (7.2, 11.2) | 3.9 (3.7, 5.5) |
| p-value | <0.0001 | | <0.0001 | | <0.0001 | |
| Hazard Ratio, Niraparib: Placebo (95% CI) | 0.27 (0.173, 0.410) | | 0.38 (0.243, 0.586) | | 0.45 (0.338, 0.607) | |

TABLE 2

Progression Free Survival, non-gBRCA

| | Somatic BRCA$^{mut}$, HRD positive | | BRCA$^{wt}$, HRD positive | | HRD negative | |
|---|---|---|---|---|---|---|
| | Niraparib N = 35 | Placebo N = 12 | Niraparib N = 71 | Placebo N = 44 | Niraparib N = 92 | Placebo N = 42 |
| PFS (Months): Median (95% CI) | 20.9 (9.7, NR) | 11.0 (2.0, NR) | 9.3 (5.8, 15.4) | 3.7 (3.3, 5.6) | 6.9 (5.6, 9.6) | 3.8 (3.7, 5.6) |
| p-value | 0.0248 | | 0.0001 | | 0.0226 | |
| Hazard Ratio, Niraparib: Placebo (95% CI) | 0.27 (0.081, 0.903) | | 0.38 (0.231, 0.628) | | 0.58 (0.361, 0.922) | |

TABLE 3

Treatment Effect of Niraparib versus Placebo in NOVA Patient Populations

| Treatment | Median PFS[1] (95% CI) (Months) | Hazard Ratio[2] (95% CI) p-value[3] | % of Patients without Progression or Death at:[4] | | |
|---|---|---|---|---|---|
| | | | 6 Months | 12 Months | 18 Months |
| gBRCAmut Cohort | | | | | |
| Niraparib (N = 138) | 21.0 (12.9, NE) | 0.27 (0.173, 0.410) | 80% | 62% | 50% |
| Placebo (N = 65) | 5.5 (3.8, 7.2) | p < 0.0001 | 43% | 16% | 16% |
| HRDpos Group | | | | | |
| Niraparib (N = 106) | 12.9 (8.1, 15.9) | 0.38 (0.243, 0.586) | 69% | 51% | 37% |
| Placebo (N = 56) | 3.8 (3.5, 5.7) | p < 0.0001 | 35% | 13% | 9% |
| HRDneg Group | | | | | |
| Niraparib (N = 92) | 6.9 (5.6, 9.6) | 0.58 (0.361, 0.922) | 54% | 27% | 19% |
| Placebo (N = 42) | 3.8 (3.7, 5.6) | p < 0.0226 | 31% | 7% | 7% |
| Non-gBRCAmut Cohort | | | | | |
| Niraparib (N = 234) | 9.3 (7.2, 11.2) | 0.45 (0.338, 0.607) | 61% | 41% | 30% |
| Placebo (N = 116) | 3.9 (3.7, 5.5) | p < 0.0001 | 36% | 14% | 12% |

CI = confidence interval;
PFS = progression-free survival;
NR = not reached;
sBRCAmut = somatic BRCA mutation;
BRCAwt = BRCA wild type;
HRD = homologous recombination deficiency
[1]Progression-free survival is defined as the time in months from the date of randomization to progression or death.
[2]Niraparib: Placebo, based on the stratified Cox Proportional Hazards Model using randomization stratification factors.
[3]Based on stratified log-rank test using randomization stratification factors.
[4]Estimates from product-limit method. Confidence intervals constructed using log-log transformation.

The most common (>10%) treatment-emergent grade 3/4 adverse events among all patients treated with niraparib were thrombocytopenia (28.3%), anemia (24.8%) and neutropenia (11.2%). Adverse events were managed via dose modifications among all patients. The rates of MDS/AML in the niraparib (1.3%) and control (1.2%) arms were similar in the ITT population. There were no deaths among patients during study treatment.

In this study, both of the primary efficacy populations in the non-gBRCA$^{mut}$ cohort (HRDpos and overall) demonstrated a significant treatment effect of niraparib compared to placebo (HR 0.38 versus HR 0.45, respectively; (Table 3). Both populations exhibited a consistent and durable niraparib treatment effect as evidenced by the Kaplan-Meier curves. This same consistent durable benefit of niraparib treatment was observed in all exploratory subgroups tested within this cohort.

In the non-gBRCA$^{mut}$ cohort, the HRDpos group included patients with somatic tumor BRCA mutations (HRDpos/sBRCA$^{mut}$) and patients who were wildtype for BRCA (HRDpos/BRCA$^{wt}$). The observed treatment benefit within the HRDpos group was not driven solely by the effect in the HRDpos/sBRCA$^{mut}$ subgroup. The HRDpos/BRCA$^{wt}$ subgroup also experienced a consistent, durable benefit from niraparib treatment relative to the HRDpos overall group; with a hazard ratio of 0.38 (FIG. 6).

Figure 7:
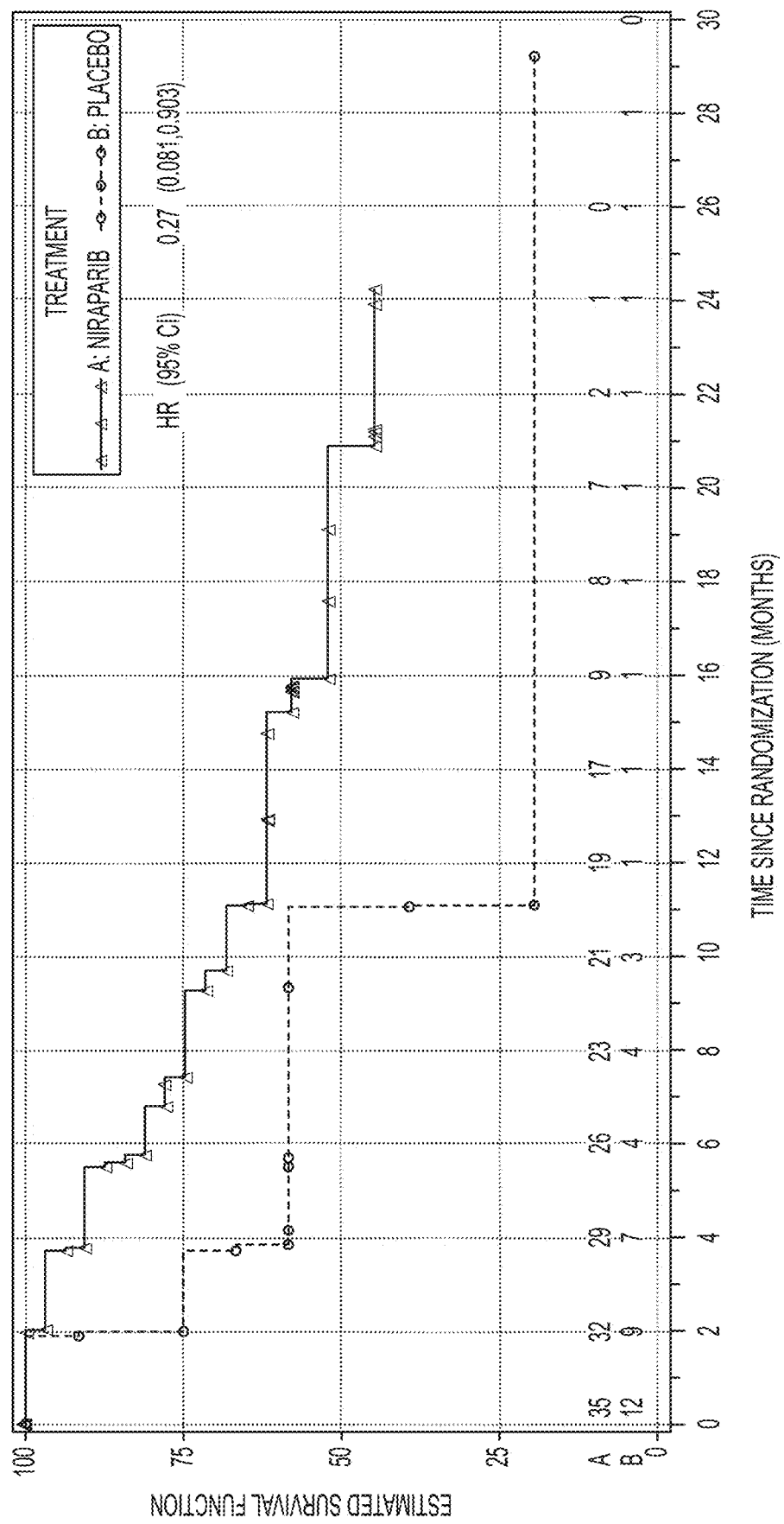
FIG. 7 depicts a graphical representation (Kaplan-Meier plot) of the progression-free survival in the HRDpos/somatic BRCAmut subgroup of the non-gBRCAmut cohort when treated with niraparib or with placebo. The y-axis shows the estimated survival function value and the x-axis shows the time (in months) since randomization.

Of note, the HR observed in the gBRCA$^{mut}$ cohort (0.27) was identical to the HR observed in the HRDpos/sBRCA$^{mut}$ subgroup demonstrating the consistency of the niraparib treatment effect across cohorts and in two independent patient populations with similar underlying tumor biology (FIG. 7).

Figure 12A:
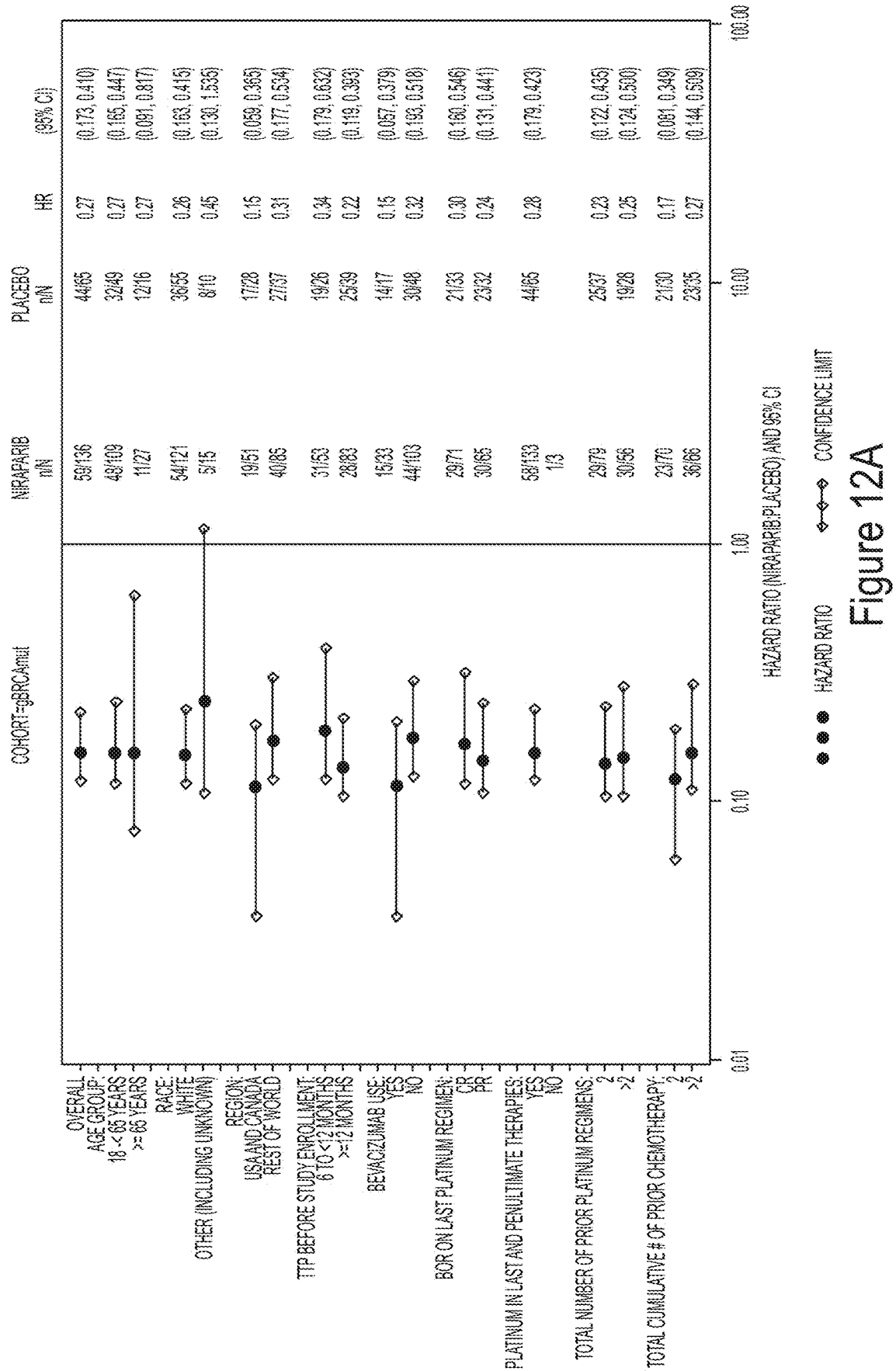
FIG. 12 depicts a graphical representation of analysis of progression-free survival in the (FIG. 12A) gBRCAmut Cohort, (FIG. 12B) non-gBRCAmut, HRDpos Subgroup, and (FIG. 12C) overall non-gBRCAmut Cohort.
Figure 12B:
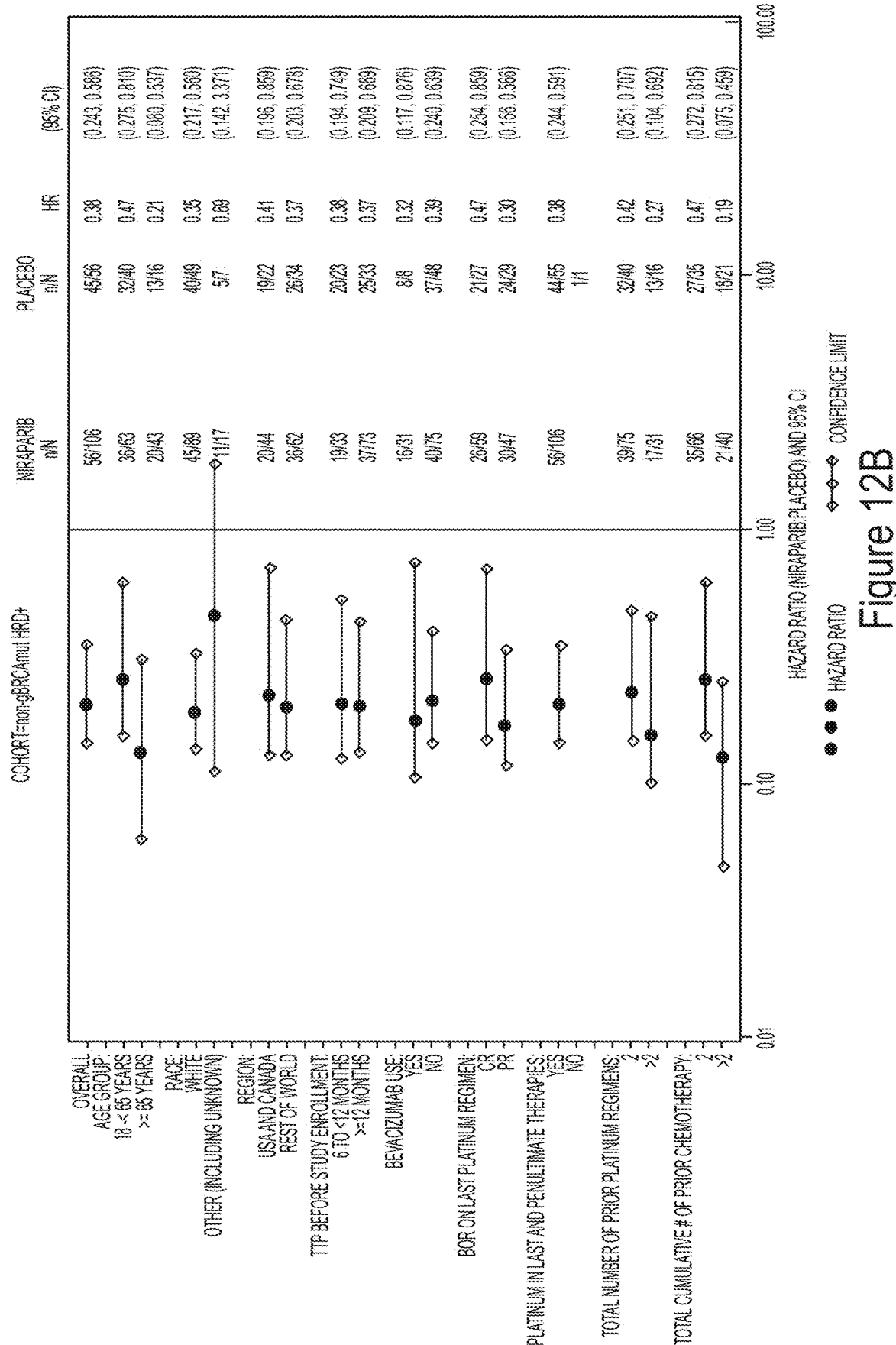
Figure 12C:
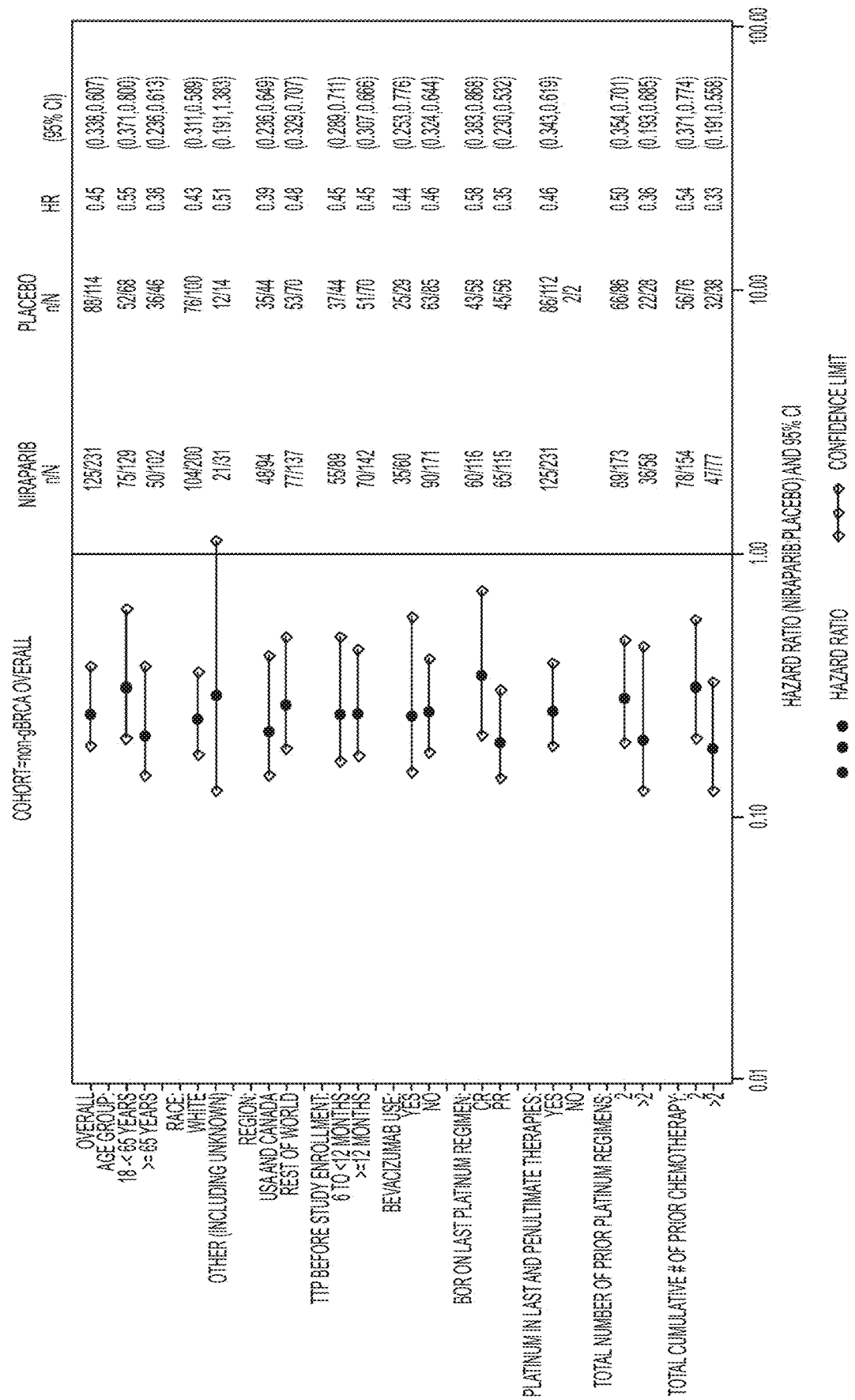

All of the point estimates for the hazard ratios were <1, indicating a longer progression-free survival for patients who received niraparib, for the gBRCA$^{mut}$ cohort (FIG. 12A), the HRD positive group of the non-gBRCA$^{mut}$ cohort p (FIG. 12B), and the overall non-gBRCA$^{mut}$ cohort (FIG. 12C).

Subgroup Analyses within the Non gBRCAmut Cohort

As detailed previously, the non-gBRCA$^{mut}$ cohort comprises 3 groups of patients: HRDpos, HRDneg, and those whose tumor HRD status could not be determined (HRDnd). Further, the HRDpos group includes 2 additional subgroups, women with somatic BRCA mutated tumors (sBRCA$^{mut}$) and those who had HRDpos tumors due to non-BRCA related defects in the HR pathway (HRDpos/BRCA$^{wt}$).

Within the HRDpos group of the non gBRCA$^{mut}$ cohort, 47 patients had sBRCAmut tumors and 115 had BRCA$^{wt}$ tumors. Results for the PFS analysis on these 2 subgroups of patients are provided in FIG. 7 and FIG. 6.

Among patients with HRDpos/sBRCA$^{mut}$, median PFS was 20.9 months (95% CI: 9.7, NE) in the niraparib arm versus 11.0 months (95% CI: 2.0, NE) in the placebo arm (11.0 months). The HR was 0.27 (95% CI: 0.081, 0.903) (p=0.0248). (See FIG. 7) The HR of 0.27 in the sBRCA$^{mut}$ subgroup confirms the 0.27 HR observed in the gBRCA$^{mut}$ cohort.

In patients with HRDpos/BRCA$^{wt}$ tumors, median PFS was 9.3 months (95% CI: 5.8, 15.4) in the niraparib arm versus 3.7 months (95% CI: 3.3, 5.6) in the placebo arm. The HR for was 0.38 (95% CI: 0.231, 0.628) (p=0.0001) showing a robust treatment effect for HRD patients even in the absence of sBRCA mutations. (See FIG. 6).

The overall population in the non-gBRCA$^{mut}$ cohort also included patients with tumors that were HRDneg and exploratory analyses demonstrated that this population experienced a benefit from niraparib treatment (HR 0.58). The Kaplan-Meier curves (FIG. 4) show a consistent and durable effect of niraparib versus placebo, albeit of a lower magnitude. Impact and durability of the niraparib effect is important in assessing the benefit of PFS. For example, probability of remaining progression-free at 12 months was 27% versus 7% in the niraparib versus placebo arms. At 18 months, more than twice as many niraparib versus placebo-treated patients estimated to be progression-free (19% versus 7%; Table 3). The benefit for these 20-25% of recurrent ovarian cancer patients is an important, surprising advance in the treatment of cancer.

Dose interruption and/or reduction could be implemented at any time for any grade toxicity considered intolerable by the patient. Treatment was required to be interrupted for any non-hematologic AE that was Grade 3 or 4, per NCI CTCAE v.4.02 if the Investigator considered the event to be related to administration of study drug. If toxicity was appropriately resolved to baseline or Grade 1 or less within 28 days, the patient was allowed to restart treatment with study drug, but with a dose level reduction according to Table 4, if prophylaxis was not considered feasible. If the event recurred at a similar or worse grade, the patient's treatment was again to be interrupted; upon event resolution, a further dose reduction was required; no more than 2 dose reductions were permitted for any patient.

TABLE 4

Dose Reductions for Non-Hematologic Toxicities

| Event[1] | Dose[2] |
|---|---|
| Initial dose | 300 mg QD |
| First dose reduction for NCI-CTCAE Grade 3 or 4 treatment-related SAE/AE where prophylaxis is not considered feasible | 200 mg QD |
| Second dose reduction for NCI-CTCAE Grade 3 or 4 treatment-related SAE/AE where prophylaxis is not considered feasible | 100 mg QD |
| Continued NCI-CTCAE Grade 3 or 4 treatment-related SAE/AE ≥ 28 days | Discontinue study drug |

Abbreviations:
AE = adverse event;
NCI-CTCAE = National Cancer Institute Common Terminology Criteria for Adverse Events;
QD = once daily;
SAE = serious adverse event
[1]Dose interruption and/or reduction may be implemented at any time for any grade toxicity considered intolerable by the patient.
[2]Dose not to be decreased below 100 mg QD If the toxicity requiring dose interruption did not resolve completely or to NCI CTCAE Grade 1 or less during the maximum 28-day dose interruption period, and/or the patient had already undergone a maximum of 2 dose reductions (to a minimum dose of 100 mg QD), the patient was required to permanently discontinue treatment with study drug.

There were no on-treatment deaths reported during the study. Most patients in both treatment arms experienced at least 1 TEAE, including all patients who received niraparib and 96% patients who received placebo. The high rate of TEAEs in the placebo arm indicates the lingering effects of prior chemotherapy and the patient's underlying ovarian cancer.

Overall, the incidence of treatment-related TEAEs was 98% in the niraparib arm and 71% in the placebo arm; the high rate of treatment-related TEAEs in patients receiving placebo shows the challenges of attributing events as related to study treatment and confirms the importance of including a placebo arm in the evaluation of safety in this population.

In niraparib versus placebo treated patients, the incidence of TEAEs was as follows: CTCAE Grade ≥3 TEAEs, 74% versus 23%; SAEs, 30% versus 15%; TEAEs leading to treatment interruption, 69% versus 5%; TEAEs leading to dose reduction, 67% versus 15%; and TEAEs leading to treatment discontinuation, 15% versus 2%. The most frequently reported TEAEs in the niraparib group were consistent with the known safety profile of niraparib and other PARP inhibitors. Most of the common TEAEs were reported at a higher incidence in the niraparib group than in the placebo group, with the exception of disease-related symptoms, including abdominal pain and distension, and other pain-related symptoms, including back pain, arthralgia, and myalgia.

Figure 8:
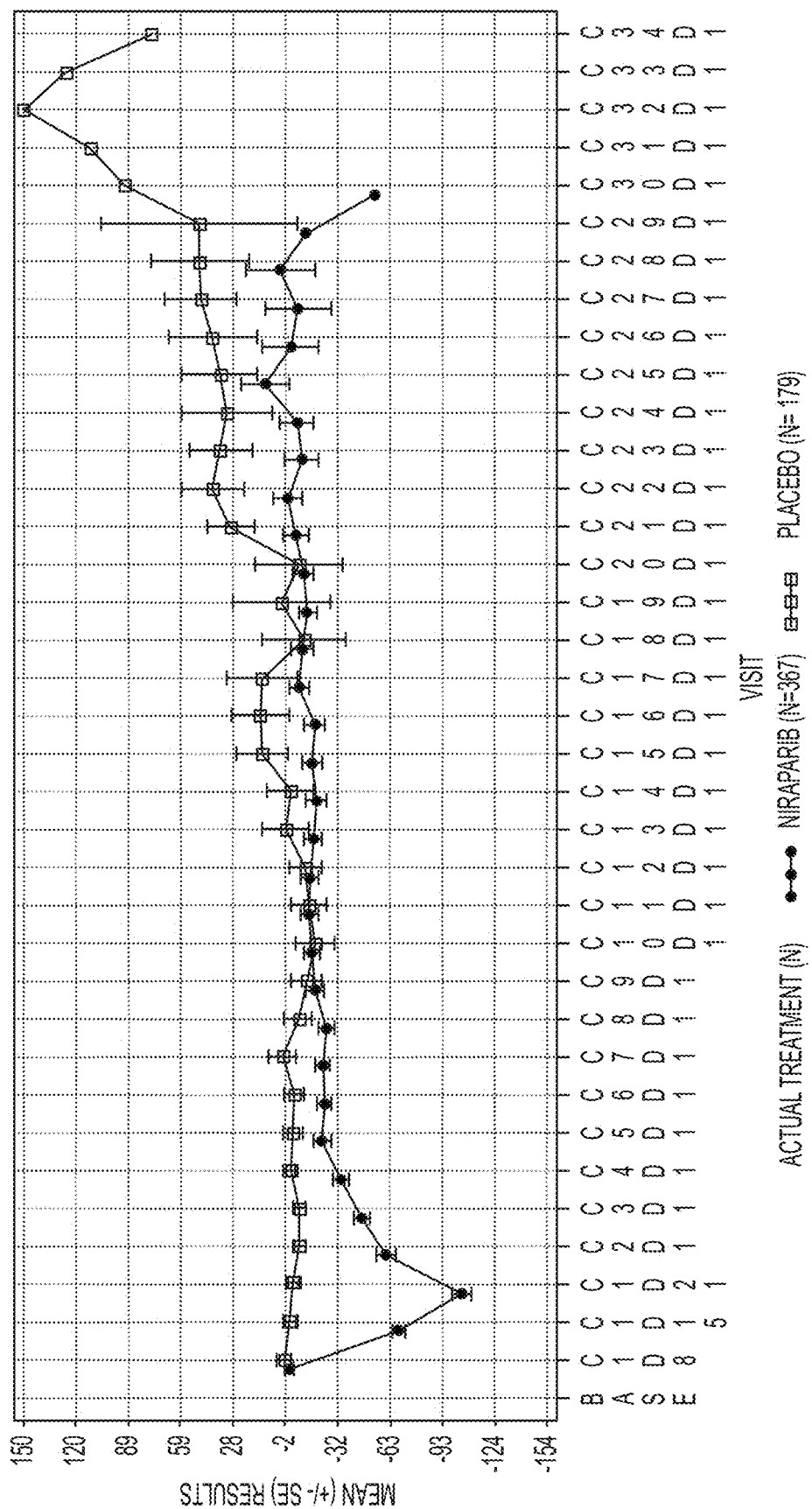
FIG. 8 depicts a graphical representation of the mean change from baseline (±SE) for platelets over time: all patients cohort.

Although Grade 3 or 4 TEAEs were frequent, dose modification was effective in reducing the frequency of these events during the treatment period. The incidence of thrombocytopenia over time exemplifies the effectiveness of the dose modifications. FIG. 8 shows the mean platelet count over time for the overall niraparib treated population. As platelet counts were collected weekly during the first cycle, the first four time points include C1D1, C1D8, C1D15, and C1D21. The subsequent time points were Day 1 of all remaining cycles. The mean platelet count decreased substantially by day 15; however, platelet counts continued to increase after this time point and generally returned to near baseline by Cycle 4.

Importantly, efficacy was not compromised in patients who were adjusted to a lower dose level. In order to assess the possible impact of dose reduction on the efficacy of niraparib, analyses of PFS were conducted based on each patient's last prescribed dose and on the dose that they received for the longest duration. Note that for these analyses, only patients who received at least 1 dose of niraparib were included. Results of the KM analyses by niraparib dose based on longest duration are provided in FIG. 9.

The most common dose of longest duration was 200 mg in both the gBRCA$^{mut}$ (74 of 136, 54%) and non-gBRCA$^{mut}$ (107 of 231, 46%) cohorts; 300 mg was the dose of longest duration in 25 (18%) and 73 (32%) patients in the gBRCA$^{mut}$ and non-gBRCA$^{mut}$ cohorts, respectively, and 100 mg was the dose of longest duration in 37 (27%) and 51 (22%) patients, respectively.

Figure 9:
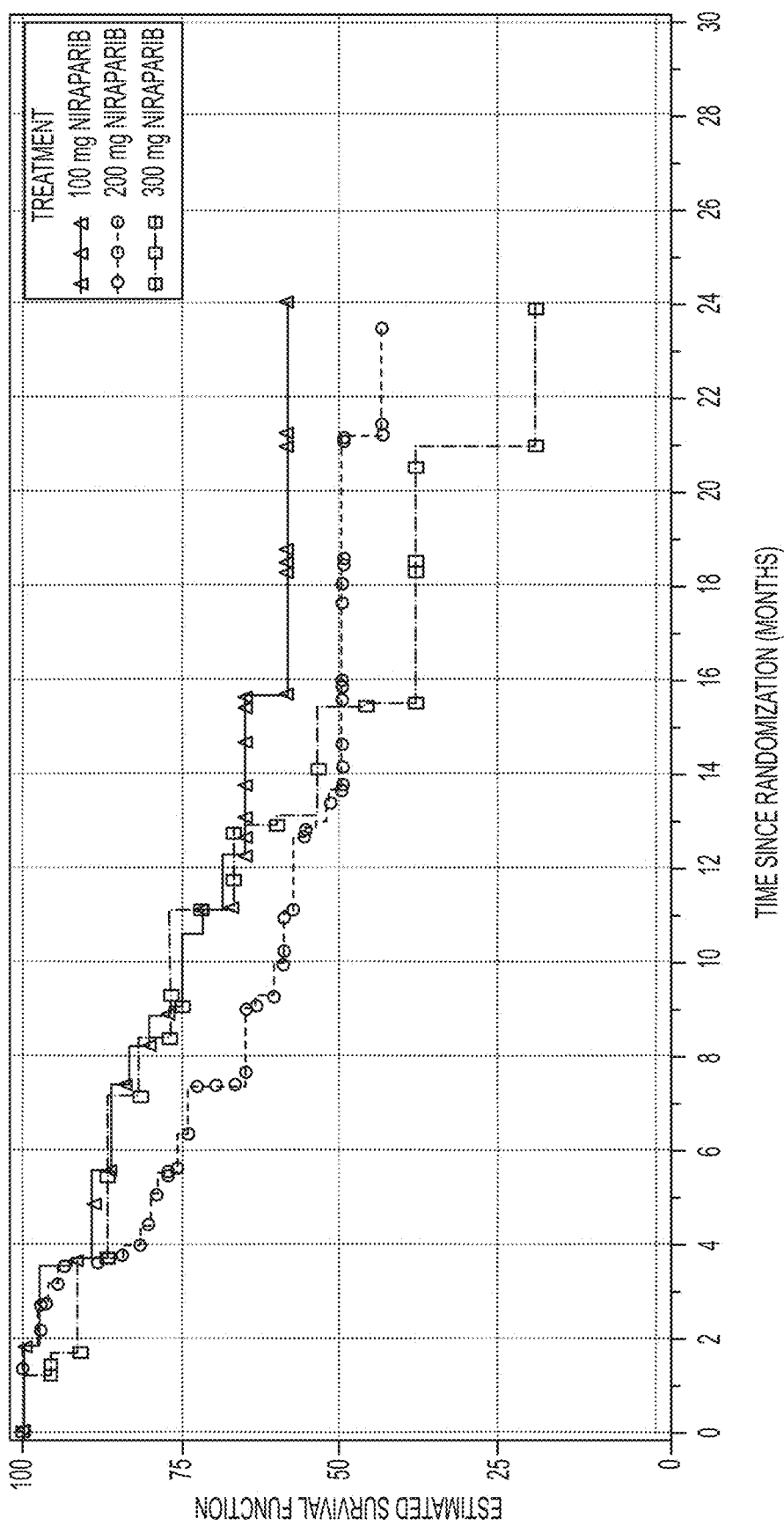
FIG. 9 depicts a graphical representation (Kaplan-Meier plot) of the progression-free survival in the gBRCAmut cohort based on IRC assessment by niraparib dose administered for the longest duration (niraparib patients in the safety population).
Figure 10:
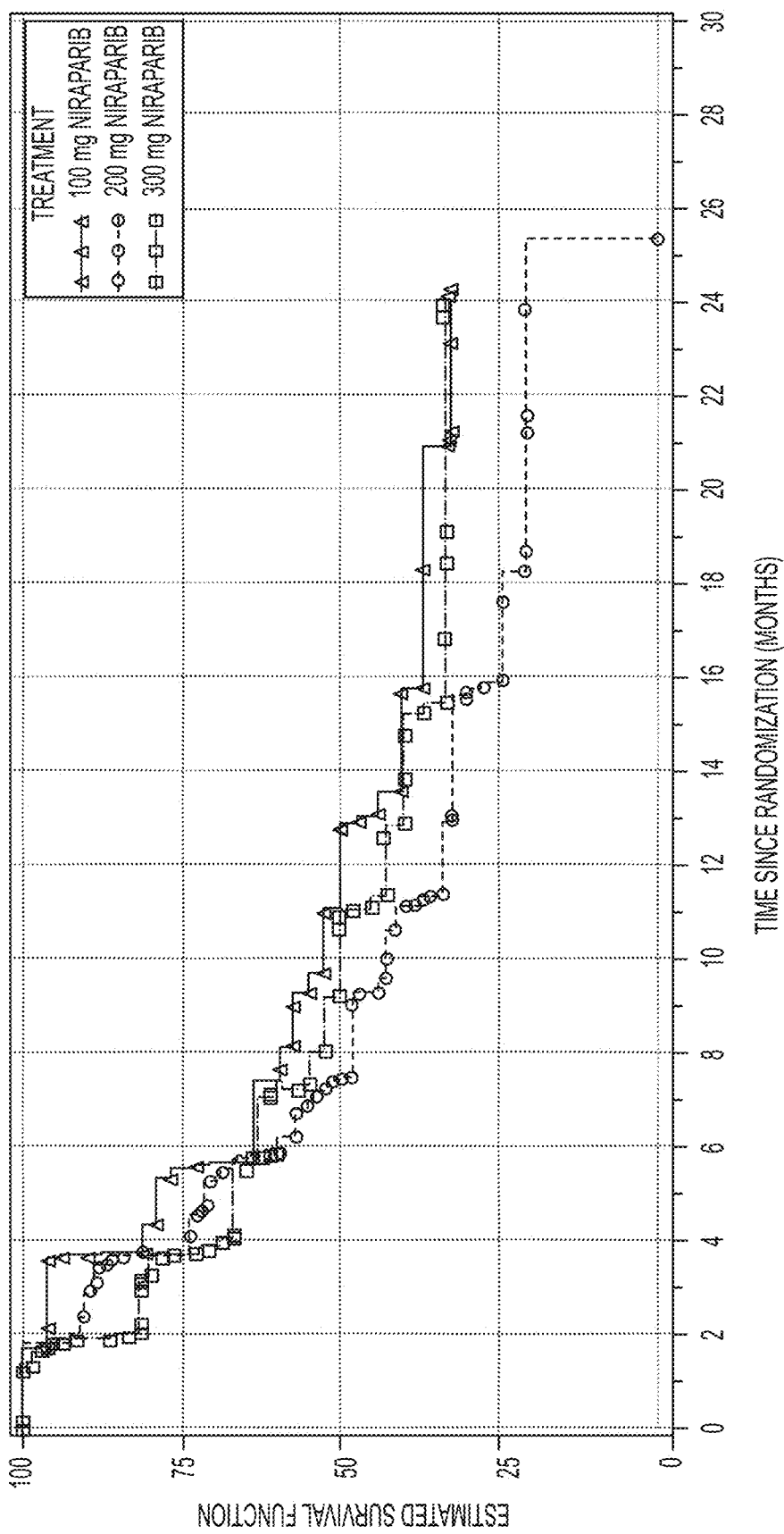
FIG. 10 depicts a graphical representation (Kaplan-Meier plot) of the progression-free survival in the non-gBRCAmut cohort based on IRC assessment by niraparib dose administered for the longest duration (niraparib patients in the safety population).

FIG. 9 and FIG. 10 present KM plots for PFS by niraparib dose of longest duration for the gBRCA$^{mut}$ and non gBRCA$^{mut}$ cohorts, respectively; as shown, PFS at all 3 doses was consistent with the overall population indicating that patients who required dose reduction do not have decreased efficacy relative to those who remain at the 300 mg starting dose.

Secondary Efficacy Analyses of Niraparib

Figure 13:
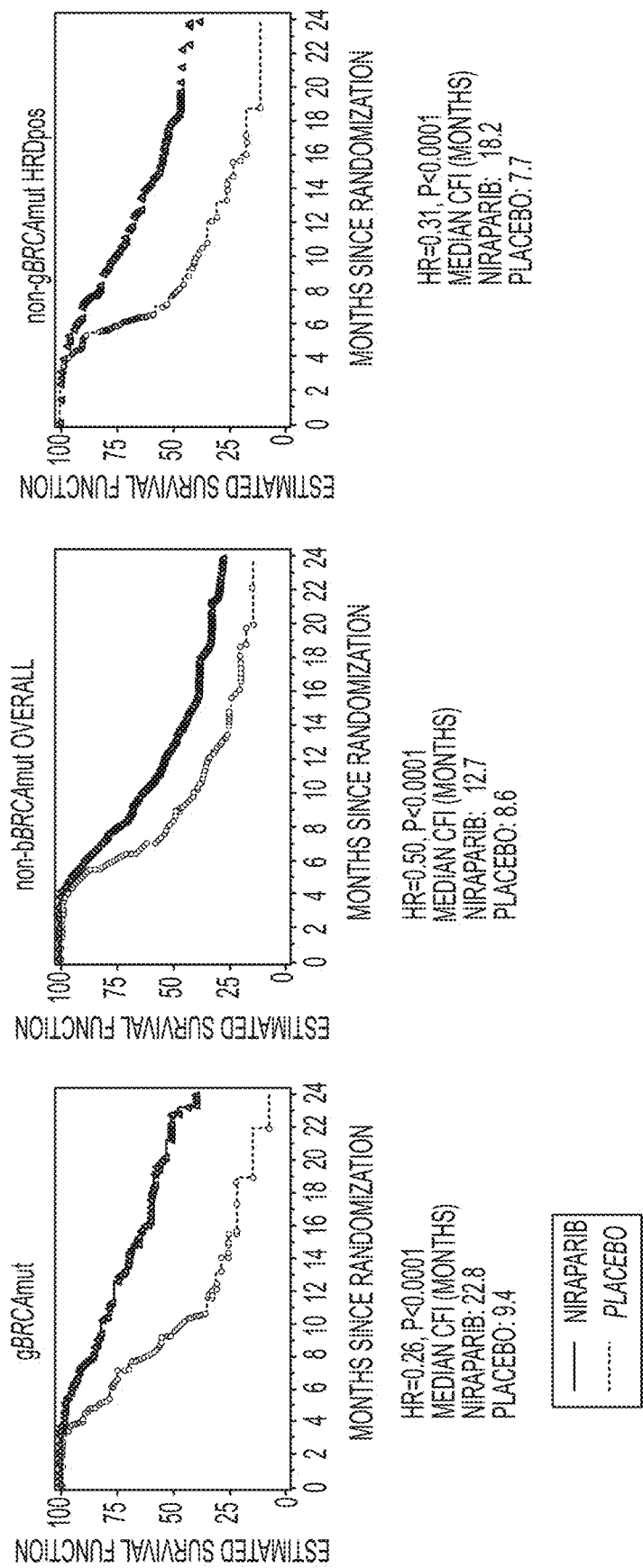
FIG. 13 depicts a graphical representation of analysis of chemotherapy-free survival interval in the (left panel) gBRCAmut Cohort, (center) overall non-gBRCAmut Cohort, and (right panel) non-gBRCAmut, HRDpos Subgroup.
Figure 14:
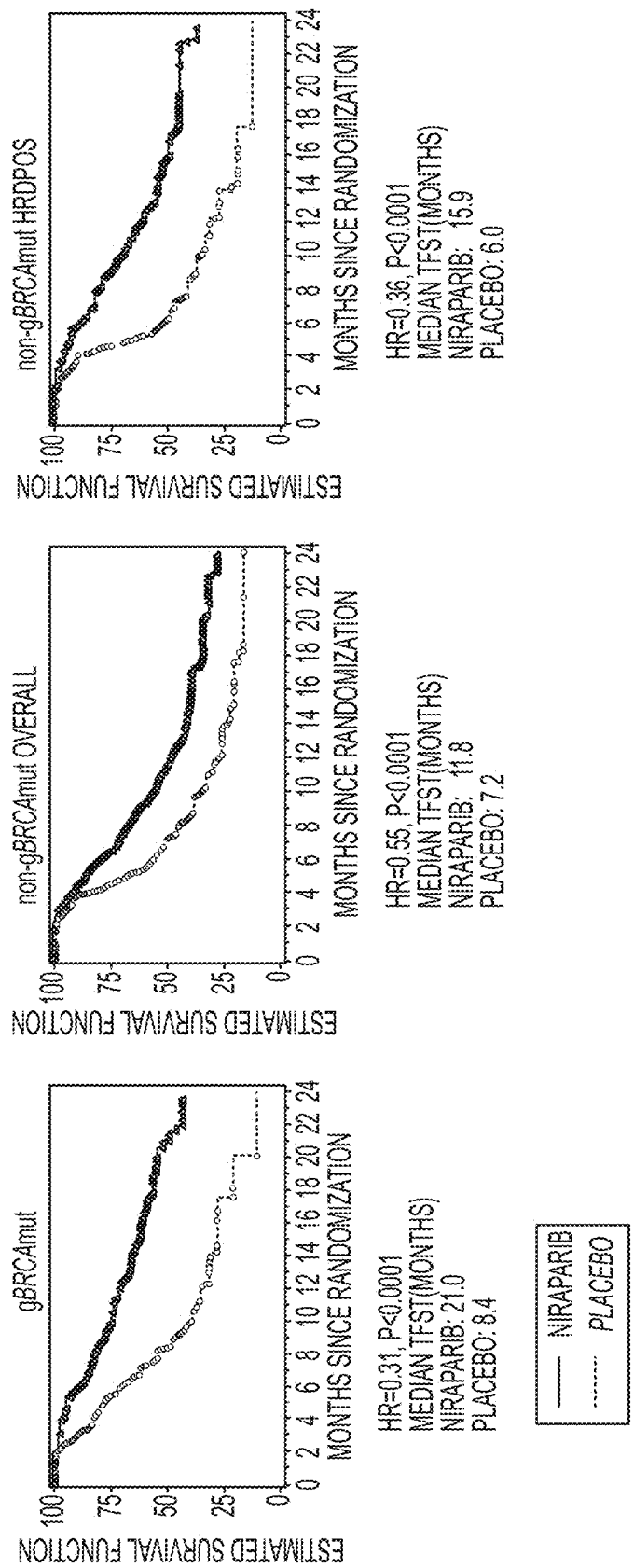
FIG. 14 depicts a graphical representation of analysis of time to first subsequent treatment in the (left panel) gBRCAmut Cohort, (center) overall non-gBRCAmut Cohort, and (right panel) non-gBRCAmut, HRDpos Subgroup.

Secondary efficacy endpoints include time to first subsequent treatment (TFST), time to second subsequent treatment (TSST), progression-free survival 2 (PFS2), chemotherapy-free interval (CFI), and overall survival (OS). Niraparib had greater efficacy than placebo across a majority of secondary efficacy end points that were evaluated (FIG. 11). Secondary endpoints such as PFS2, OS and CFI were analyzed using a stratified log-rank test. Stratified Cox proportional hazard models were used to estimate the treatment HR and its 95% CI. Maintenance treatment with niraparib significantly improved and chemotherapy-free interval and time to first subsequent treatment for patients in both cohorts; patients who received placebo required initiation with a subsequent treatment sooner than patients who were treated with niraparib, regardless of their biomarker status (FIGS. 11, 13 and 14). Progression-free survival 2 was significantly longer for patients who received niraparib for both cohorts. For patients in the gBRCA$^{mut}$ cohort, the progression-free survival 2 was 25.8 months in the niraparib group compared to 19.5 months in the placebo group (hazard ratio, 0.48; 95% CI, 0.280 to 0.821; P=0.0062). In the overall non-gBRCA$^{mut}$ cohort, the median PFS 2 was 18.64 months for niraparib compared to 15 months for placebo; hazard ratio, 0.649; 95% CI 0.494, 0.964; P=0.0293). The time to second subsequent therapy was also a secondary endpoint, however at the time of data cutoff too few patients had received a second treatment to perform this analysis (34/138 niraparib and 26/65 placebo in the gBRCA$^{mut}$ cohort, and 90/234 niraparib and 53/116 placebo in the non-gBRCA$^{mut}$ cohort).

Figure 15:
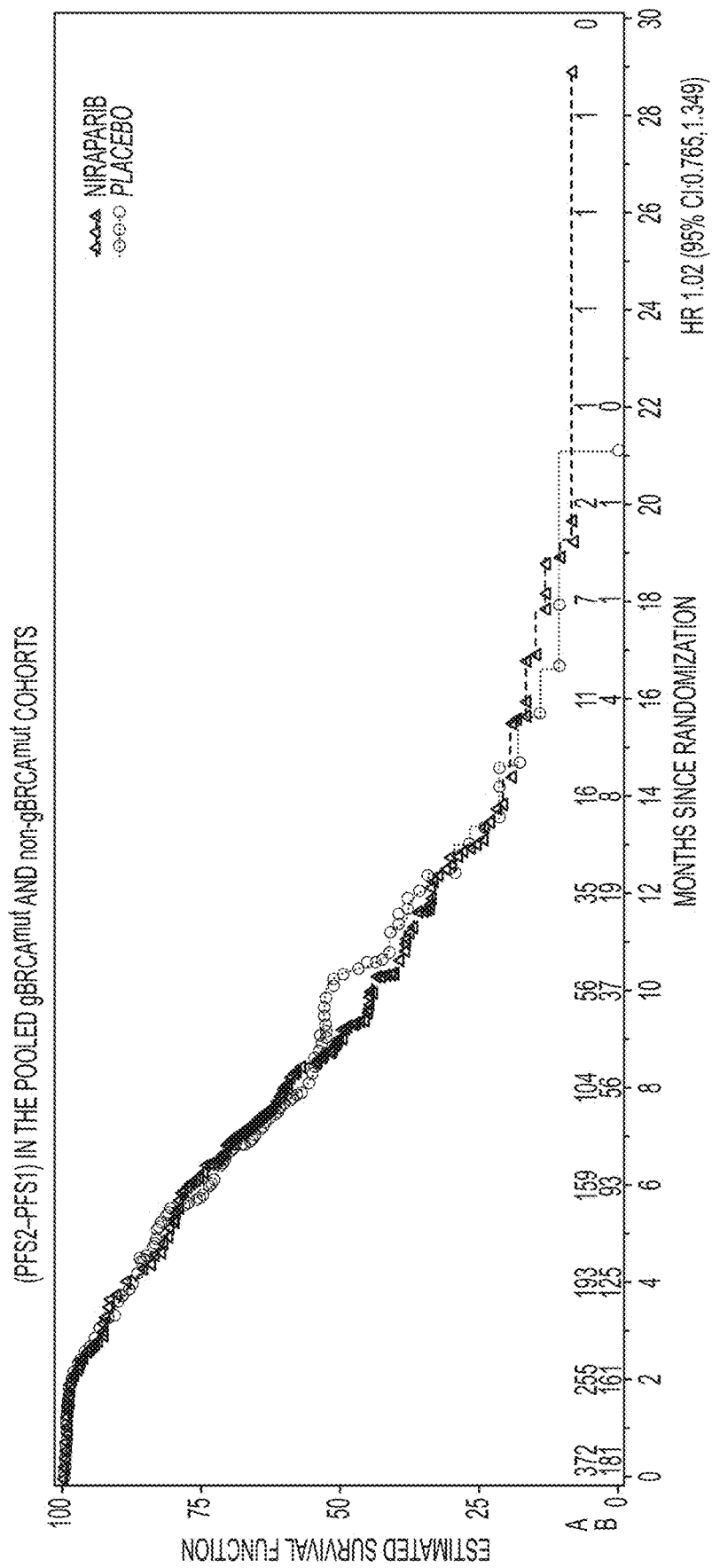
FIG. 15 depicts a graphical representation of analysis of efficacy of next-line treatment in the pooled gBRCA$^{mut}$ and non-gBRCA$^{mut}$ cohorts.

A pooled analysis looking at the combined study population (2 cohorts combined gBRCA$^{mut}$ and non-gBRCA$^{mut}$) for efficacy of next-line treatment. PFS2-PFS1 was similar in niraparib and placebo treated patients. (See FIG. 15).

A summary of the Secondary Efficacy Analysis of the gBRCA$^{mut}$, non-gBRCA$^{mut}$ and combined patient cohorts is provided in Table 5, below. "HR" indicates Hazard Ratio and "95% CI" means a 95% confidence interval.

TABLE 5

Secondary Efficacy Analysis - PFS2, Time to Subsequent Treatment and Overall Survival in gBRCA$^{mut}$, non-gBRCA$^{mut}$ and combined patient cohorts.

| PFS2 (data are immature, <50% of events) | |
|---|---|
| gBRCAmut: | HR 0.48 (95% CI: 0.280, 0.821) |
| Non-gBRCAmut: | HR 0.69 (95% CI: 0.494, 0.964) |
| Time to second subsequent treatment (data are immature, <40% of events) | |
| gBRCA mut: | HR 0.48 (95% CI: 0.272, 0.851) |
| Non-gBRCAmut: | HR 0.74 (95% CI: 0.519, 1.066) |
| Overall Survival (data are immature, 80% of patients censored) <20% patient deaths in either treatment arm | |
| Combined cohorts: | HR 0.73 (95% CI: 0.480, 1.125) |

Secondary endpoints, including CFI, TFST, TSST, and PFS2 demonstrated a persistent treatment effect in favor of the niraparib treatment arm in both gBRCA$^{mut}$ and non-gBRCA$^{mut}$ cohorts. Furthermore, no detrimental impact of niraparib treatment on OS was observed.

Figure 16:
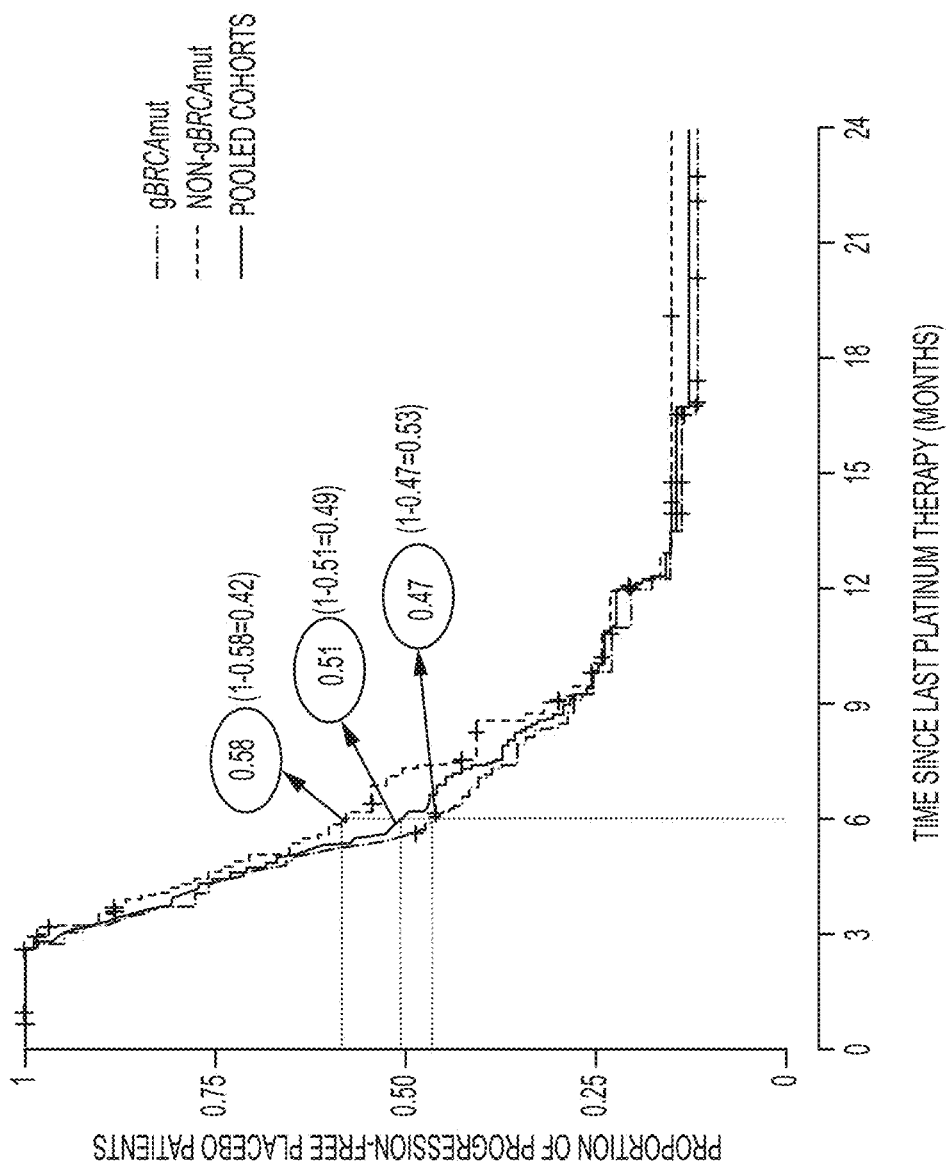
FIG. 16 depicts a graphical representation of the estimated probability of progressive disease at 6 months after the last dose of platinum-based therapy.

In niraparib versus placebo treated patients, the incidence of TEAEs was as follows: MDS/AML occurred in 1.4% (5 of 367) patients who received niraparib and 1.1% (2 of 179) patients who received placebo. No patient had a grade 3 or 4 bleeding event, although 1 patient had grade 3 petechiae and hematoma concurrent with pancytopenia. No grade 5 events occurred. Hematologic treatment-related TEAEs grade ≥3 were manageable through dose individualization. Subgroup Analyses Based on Last Platinum-Based Chemotherapy Response Platinum resistance status was assessed in patients receiving placebo treatment. Platinum resistance status was defined as a duration of response to platinum <6 months to the most recent (ultimate) platinum regimen. Estimated probability of patients having disease progression 6 months after the last dose of their most recent platinum therapy was calculated using Kaplan-Meier methodology. 181 patients were randomized to placebo (65 gBRCA$^{mut}$ and 116 non-gBRCA$^{mut}$). Platinum resistance rate estimates were for the gBRCA$^{mut}$, non-gBRCA$^{mut}$, and pooled cohorts were 42%, 53% and 49%, respectively, see FIG. 16. Therefore approximately half of the patients in trial had developed platinum resistance to their last line of chemotherapy. Disease progression after 12 months was also evaluated for each of the cohorts. A summary of the disease progression within 6 months and 12 months is shown in Table 6.

TABLE 6

Estimated Percentage of Placebo Patients with PD <6 or <12 Months After Their Last Dose of Platinum-Based Therapy

| Outcome | gBRCAmut (n = 65) | Non-gBRCAmut (n = 116) | Pooled Cohorts (n = 181) |
|---|---|---|---|
| PD <6 months | 42% | 53% | 49% |
| PD <12 months | 82% | 78% | 79% | gBRCAmut = germline breast cancer susceptibility gene mutation;
PD = progression of disease.

Patients were stratified based on their response to their most recent platinum treatment (CR or PR). 49% of patients in the gBRCA$^{mut}$ cohort (niraparib: 67/138; placebo: 32/65) and ~49% of patients in the non-gBRCA$^{mut}$ cohort (niraparib: 117/234 [50%]; placebo: 56/116 [48%]) entered the NOVA trial with a PR following their most recent platinum-based chemotherapy. At the time of unblinding, 30(45%) niraparib and 23 (72%) of placebo patients in the gBRCA$^{mut}$ cohort and 65 (56%) niraparib and 45 (80%) of placebo patients in the non-gBRCA$^{mut}$ cohort had PFS events. PFS hazard ratios (95% CI) were 0.24 (0.131-0.441) in gBRCA$^{mut}$ and 0.35 (0.230-0.532) in non-gBRCA$^{mut}$ cohorts for patients who had a PR to their most recent platinum regimen. The response in subjects who had a partial response in their most recent platinum-based chemotherapy treatment compares favorably to the overall NOVA study results described above.

Placebo-treated patients were further stratified based on their response to the last two platinum treatments. The characteristics of these placebo-treated patients are shown in Table 7. In the non-gBRCAmut cohort, a greater proportion of patients with PD <6 months (platinum resistant) had a PR following both the penultimate and the last platinum-based chemotherapy compared to those with PD ≥6 months (platinum sensitive) (39.7% vs 14.6% for the penultimate, and 65.5% vs 22.9% for the last).

TABLE 7

Placebo-Treated Patient Characteristics at Baseline

| Parameter | gBRCAmut | | Non-gBRCAmut | |
|---|---|---|---|---|
| Age, median (min, max) | 61.0 (42, 73) | 58.0 (38, 73) | 63.5 (41, 79) | 59.0 (38, 82) |
| Time from completion of last platinum therapy to randomization, median (min, max), days | 38.5 (21, 60) | 40 (11, 68) | 42 (22, 63) | 41.5 (20, 64) |
| Time to PD after penultimate platinum-based dose, n (%) | | | | |
| 6 to <12 months | 12 (50.0) | 10 (32.3) | 29 (50.0) | 10 (20.8) |
| ≥12 months | 12 (50.0) | 21 (67.7) | 29 (50.0) | 38 (79.2) |

TABLE 7-continued

Placebo-Treated Patient Characteristics at Baseline

| Parameter | gBRCAmut | | Non-gBRCAmut | |
|---|---|---|---|---|
| Best response to penultimate platinum-based therapy[a] | | | | |
| CR | 19 (79.2) | 22 (71.0) | 35 (60.3) | 40 (83.3) |
| PR | 5 (20.8) | 9 (29.0) | 23 (39.7) | 7 (14.6) |
| Best response to last platinum-based therapy | | | | |
| CR | 11 (45.8) | 19 (61.3) | 20 (34.5) | 37 (77.1) |
| PR | 13 (54.2) | 12 (38.7) | 38 (65.5) | 11 (22.9) |

Figure 17:
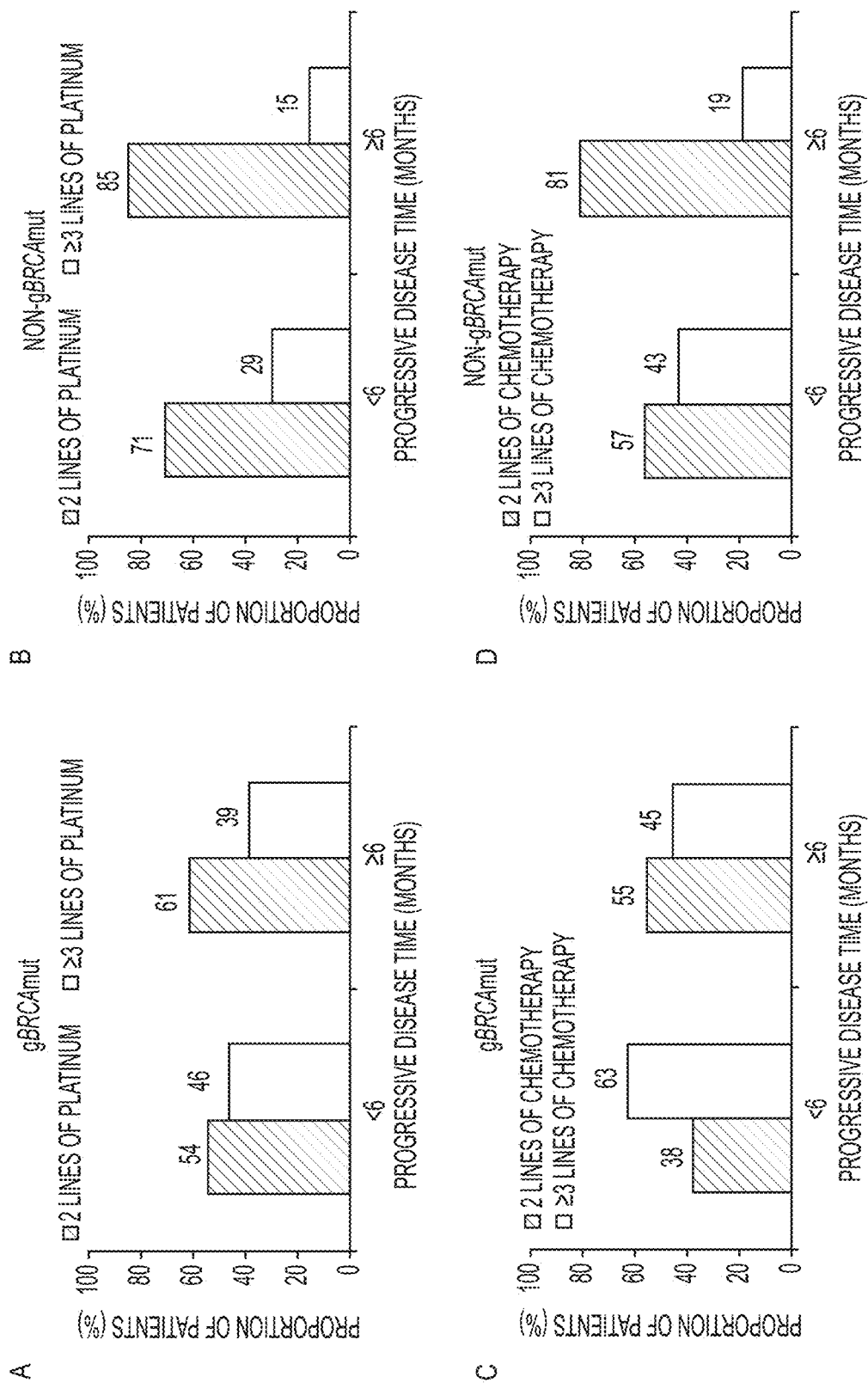
FIG. 17 depicts a graphical representation of the effect of the number of lines of chemotherapy on the proportion of patients time to disease progression, shown for platinum-based chemotherapy gBRCAmut (A), platinum-based chemotherapy non-gBRCAmut (B), total chemotherapy gBRCA mut (C) and total chemotherapy non-gBRCAmut (D) cohorts.

[a]One patient did not have last platinum-based chemotherapy information available.
CR = complete response;
gBRCAmut = germline breast cancer susceptibility gene mutation;
PD = progression of disease;
PR = partial response Placebo-treated patients were also stratified based on the number of lines of prior treatment they have received (2 versus 3 or more) and the results are shown in FIG. 17. The patients with PD <6 months after their last chemotherapy had received more prior lines of platinum-based therapy (FIG. 17, panels A and B) and more total lines of chemotherapy (FIG. 17, panels C and D) than those with PD ≥6 months after their most recent platinum-based chemotherapy.

Patient-Reported Outcomes

Figure 18:
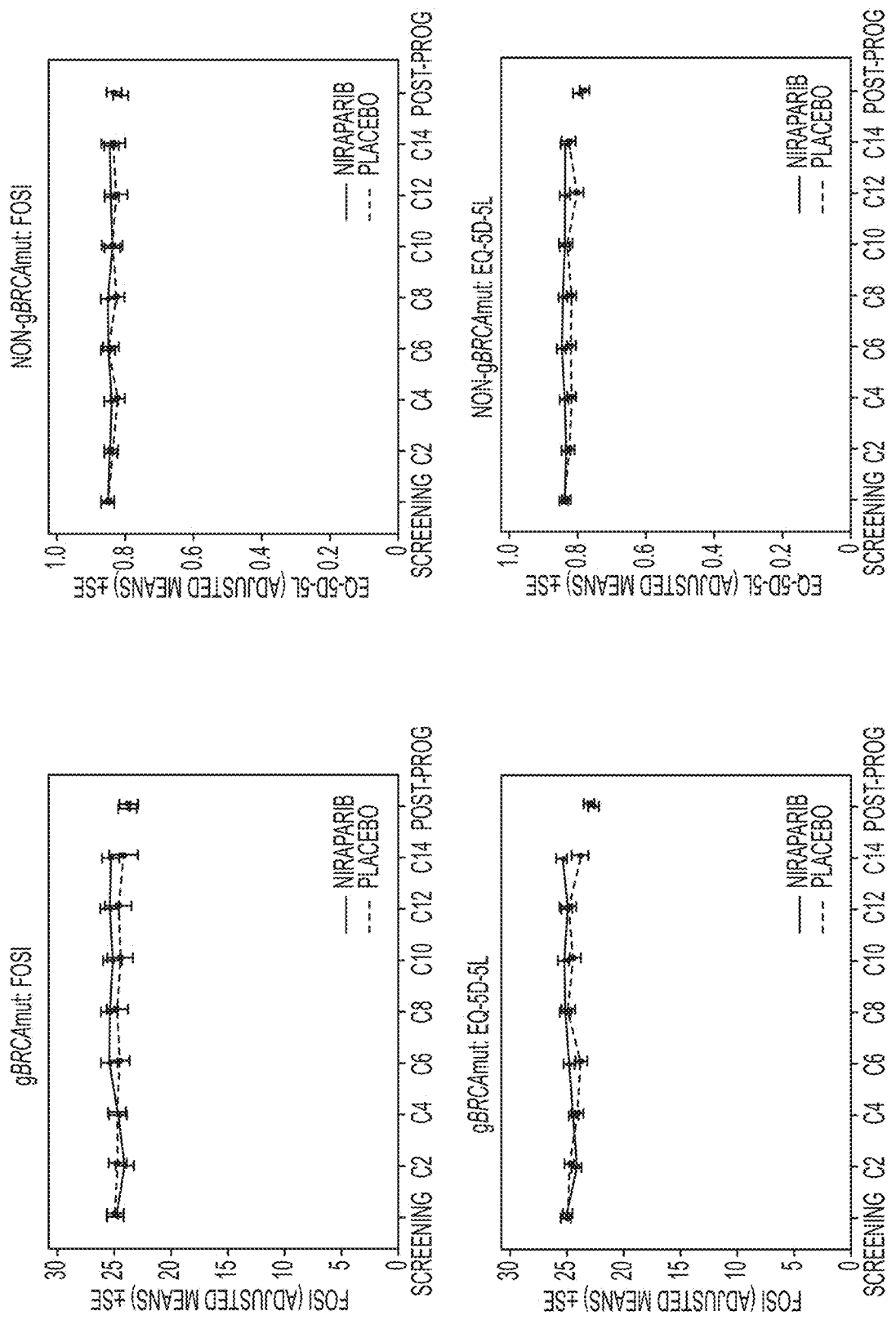
FIG. 18 depicts a graphical representation of patient reported outcomes using the Functional Assessment of Cancer Therapy-Ovarian Symptom Index (FOSI) and the EQ-5D-5L: patient-reported outcomes were similar for niraparib and placebo.

Patient-reported outcomes were measured using the Functional Assessment of Cancer Therapy—Ovarian Symptom Index (FOSI) and the EQ-5D-5L Health Utility Index (HUI) scores. Patient-reported outcomes (PRO) surveys were collected at: screening visit, every other cycle through cycle 14 and post progression. A mixed-effects growth curve model was constructed to model the relationship between treatment and PRO score for each measure. Responder proportions were assessed using minimally important difference thresholds and change from baseline values. The relationship between health status and patient-reported health outcomes was evaluated through a cross-sectional analysis of adjusted EQ-5D-5L Health Utility Index (HUI) scores. Compliance rates were high and similar between the two treatment arms: niraparib: FOSI completion rate ranged from 75.0% to 97.1% and placebo: FOSI completion rate ranged from 77.6% to 97.4%. PROs were similar for niraparib and placebo throughout the study in both the gBRCA$^{mut}$, non-gBRCA$^{mut}$ cohorts. See FIG. 18. No significant difference in mean PRO scores was observed between niraparib and placebo arms in either cohort. The analysis of responder proportions also did not demonstrate any significant difference, except in the non-gBRCA$^{mut}$ cohort at cycle 2. Adjusted HUI scores were similar in both arms at baseline, but average adjusted HUI pre-progression scores trended higher in the niraparib arm (0.812 vs. 0.803 in gBRCA$^{mut}$ cohort; 0.845 vs. 0.828 in non-gBRCA$^{mut}$ cohort. Hematologic toxicities had no detrimental effect on patients' overall health utility. These data support that patients with recurrent ovarian cancer treated with niraparib following complete or partial response to platinum-based chemotherapy can maintain their quality of life while on treatment with niraparib (e.g., while receiving niraparib maintenance therapy).

Conclusions

This study represents the first time a PARP inhibitor has demonstrated definitive activity in a patient population who may best be defined by their platinum sensitivity. These data support the expanded use of a PARP inhibitor beyond those cancers with a BRCA mutation, and shows efficacy of niraparib in both HRD positive and non-gBRCA ovarian cancers, including HRD negative ovarian cancers. A once daily dose of niraparib significantly extended the progression-free survival time of patients in all three primary efficacy populations: the gBRCAmut cohort, the prospectively defined subgroup of patients with HRD positive tumors in the non-gBRCAmut cohort, and the overall non-gBRCAmut cohort. The niraparib treatment effect, as manifest in the Kaplan-Meier curves, was clinically meaningful, consistent, and durable for all three primary efficacy populations. In addition, the secondary endpoints of chemotherapy-free interval, time to first subsequent therapy, and progression-free survival 2 were statistically significant and clinically meaningful for the niraparib treatment arm in both cohorts. Importantly, the patient-reported outcomes showed an outcome for niraparib maintenance therapy that was at least as good as placebo. Collectively, these data are strongly supportive of the use of niraparib in this patient population who might otherwise receive no treatment at all.

Exploratory analyses, and the resultant Kaplan-Meier curves, indicate that treatment with niraparib provides a consistent and durable benefit to patients compared to placebo in all exploratory subgroups, regardless of biomarker status, a finding that is consistent with observations made for the primary efficacy populations. Although there is variation in the response to niraparib among the different biomarker populations, significantly improved progression-free survival was observed for patients who lacked a BRCA mutation and had tumors that were not deficient in homologous recombination (HRD negative).

Secondary endpoints improved with niraparib as demonstrated by significantly prolonged PFS2, CFI, and TFST. Moreover, niraparib had no impact on the efficacy of the next line of therapy, suggesting a prolonged clinical benefit. Niraparib significantly improved outcome in patients with recurrent ovarian cancer following a partial or complete response to platinum-based chemotherapy regimen, regardless of BRCA mutation or HRD status.

The niraparib side effect profile was manageable, and acceptable for long-term dosing following a response to platinum-based chemotherapy. The dose of 300 mg is appropriate for the majority of patients, and acceptable given the life-threatening nature of the disease; this dose can be adapted for individual patients if necessary, greatly reducing the need to discontinue the drug due to side effects. Overall there were no deaths during treatment, and ~85% of patients remained on niraparib for the duration of the study, further indicating that side effects were acceptable and tolerated. Adverse events can be monitored routinely using standard assessments of hematological laboratory parameters, as is standard for patients receiving anticancer therapies. The incidence of myelodysplastic syndrome and/or acute myeloid leukemia was very low (1%) with similar rates in the niraparib and placebo treatment arms.

Niraparib is a daily oral treatment that prolongs the effect of platinum-based chemotherapy by substantially improving progression-free survival without reducing quality of life, delaying the need for additional platinum-based chemotherapy with its associated cumulative toxicities in patients with recurrent ovarian cancer, regardless of their biomarker status. Niraparib treatment provided significant efficacy in a broad population of patients, now expanding the benefit of PARP inhibitors to non-BRCA ovarian cancer patients who have platinum-sensitive, recurrent ovarian cancer following a response to platinum chemotherapy.

Example 2. Food Effects of Niraparib

A 14-day, open-label, 2-treatment, crossover sub-study evaluated the effect of a high fat meal on niraparib (single dose) exposure.

Patients with ovarian cancer regardless of platinum sensitivity and burden of disease were randomized to either Group A or Group B with 6 patients assigned to each group. In Group A, patients fasted (nothing to eat or drink except water) for at least 10 hours before receiving a single dose of 300 mg niraparib; patients continued to fast for at least 2 hours following the dose. In Group B, patients fasted for at least 10 hours before consuming a high fat meal. Within 5 minutes of finishing the meal, a single dose of 300 mg niraparib was administered orally and patients resumed fasting for at least 4 hours. After a 7-day PK assessment and wash-out period, all patients received their second single dose of niraparib on Day 8 under the opposite (fasting vs high fat meal) circumstance: the previous 6 patients in Group A received their single dose of niraparib after a high fat meal and patients in Group B received their second single dose of niraparib under fasting conditions. After the completion of the 14-day food effect sub-study, patients began daily dosing at 300 mg QD niraparib on Cycle 1/Day 1, approximately 2 weeks after the start of the study.

Having thus described several aspects of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

Example 3. DNA Repair Genes

TABLE 8 is a list of DNA Repair genes

| Gene Title | Gene Symbol |
|---|---|
| replication factor C (activator 1) 2, 40 kDa | RFC2 |
| X-ray repair complementing defective repair in Chinese hamster cells 6 (Ku autoantigen, 70 kDa) | XRCC6 |
| polymerase (DNA directed), delta 2, regulatory subunit 50 kDa | POLD2 |
| proliferating cell nuclear antigen | PCNA |

TABLE 8-continued is a list of DNA Repair genes

| Gene Title | Gene Symbol |
|---|---|
| replication protein A1, 70 kDa | RPA1 |
| replication protein A1, 70 kDa | RPA1 |
| replication protein A2, 32 kDa | RPA2 |
| excision repair cross-complementing rodent repair deficiency, complementation group 3 (xeroderma pigmentosum group B complementing) | ERCC3 |
| uracil-DNA glycosylase | UNG |
| excision repair cross-complementing rodent repair deficiency, complementation group 5 (xeroderma pigmentosum, complementation group G (Cockayne syndrome)) | ERCC5 |
| mutL homolog 1, colon cancer, nonpolyposis type 2 (E. coli) | MLH1 |
| ligase I, DNA, ATP-dependent | LIG1 |
| nibrin | NBN |
| nibrin | NBN |
| nibrin | NBN |
| mutS homolog 6 (E. coli) | MSH6 |
| polymerase (DNA-directed), delta 4 | POLD4 |
| replication factor C (activator 1) 5, 36.5 kDa | RFC5 |
| replication factor C (activator 1) 5, 36.5 kDa | RFC5 |
| damage-specific DNA binding protein 2, 48 kDa /// LIM homeobox 3 | DDB2 /// LHX3 |
| polymerase (DNA directed), delta 1, catalytic subunit 125 kDa | POLD1 |
| Fanconi anemia, complementation group G | FANCG |
| polymerase (DNA directed), beta | POLB |
| X-ray repair complementing defective repair in Chinese hamster cells 1 | XRCC1 |
| N-methylpurine-DNA glycosylase | MPG |
| replication factor C (activator 1) 2, 40 kDa | RFC2 |
| excision repair cross-complementing rodent repair deficiency, complementation group 1 (includes overlapping antisense sequence) | ERCC1 |
| excision repair cross-complementing rodent repair deficiency, complementation group 1 (includes overlapping antisense sequence) | ERCC1 |
| thymine-DNA glycosylase | TDG |
| thymine-DNA glycosylase | TDG |
| Fanconi anemia, complementation group A /// Fanconi anemia, complementation group A | FANCA |
| replication factor C (activator 1) 4, 37 kDa | RFC4 |
| replication factor C (activator 1) 3, 38 kDa | RFC3 |
| replication factor C (activator 1) 3, 38 kDa | RFC3 |
| APEX nuclease (apurinic/apyrimidinic endonuclease) 2 | APEX2 |
| RAD1 homolog (S. pombe) | RAD1 |
| RAD1 homolog (S. pombe) | RAD1 |
| breast cancer 1, early onset | BRCA1 |
| exonuclease 1 | EXO1 |
| flap structure-specific endonuclease 1 | FEN1 |
| flap structure-specific endonuclease 1 | FEN1 |
| mutL homolog 3 (E. coli) | MLH3 |
| O-6-methylguanine-DNA methyltransferase | MGMT |
| RAD51 homolog (RecA homolog, E. coli) (S. cerevisiae) | RAD51 |
| RAD51 homolog (RecA homolog, E. coli) (S. cerevisiae) | RAD51 |
| X-ray repair complementing defective repair in Chinese hamster cells 4 | XRCC4 |
| X-ray repair complementing defective repair in Chinese hamster cells 4 | XRCC4 |
| RecQ protein-like (DNA helicase Q1-like) | RECQL |
| excision repair cross-complementing rodent repair deficiency, complementation group 8 | ERCC8 |
| Fanconi anemia, complementation group C | FANCC |
| 8-oxoguanine DNA glycosylase | OGG1 |
| MRE11 meiotic recombination 11 homolog A (S. cerevisiae) | MRE11A |
| RAD52 homolog (S. cerevisiae) | RAD52 |
| Werner syndrome | WRN |
| xeroderma pigmentosum, complementation group A | XPA |
| Bloom syndrome | BLM |
| 8-oxoguanine DNA glycosylase | OGG1 |

TABLE 8-continued is a list of DNA Repair genes

| Gene Title | Gene Symbol |
| --- | --- |
| mutS homolog 3 (*E. coli*) | MSH3 |
| polymerase (DNA directed), epsilon 2 (p59 subunit) | POLE2 |
| RAD51 homolog C (*S. cerevisiae*) | RAD51C |
| ligase IV, DNA, ATP-dependent | LIG4 |
| excision repair cross-complementing rodent repair deficiency, complementation group 6 | ERCC6 |
| ligase III, DNA, ATP-dependent | LIG3 |
| RAD17 homolog (*S. pombe*) | RAD17 |
| X-ray repair complementing defective repair in Chinese hamster cells 2 | XRCC2 |
| mutY homolog (*E. coli*) | MUTYH |
| replication factor C (activator 1) 1, 145 kDa /// replication factor C (activator 1) 1, 145 kDa | RFC1 |
| replication factor C (activator 1) 1, 145 kDa | RFC1 |
| breast cancer 2, early onset | BRCA2 |
| RAD50 homolog (*S. cerevisiae*) | RAD50 |
| damage-specific DNA binding protein 1, 127 kDa | DDB1 |
| X-ray repair complementing defective repair in Chinese hamster cells 5 (double-strand-break rejoining; Ku autoantigen, 80 kDa) | XRCC5 |
| X-ray repair complementing defective repair in Chinese hamster cells 5 (double-strand-break rejoining; Ku autoantigen, 80 kDa) | XRCC5 |
| poly (ADP-ribose) polymerase family, member 1 | PARP1 |
| polymerase (DNA directed), epsilon 3 (p17 subunit) | POLE3 |
| replication factor C (activator 1) 1, 145 kDa | RFC1 |
| RAD50 homolog (*S. cerevisiae*) | RAD50 |
| xeroderma pigmentosum, complementation group C | XPC |
| mutS homolog 2, colon cancer, nonpolyposis type 1 (*E. coli*) | MSH2 |
| replication protein A3, 14 kDa | RPA3 |
| methyl-CpG binding domain protein 4 | MBD4 |
| methyl-CpG binding domain protein 4 | MBD4 |
| nth endonuclease III-like 1 (*E. coli*) | NTHL1 |
| PMS2 postmeiotic segregation increased 2 (*S. cerevisiae*) /// PMS2-C terminal-like | PMS2 /// PMS2CL |
| RAD51 homolog C (*S. cerevisiae*) | RAD51C |
| uracil-DNA glycosylase 2 | UNG2 |
| APEX nuclease (multifunctional DNA repair enzyme) 1 | APEX1 |
| excision repair cross-complementing rodent repair deficiency, complementation group 4 | ERCC4 |
| RAD1 homolog (*S. pombe*) | RAD1 |
| RecQ protein-like 5 | RECQL5 |
| mutS homolog 5 (*E. coli*) | MSH5 |
| RecQ protein-like (DNA helicase Q1-like) | RECQL |
| RAD52 homolog (*S. cerevisiae*) | RAD52 |
| X-ray repair complementing defective repair in Chinese hamster cells 4 | XRCC4 |
| X-ray repair complementing defective repair in Chinese hamster cells 4 | XRCC4 |
| RAD17 homolog (*S. pombe*) | RAD17 |
| mutS homolog 3 (*E. coli*) | MSH3 |
| MRE11 meiotic recombination 11 homolog A (*S. cerevisiae*) | MRE11A |
| mutS homolog 6 (*E. coli*) | MSH6 |
| mutS homolog 6 (*E. coli*) | MSH6 |
| RecQ protein-like 5 | RECQL5 |
| breast cancer 1, early onset | BRCA1 |
| RAD52 homolog (*S. cerevisiae*) | RAD52 |
| polymerase (DNA-directed), delta 3, accessory subunit | POLD3 |
| mutS homolog 5 (*E. coli*) | MSH5 |
| excision repair cross-complementing rodent repair deficiency, complementation group 2 (xeroderma pigmentosum D) | ERCC2 |
| RecQ protein-like 4 | RECQL4 |
| PMS1 postmeiotic segregation increased 1 (*S. cerevisiae*) | PMS1 |
| zinc finger protein 276 homolog (mouse) | ZFP276 |
| methyl-CpG binding domain protein 4 | MBD4 |
| methyl-CpG binding domain protein 4 | MBD4 |
| mutL homolog 3 (*E. coli*) | MLH3 |
| Fanconi anemia, complementation group A | FANCA |
| polymerase (DNA directed), epsilon | POLE |
| X-ray repair complementing defective repair in Chinese hamster cells 3 | XRCC3 |
| mutL homolog 3 (*E. coli*) | MLH3 |
| nibrin | NBN |
| single-strand selective monofunctional uracil DNA glycosylase | SMUG1 |
| Fanconi anemia, complementation group F | FANCF |
| nei endonuclease VIII-like 1 (*E. coli*) | NEIL1 |
| Fanconi anemia, complementation group E | FANCE |
| mutS homolog 5 (*E. coli*) | MSH5 |
| RecQ protein-like 5 | RECQL5 |

REFERENCES du Bois, A, Floquet A, Kim J W, Rau J, Del Campo J M, Friedlander M, Pignata S, Fujiwara K, Vergote I, Colombo, N, Mirza M R, Monk B J, Wimberger P, Ray-Coquard I, Zang R, Padilla I D, Baumann K H, Kim J H, and Harter P. Randomized, double-blind, phase III trial of pazopanib versus placebo in women who have not progressed after first-line chemotherapy for advanced epithelial ovarian, fallopian tube, or primary peritoneal cancer (AEOC): Results of an international Intergroup trial (AGO-OVAR16).

Pfisterer, J., M. Plante, I. Vergote, A. du Bois, H. Hirte, A. J. Lacave, U. Wagner, A. Stahle, G. Stuart, R. Kimmig, S. Olbricht, T. Le, J. Emerich, W. Kuhn, J. Bentley, C. Jackisch, H. J. Luck, J. Rochon, A. H. Zimmermann, E. Eisenhauer, O. Ago, C. T. G. Ncic and G. C. G. Eortc (2006). "Gemcitabine plus carboplatin compared with carboplatin in patients with platinum-sensitive recurrent ovarian cancer: an intergroup trial of the AGO-OVAR, the NCIC CTG, and the EORTC GCG." J Clin Oncol 24(29): 4699-4707.

TCGA (2011). "Integrated genomic analyses of ovarian carcinoma." Nature 474: 609-615.

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

The invention claimed is:

1. A method of treating a patient diagnosed with ovarian cancer, fallopian tube cancer, or primary peritoneal cancer, comprising
    administering daily to said patient an oral dose of niraparib equivalent to 200 mg or 300 mg of niraparib free base,
    wherein the patient has undergone at least one cycle of platinum-based chemotherapy; and
    wherein the patient carries no germline or somatic mutation in BRCA1 or BRCA2 genes and the cancer has no homologous recombination deficiency.

2. The method of claim 1, wherein the ovarian cancer, fallopian tube cancer, or primary peritoneal cancer is platinum sensitive.

3. The method of claim 1, wherein the patient has undergone at least two cycles of platinum-based chemotherapy.

4. The method of claim 3, wherein the patient has a complete response to the platinum-based chemotherapy.

5. The method of claim 3, wherein the patient has a partial response to the platinum-based chemotherapy.

6. The method of claim 3, wherein the administration of niraparib is commenced within 8 weeks of the end of the last cycle of platinum-based chemotherapy.

7. The method of claim 1, comprising administering the niraparib in continuous 28-day cycles.

8. The method of claim 1, wherein the niraparib is administered daily for a period of 6.9 months, and wherein administration is continued until disease progression occurs.

9. The method of claim 1, comprising administering daily to said patient an oral dose of niraparib tosylate monohydrate.

10. The method of claim 9, comprising administering daily to said patient an oral dose of niraparib tosylate monohydrate equivalent to 200 mg of niraparib free base.

11. The method of claim 9, comprising administering daily to said patient an oral dose of niraparib tosylate monohydrate equivalent to 300 mg of niraparib free base.

12. A method of treating a patient diagnosed with ovarian cancer, fallopian tube cancer, or primary peritoneal cancer, consisting of
    administering daily to said patient an oral dose of niraparib equivalent to 200 mg or 300 mg of niraparib free base,
    wherein the patient has undergone at least one cycle of platinum-based chemotherapy; and
    wherein the patient carries no germline or somatic mutation in BRCA1 or BRCA2 genes and the cancer has no homologous recombination deficiency.

13. The method of claim 12, wherein the ovarian cancer, fallopian tube cancer, or primary peritoneal cancer is platinum sensitive.

14. The method of claim 12, wherein the patient has undergone at least two cycles of platinum-based chemotherapy.

15. The method of claim 14, wherein the patient has a complete response to the platinum-based chemotherapy.

16. The method of claim 14, wherein the patient has a partial response to the platinum-based chemotherapy.

17. The method of claim 14, wherein the administration of niraparib is commenced within 8 weeks of the end of the last cycle of platinum-based chemotherapy.

18. The method of claim 12, comprising administering the niraparib in continuous 28-day cycles.

19. The method of claim 12, wherein the niraparib is administered daily for a period of 6.9 months, and wherein administration is continued until disease progression occurs.

20. The method of claim 12, comprising administering daily to said patient an oral dose of niraparib tosylate monohydrate.

21. The method of claim 20, comprising administering daily to said patient an oral dose of niraparib tosylate monohydrate equivalent to 200 mg of niraparib free base.

22. The method of claim 20, comprising administering daily to said patient an oral dose of niraparib tosylate monohydrate equivalent to 300 mg of niraparib free base.

* * * * *